US008615377B1

United States Patent
Yuen et al.

(10) Patent No.: US 8,615,377 B1
(45) Date of Patent: Dec. 24, 2013

(54) METHODS AND SYSTEMS FOR PROCESSING SOCIAL INTERACTIVE DATA AND SHARING OF TRACKED ACTIVITY ASSOCIATED WITH LOCATIONS

(71) Applicant: Fitbit, Inc., San Francisco, CA (US)

(72) Inventors: Shelten Gee Jao Yuen, Berkeley, CA (US); James Park, Berkeley, CA (US); Hans Christiansen Lee, Carmel, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 13/959,706

(22) Filed: Aug. 5, 2013

Related U.S. Application Data

(60) Continuation-in-part of application No. 13/693,334, filed on Dec. 4, 2012, now Pat. No. 8,548,770, which is a division of application No. 13/667,229, filed on Nov. 2, 2012, now Pat. No. 8,437,980, which is a division of application No. 13/469,027, filed on May 10, 2012, now Pat. No. 8,311,769, which is a division of application No. 13/246,843, filed on Sep. 27, 2011, now Pat. No. 8,180,591, which is a division of application No. 13/156,304, filed on Jun. 8, 2011, application No. 13/959,706, which is a continuation-in-part of application No. 13/759,485, filed on Feb. 5, 2013, now Pat. No. 8,543,351, which is a division of application No. 13/667,229, filed on Nov. 2, 2012, now Pat. No. 8,437,980, which is a division of application No. 13/469,027, filed on May 10, 2012, now Pat. No. 8,311,769, which is a division of application No. 13/246,843, filed on Sep. 27, 2011, now Pat. No. 8,180,591, which is a division of application No. 13/156,304, filed on Jun. 8, 2011.

(60) Provisional application No. 61/388,595, filed on Sep. 30, 2010, provisional application No. 61/390,811, filed on Oct. 7, 2010, provisional application No. 61/680,230, filed on Aug. 6, 2012.

(51) Int. Cl.
*G06F 19/00* (2011.01)

(52) U.S. Cl.
CPC ..................................... *G06F 19/00* (2013.01)
USPC ....................................................... 702/160

(58) Field of Classification Search
USPC .................. 702/150, 155, 160, 182–185, 188
See application file for complete search history.

(56) References Cited

U.S. PATENT DOCUMENTS

2006/0282021 A1* 12/2006 DeVaul et al. ................ 600/595

* cited by examiner

*Primary Examiner* — Edward Raymond
(74) *Attorney, Agent, or Firm* — Martine Penilla Group, LLP

(57) ABSTRACT

A method includes determining a location of a first monitoring device used while performing an activity. The first monitoring device is worn by a first user. The method includes determining a location of a second monitoring device used while performing an activity. The second monitoring device is worn by a second user. The method further includes determining whether the locations of the first and second monitoring devices are within a range and whether the activities are similar. The method includes sending a prompt to the first monitoring device upon determining that the activities are similar and the locations are within the range. The prompt includes a request for permission from a first user account to allow a second user account to access information from the first user account regarding the activity performed using the first monitoring device.

30 Claims, 39 Drawing Sheets

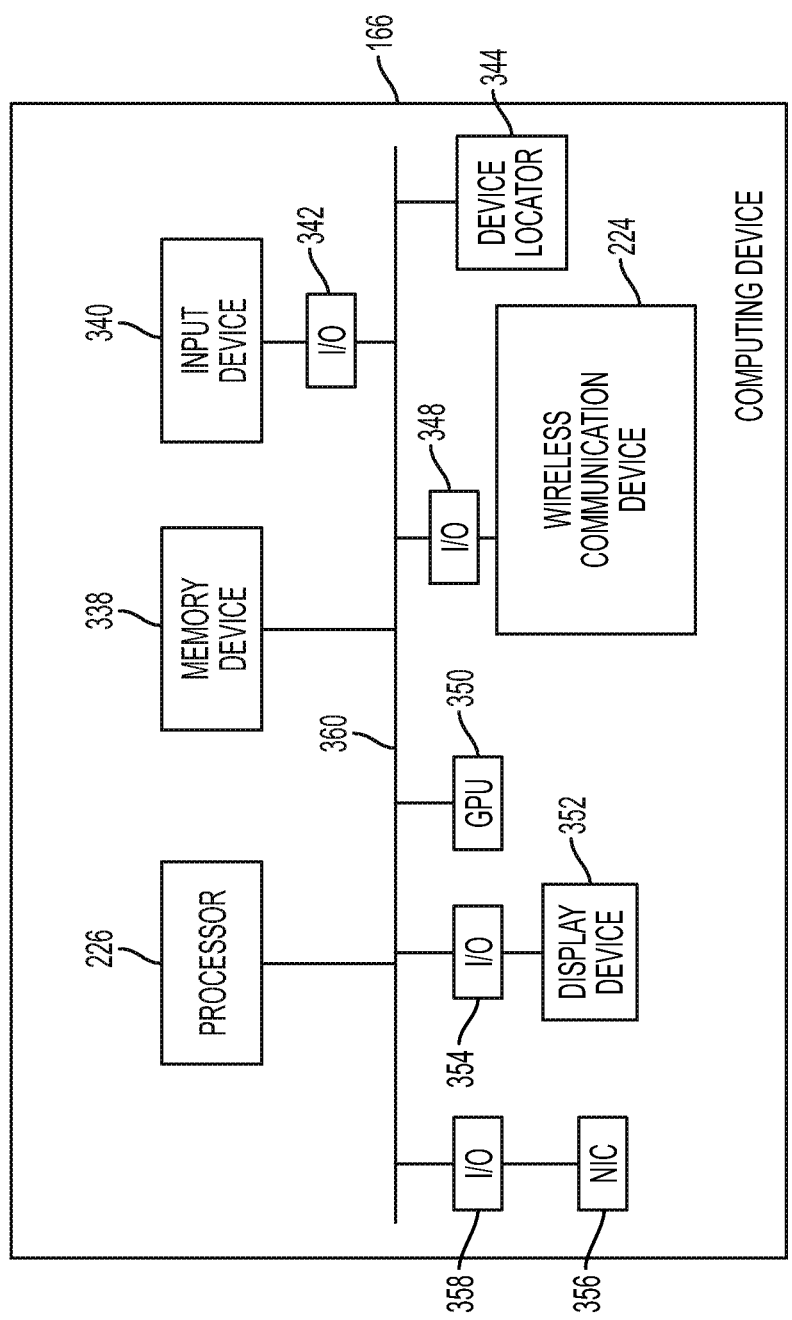

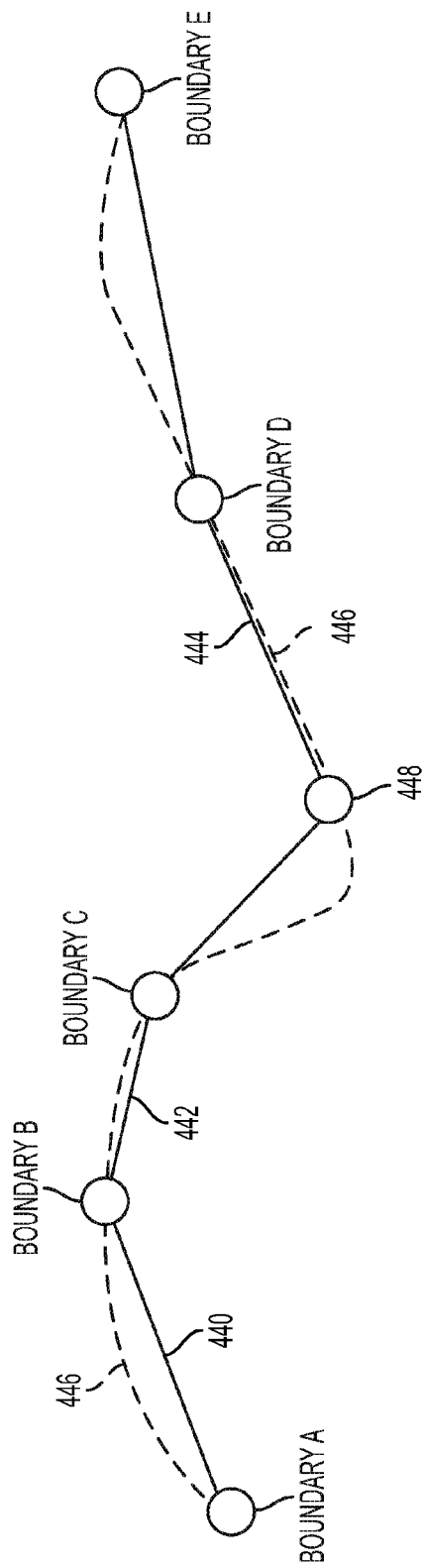

METHODS AND SYSTEMS FOR PROCESSING SOCIAL INTERACTIVE DATA AND SHARING OF TRACKED ACTIVITY ASSOCIATED WITH LOCATIONS

CLAIM OF PRIORITY

This application claims the benefit of and priority, under 35 U.S.C. 119§(e), to a Provisional Patent Application No. 61/680,230, filed on Aug. 6, 2012, and entitled "GPS ENABLED ACTIVITY AND SLEEP TRACKER," which is incorporated by reference herein in its entirety.

This application is a continuation-in-part of U.S. patent application Ser. No. 13/693,334, published as U.S. Patent Application Publication No. 20130096843, filed on Dec. 4, 2012, titled "Portable Monitoring Devices and Methods for Operating Same", which is a divisional of U.S. patent application Ser. No. 13/667,229, filed on Nov. 2, 2012, titled "Portable Monitoring Devices and Methods for Operating Same", which is a divisional of U.S. patent application Ser. No. 13/469,027, now U.S. Pat. No. 8,311,769, filed on May 10, 2012, titled "Portable Monitoring Devices and Methods for Operating Same", which is a divisional of U.S. patent application Ser. No. 13/246,843, now U.S. Pat. No. 8,180,591, filed on Sep. 27, 2011, which is a divisional of U.S. patent application Ser. No. 13/156,304, filed on Jun. 8, 2011, titled "Portable Monitoring Devices and Methods for Operating Same", which claims the benefit of and priority to, under 35 U.S.C. 119§(e), to U.S. Provisional Patent Application No. 61/388,595, filed on Sep. 30, 2010, and titled "Portable Monitoring Devices and Methods for Operating Same" and to U.S. Provisional Patent Application No. 61/390,811, filed on Oct. 7, 2010, and titled "Portable Monitoring Devices and Methods for Operating Same", all of which are hereby incorporated by reference in their entirety.

This application is a continuation-in-part of U.S. patent application Ser. No. 13/759,485, published as U.S. Patent Application Publication No. 20130151196, filed on Feb. 5, 2013, titled "Portable Monitoring Devices and Methods for Operating Same", which is a divisional of U.S. patent application Ser. No. 13/667,229, filed on Nov. 2, 2012, titled "Portable Monitoring Devices and Methods for Operating Same", which is a divisional of U.S. patent application Ser. No. 13/469,027, now U.S. Pat. No. 8,311,769, filed on May 10, 2012, titled "Portable Monitoring Devices and Methods for Operating Same", which is a divisional of U.S. patent application Ser. No. 13/246,843, now U.S. Pat. No. 8,180,591, filed on Sep. 27, 2011, which is a divisional of U.S. patent application Ser. No. 13/156,304, filed on Jun. 8, 2011, titled "Portable Monitoring Devices and Methods for Operating Same", which claims the benefit of and priority to, under 35 U.S.C. 119§(e), to U.S. Provisional Patent Application No. 61/388,595, filed on Sep. 30, 2010, and titled "Portable Monitoring Devices and Methods for Operating Same" and to U.S. Provisional Patent Application No. 61/390,811, filed on Oct. 7, 2010, and titled "Portable Monitoring Devices and Methods for Operating Same", all of which are hereby incorporated by reference in their entirety.

CROSS-REFERENCE TO RELATED APPLICATIONS

This application is related to U.S. patent application Ser. No. 13/959,714, filed on Aug. 5, 2013, and titled "Methods and Systems for Identification of Event Data having Combined Activity and Location Information of Portable Monitoring Devices", which is hereby incorporated by reference in its entirety.

This application is related to U.S. patent application Ser. No. 13/959,717, filed on Aug. 5, 2013, and titled "Methods and Systems for Generation and Rendering Interactive Events having Combined Activity and Location Information", which is hereby incorporated by reference in its entirety.

This application is related to U.S. patent application Ser. No. 13/959,719, filed on Aug. 5, 2013, and titled "Calendar Integration Methods and Systems for Presentation of Events having Combined Activity and Location Information", which is hereby incorporated by reference in its entirety.

This application is related to U.S. patent application Ser. No. 13/959,720, filed on Aug. 5, 2013, and titled "Methods and Systems for Interactive Goal Setting and Recommender using Events having Combined Activity and Location Information", which is hereby incorporated by reference in its entirety.

This application is related to U.S. patent application Ser. No. 13/959,681, filed on Aug. 5, 2013, and titled "Methods and Systems for Metrics Analysis and Interactive Rendering, including Events having Combined Activity and Location Information", which is hereby incorporated by reference in its entirety.

This application is related to U.S. patent application Ser. No. 13/959,694, filed on Aug. 5, 2013, and titled "Methods and Systems for Geo-location Optimized Tracking and Updating for Events having Combined Activity and Location Information", which is hereby incorporated by reference in its entirety.

This application is related to U.S. patent application Ser. No. 13/959,698, filed on Aug. 5, 2013, and titled "Methods and Systems for Classification of Geographic Locations for Tracked Activity", which is hereby incorporated by reference in its entirety.

FIELD

The present disclosure relates to systems and methods for processing social interactive data and sharing of tracked activity associated with locations.

BACKGROUND

In recent years, the need for health and fitness has grown tremendously. The growth has occurred due to a better understanding of the benefits of good fitness to overall health and wellness. Unfortunately, although today's modern culture has brought about many new technologies, such as the Internet, connected devices and computers, people have become less active. Additionally, many office jobs require people to sit in front of computer screens for long periods of time, which further reduces a person's activity levels. Furthermore, much of today's entertainment options involve viewing multimedia content, computer social networking, and other types of computer involved interfacing. Although such computer activity can be very productive as well as entertaining, such activity tends to reduce a person's overall physical activity.

To provide users concerned with health and fitness a way of measuring or accounting for their activity or lack thereof, fitness tracker are often used. Fitness trackers are used to measure activity, such as walking, motion, running, sleeping, being inactive, bicycling, exercising on an elliptical trainer, and the like. Usually, the data collected by such fitness trackers can be transferred and viewed on a computing device. However, such data is often provided as a basic accumulation of activity data.

It is in this context that embodiments described herein arise.

SUMMARY

Embodiments described in the present disclosure provide systems, apparatus, computer readable media, and methods for segmenting a period of time into identification of locations of a user performing activities. This segmentation provides a way of identifying particular activities to particular locations. Using the segmentations, the systems and methods can identify one or more events that may have occurred during the period of time of activity. In one embodiment, the events can be displayed on a screen of a device, and a user is able to interactively view data concerning the events with contextual information, e.g., where certain events occurred.

In one embodiment, as described below, the events are automatically associated with locations, and the locations can be associated with contextual information concerning the locations. For instance, if a tracking device detects certain activity at a particular location (e.g., a map location), the mapping data or related databases can be queried to determine that the map location corresponds to a golf course. The system can then generate information that is graphically presented to the user, concerning the particular tracked activity as corresponding to golfing. In some embodiments, the locations can be identified over time, e.g., by received user feedback (e.g., this is my home, this is a coffee shop, this is my work).

In some embodiments, the locations can be inferred or learned based on the activities and times of day, and/or repeat activities over a period of time (e.g., based on an identifiable pattern). For example, if the user/tracker is typically experiencing low activity from 9:00 am and 11:55 am, Monday-Friday, it can be inferred using a rules database and learning logic that the user is at work or is working. In another embodiment, the user can be asked, "are you at work?" via a computing device or a tracking device, and based on the user's response, a database can associate particular locations (e.g., geo-location) to a particular actual location (e.g., work), and collect the activity data for presentation along with the most appropriate location.

In some embodiments, an activity that is performed by a user is inferred based on geo-locations of a monitoring device or a computing device used by the user. For example, a processor of the monitoring device, of the computing device, of a server, or of a virtual machine determines based on the geo-locations that a user is at a location, e.g., a gym, home, work, etc. The processor retrieves from an activity-location database one or more activities that may be performed by the user at the location. For example, the activity-location database indicates that the user may be performing one or more activities, e.g., using a treadmill, using an elliptical trainer, lifting weights to build resistance, swimming laps, etc., while at a gym. As another example, the activity-location database indicates that the user may be performing one or more activities, e.g., walking, climbing stairs, descending stairs, sleeping, etc., while at home. The processor retrieves one or more of the activities from the activity-location database that correspond to the location and determines that the user is performing one or more of the activities.

Broadly speaking, the systems and methods facilitate determination of an activity level of an activity performed by a user at a location. For example, the systems and methods can determine that the user is sedentary for a particular period of time when the user is at work. As another example, the systems and methods can determine that the user is active when the user is at home. The activity or lack of activity is therefore contextually associated to a particular location. The systems and methods determine activity levels of one or more activities performed by the user during a period of time. The user can view the activity levels of an activity performed at a location and decide whether to perform a different activity at the location, to perform an activity at another location, or to continue performing the activity when at the location. By providing the user location context to activities, the user is able to better view his or her actual activity performance and better health decisions can be made regarding and/or adjustments can be made in lifestyle. For instance, a user may find that walking to the train station can significantly improve his/her health, over taking a bus to the train. These simple decisions in activity can act to significantly increase a person's activity, but providing context as to what and where activity is taking place can provide better understanding as to how simple changes can have large impacts in overall fitness.

In some embodiments, a method includes determining a location of a first monitoring device used while performing an activity. The first monitoring device is configured to be worn by a first user. The method includes determining a location of a second monitoring device used while performing an activity. The second monitoring device is configured to be worn by a second user. The method further includes determining whether the location of the first monitoring device is within a threshold distance of the location of the second monitoring device and determining whether the activity performed using the first monitoring device is similar to the activity performed using the second monitoring device. The method includes sending a notification to the first monitoring device upon determining that the activity performed using the first monitoring device is similar to the activity performed using the second monitoring device and that the location of the first monitoring device is within the threshold distance of the location of the second monitoring device. The notification includes a request for permission from a first user account of the first user to allow a second user account of the second user to access information from the first user account regarding the activity performed using the first monitoring device.

In some embodiments, a method includes determining a location of a first monitoring device used while performing an activity. The first monitoring device is configured to be worn by a first user. The method includes determining a location of a second monitoring device used while performing an activity. The second monitoring device is configured to be worn by a second user. The method includes determining whether the location of the first monitoring device is within a defined distance range of the location of the second monitoring device. The method includes determining an activity level of the activity performed using the first monitoring device when the location of the first monitoring device is within the defined distance range of the location of the second monitoring device. The method includes determining whether the activity level is below a threshold and sending a recommendation to the first monitoring device upon determining that the activity level is below the threshold.

In various embodiments, a method includes determining a location of a first monitoring device used while performing an activity. The first monitoring device is configured to be worn by a first user. The method includes determining a location of a second monitoring device used while performing an activity. The second monitoring device is configured to be worn by a second user. The method further includes determining whether the location of the first monitoring device is within a threshold distance of the location of the second monitoring device. The method includes sending a prompt to the first monitoring device upon determining that the locations of the first monitoring device is within a defined distance range of the location of the second monitoring device. The prompt includes a request for permission from a first user account of the first user to allow a second user account of the second user to access information from the first user account regarding the activity performed using the first monitoring device.

In some embodiments, a system includes a first monitoring device for use by a first user, a second monitoring device for use by a second user, and a processor for determining a location of the first monitoring device used while an activity is performed using the first monitoring device. The processor determines a location of the second monitoring device used while an activity is performed using the second monitoring device. The processor determines whether the location of the first monitoring device is within a threshold distance of the location of the second monitoring device. The processor further determines whether the activity performed using the first monitoring device is similar to the activity performed using the second monitoring device. The system includes a network interface controller for sending a notification to the first monitoring device upon receiving a determination from the processor that the activity performed using the first monitoring device is similar to the activity performed using the second monitoring device and that the locations of the first monitoring device is within the threshold distance of the second monitoring device. The notification includes a permission request from a first user account of the first user to allow a second user account of the second user to access information from the first user account regarding the activity performed using the first monitoring device.

Other aspects will become apparent from the following detailed description, taken in conjunction with the accompanying drawings, illustrating by way of example the principles of embodiments described in the present disclosure.

BRIEF DESCRIPTION OF THE DRAWINGS

Various embodiments described in the present disclosure may best be understood by reference to the following description taken in conjunction with the accompanying drawings in which:

FIG. 5 is a block diagram of a computing device, in accordance with one embodiment described in the present disclosure.

FIG. 7C is a diagram illustrating a method for establishing boundaries between two locations arrived at by a user over one or more periods of time, in accordance with one embodiment described in the present disclosure.

FIG. 7O is a diagram of a GUI that includes an overlay of a map on one or more locations that a user visits during a period of time to perform one or more activities performed by the user during a period of time, in accordance with one embodiment described in the present disclosure.

DETAILED DESCRIPTION

Figure 1A:
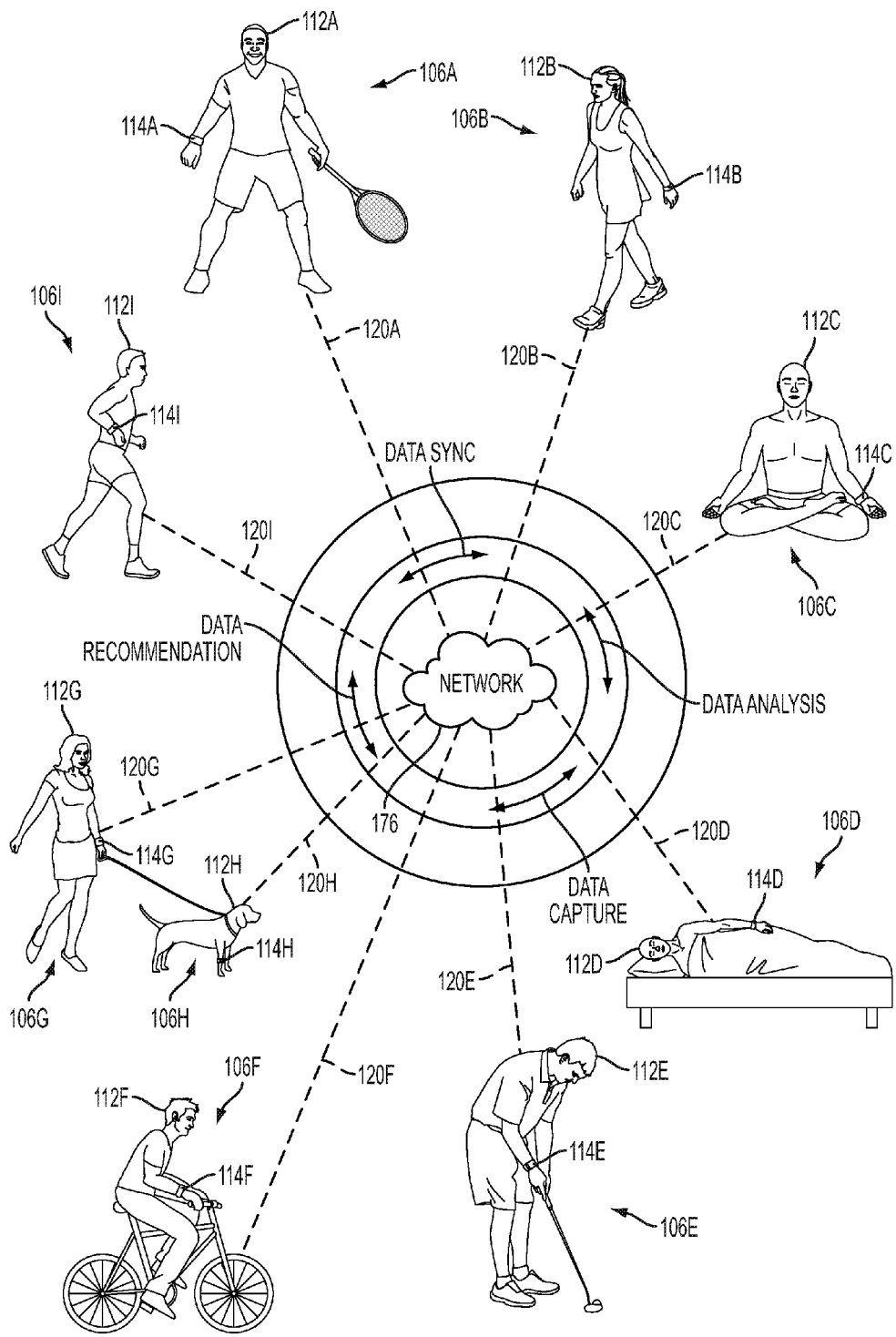
FIG. 1A illustrates a variety of situations in which a system for segmenting a period of time into identification of locations of a user performing activities is used, in accordance with one embodiment described in the present disclosure.

Embodiments described in the present disclosure provide systems, apparatus, computer readable media, and methods for analyzing tracked activity data and segmenting/associating the activity data to contextually identifiable locations where a user, wearing an activity tracker performed such activities. This segmentation provides a way of identifying events that associate the identified activities to particular locations. In one embodiment, the data is collected from an activity tracker and then transferred to a computing device. In some embodiments, the computing device can include a portable device, such as a smart phone, an internet connected watch, a tablet, a laptop, a desktop, etc. The computing device can then transfer the collected activity data to a server that is connected to the internet for processing.

In one embodiment, the term location refers to a geographic position. The geographic position can be identified on a map, identified on a coordinate identifier using global positioning data (e.g., GPS), identified using radio signal tower locator data (e.g., cell towers), identified using wireless internet router signal data (e.g., Wi-Fi signals), identified using router signal data for multi-floor identification (e.g., floor-to-floor locator data), or combinations thereof. In some embodiments, changes in location data include determining a difference between location identified data at various times (e.g., every minute, every few minutes, every half hour, every hour, at particular hour intervals or days). In some embodiments, the time at which location data is obtained can vary depending on sensed activity. For example, if less activity or motion is detected, fewer location data points need be taken.

The server can include one or more servers, which define a cloud processing system. The cloud processing system includes logic, code, programs and/or software for processing the activity data to produce the identifiable events. The cloud processing system can provide a system for creating user accounts for users and their activity trackers. The user accounts enable users to view graphical users interfaces (GUIs) that render and display the events identified using the tracked activity data and the location data (e.g., geo-location data). Processing logic on the servers associated with the cloud processing system can process the tracked data, can access other Internet services (e.g., mapping services, social networking services, location context services, etc., to enable formulation or identification of a location for particular activities, which define an event). Broadly speaking, an event is defined to include a location and an activity.

In one embodiment, the events can be displayed on a screen of a device, and a user is able to interactively view data concerning the events with contextual information, e.g., where certain events occurred.

In some embodiments, locations can be automatically identified by accessing mapping services and other online databases that identify locations. The online databases can include mapping programs, data from social networks, tagged data, crowd-sourced data, etc.

In some embodiments, the locations can be inferred or learned based on the activities and times of day, and/or repeat activities over a period of time (e.g., based on an identifiable pattern). Databases of rules are constructed and such rules are refined over time. The rules are used to enable the system to infer locations and provide appropriate contextual identification to the locations. In some embodiments, the rules can shape themselves using learning systems, and can be tailored for specific users. In still other embodiments, learned patterns and behaviors of other users can be used to collaboratively identify rules, shape rules or determine locations or identify locations. For instance, if multiple users tag a location as a coffee bar, this information can be used to associate "coffee bar" to some range of geo-location. If over time, the location starts to get tagged as a breakfast bar, the rules can be adjusted to now associate that geo-location as "breakfast bar." As businesses or location contexts change over time, so can the rules.

In various embodiments, the shape rules are used to associate one or more geo-locations with a location. For example, a shape, e.g., a circle, a polygon, an oval, a square, etc., is used to identify a location on a graphical user interface. The graphical user interface may include event data, a route, a map, or a combination thereof. A user changes a size via a user interface of a monitoring device or via an input device of a computing device of a shape to change a number of geo-locations associated with the location. For example, a user increases a size of a circle to include more geo-locations within a location that is identified by the circle. As another example, a user decreases a size of a polygon to exclude a number of geo-locations from within a location that is identified by the polygon. As another example, a center of a shape is changed to associate a different set of geo-locations with a location than that already associated with the location. For example, a user drags via a user interface of a monitoring device or via an input device of a computing device a point associated with, e.g., a center of, a vertex of, etc., a shape to a different spot on a graphical user interface. When the point is dragged, the shape is also dragged to the difference spot and is associated with a difference set of geo-locations than that before the movement of the center. The graphical user interface may include event data, a route, a map, or a combination thereof.

In another embodiment, the user may be allowed to post details of particular locations. The user can identify locations with particular custom identifiers, e.g., "mom's house" or can select from predefined identifiers. In still other embodiments, the user can be asked to identify a location. In still another embodiment, the user can be asked via custom queries, such as: "Are you at work?"; "Is this your home?"; "Are you driving?"; "Do you need medical assistance? if so, say or type help" etc. Or, the queries can be presented to the user at a later time, such as when the user is viewing his or her past activity on a GUI. In some embodiments, the queries can be provided via a cloud program, when accessing a computer with cloud access, via push notifications, via voice requests, etc. Based on this returned feedback, the servers and databases of the cloud service can learn or associate location identification to particular locations, which are later identified by detecting the geo-location of the tracker.

In some embodiments, a user tags a location as being associated with a person known to the user. For example, a user logs into his/her user account and tags a location as being Mom's house, Eric's house, Jessica's house, Buddy's gym, etc. Examples of a person known to the user include a friend of the user, a work mate of the user, a special interest of the user, a relative of the user, an acquaintance of the user, or a family member of the user. The user tags via an input device of a computing device or via an user interface of a monitoring device. A processor, e.g., a processor of the monitoring device, a processor of the computing device, a processor of a server, a processor of a virtual machine, or a combination thereof, etc., determines that the tag indicates that the user knows the person. For example, the term "Mom" indicates that the person is a mom of the user. As another example, "Eric" indicates that the person is a friend, a relative, or an acquaintance of the user. The processor determines whether the person tagged has a user account. The user account is used to display event data that includes activities performed by the person and/or locations visited by the person while performing the activities, etc. The processor suggests to the user to add the person to a social group, e.g. a friend group, a work mate group, a special interest group, a relative group, an acquaintance group, a family member group, etc. When the user adds the person within the social group, the user account of the user indicates the addition of the person within the social group.

In general, the systems and methods facilitate determination of an activity level of an activity performed by a user at a location. For example, the systems and methods can determine that the user is sedentary for a particular period of time when the user is at work. As another example, the systems and methods can determine that the user is active when the user is at home. The activity or lack of activity is therefore contextually associated to a particular location. The location can be an address, map, or a combination of maps, addresses, activities, and/or predefined location identifiers or activities that occur at particular locations (e.g., golf occurs at a golf course, swimming occurs at a swimming pool, etc.). By providing the user location context to activities, the user is able to better view his or her actual activity performance and better health decisions can be made regarding and/or adjustments can be made in lifestyle.

In some instances, well known process operations have not been described in detail in order not to unnecessarily obscure various embodiments described in the present disclosure.

FIG. 1A illustrates a variety of situations/activities in which a system and/or method uses location data to segment a period of time into identifiable events, each event defining an activity for a period of time. In one embodiment, location data is obtained for a time when the activity is tracked, such as location data and/or characteristics of the activity used to identify an event. As noted in detail below, a period of time having associated tracking data can be segmented into one or more events.

In the example of FIG. 1A, a user 112A wears a monitoring device 114A on his arm while playing a sport, e.g., tennis. Other examples of a sport include badminton, golf, running, bicycling, vehicle racing, racquetball, squash, soccer, etc. It should be understood that the example of sports is provided, as such sports have particular identifiable activity patterns. However, any activity, whether sports related or not, can be tracked and associated to an event. For instance, another user 112B wears a monitoring device 114B on her arm while walking. Yet another user 112C wears a monitoring device 114C on his/her arm while doing yoga. Another user 112D wears a monitoring device 114D on his/her arm during sleep. Another user 112E wears a monitoring device 114E on his/her arm while playing golf. Yet another user 112F wears a monitoring device 114F on his/her clothing part while riding a bicycle. Another user 112G wears a monitoring device 114G on his/her foot while walking a user 112H, e.g., a dog. In some embodiments, the user 112G walks other animals, e.g., a tiger, a cat, etc. The user 112H also wears a monitoring device 114H on its arm. Another user 112I wears a monitoring device 114I on his arm during running.

In some embodiments, a user performs one or more of other activities, e.g., swimming, resistance training, rock climbing, skiing, snowboarding, hiking, skating, rollerblading, etc. It is noted that the activities described herein are not limiting and that other activities may be used.

It should be noted that in some embodiments, a user can wear, hold, append, strap-on, move, transport or carry a monitoring device while performing any type of activity, e.g., playing ping-pong, climbing stairs, descending stairs, hiking, sitting, resting, working, etc. Additionally, one user can be associated with more than one monitoring device, and such data can be processed and associated to the user's activity. In some embodiments, the data is selected from various devices of the user based on a priority algorithm. In some embodiments, data from more than one device can be blended or alternated together to define a more complete map of the activities.

Each monitoring device 114A, 114B, 114C, 114D, 114E, 114F, 114G, 114H, and 114I communicates with a network 176. In some embodiments, each monitoring device 114A, 114B, 114C, 114D, 114E, 114F, 114G, 114H, and 114I communicates with the network 176 via a computing device, e.g., a desktop computer, a laptop computer, a smart phone, a tablet, a smart watch, a smart television, etc.

Examples of the network 176 include the Internet and an Intranet. The network 176 may be a wide area network, a local area network, or a combination thereof. The network 176 may be coupled to one or more servers, one or more virtual machines, or a combination thereof.

A server, a virtual machine, a controller of a monitoring device, or a controller of a computing device is sometimes referred to herein as a computing resource. Examples of a controller include a processor and a memory device.

As used herein, a processor includes an application specific integrated circuit (ASIC), a programmable logic device (PLD), a processor, a central processing unit (CPU), or a combination thereof, etc. Examples of a memory device include a random access memory (RAM) and a read-only memory (ROM). A memory device may be a Flash memory, a redundant array of disks (RAID), a hard disk, or a combination thereof.

A computing resource performs data capture, which is reception of activity data from a monitoring device. Examples of activity data include, without limitation, calories burned by a user, blood pressure of the user, heart rate of the user, weight gained by a user, weight lost by a user, stairs ascended, e.g., climbed, etc., by a user, stairs descended by a user, steps taken by a user during walking or running, floors descended by a user, floors climbed by a user, a number of rotations of a bicycle pedal rotated by a user, sedentary activity data, a distance covered by a user during walking, running, or driving a vehicle, a number of golf swings taken by a user, a number of forehands of a sport played by a user, a number of backhands of a sport played by a user, or a combination thereof. In some embodiments, sedentary activity data is referred to herein as inactive activity data or as passive activity data. In some embodiments, when a user is not sedentary and is not sleeping, the user is active.

The data capture also includes capturing a geo-location of a monitoring device. For example, geographical location data 120A of the monitoring device 114A is determined by the monitoring device 114A and obtained by a computing resource. A geo-location is determined by a device locator, which is further described below. Examples of a geo-location include latitude, radius, longitude, altitude, landmark, city, country, state, county, village, eatery, commercial place, commercial building, province, public place, or a combination thereof. In some embodiments, the geo-location data is obtained not by the monitoring device, but by a companion device (e.g., such as a smart phone or other portable device with global positioning system (GPS) data collection capabilities).

In various embodiments, a device locator obtains a speed of a monitoring device or of a computing device. For example, a device locator of a computing device determines a speed of the computing device and a device locator of a monitoring device determines a speed of the monitoring device. In various embodiments, a device locator of a device, e.g., a monitoring device, a computing device, etc., obtains an orientation of the device. In various embodiments, an orientation of a device includes a degree of rotation of the device with respect to an x axis, a y axis, and a z axis.

Similarly, geographical location data 120B of the monitoring device 114B is determined by the monitoring device 114B and obtained by a computing resource, geographical location data 120C of the monitoring device 114C is determined by the monitoring device 114C and obtained by a computing resource, geographical location data 120D of the monitoring device 114D is determined by the monitoring device 114D and obtained by a computing resource, geographical location data 120E of the monitoring device 114E is determined by the monitoring device 114E and obtained by a computing resource, geographical location data 120F of the monitoring device 114F is determined by the monitoring device 114F and obtained by a computing resource, geographical location data 120G of the monitoring device 114G is determined by the monitoring device 114G and obtained by a computing resource, geographical location data 120H of the monitoring device 114H is determined by the monitoring device 114H and obtained by a computing resource, and geographical location data 120I of the monitoring device 114I is determined by the monitoring device 114I and obtained by a computing resource.

A geo-location of a monitoring device is used in conjunction with activity data by a computing resource to perform data analysis. The data analysis is performed by a processor. For example, a level, e.g., an amount, etc., of an activity performed by a user at a geo-location is determined. Examples of activity level include a number of calories burned by a user, an amount of weight gained by a user, a heart rate of a user, an amount of blood pressure of a user, an amount of weight lost by a user, a number of stairs ascended by a user, a number of stairs descended by a user, a number of steps taken by a user during walking or running, a number of floors descended by a user, a number of floors climbed by a user, a number of rotations of a bicycle pedal rotated by a user, a distance covered by a vehicle operated by a user, a number of golf swings taken by a user, a number of forehands of a sport played by a user, a number of backhands of a sport played by a user, or a combination thereof, etc. The geo-location and the activity level are combined and displayed to a user to monitor activity and/or health of the user over a period of time. As another example, a geo-location is combined with an activity level to determine whether a user is still at a location, e.g., a house, a work place, an office, a gym, a sandwich shop, a coffee shop, etc. after performing the activity or has left the location after performing the activity. In this example, when it is determined that the user is at the location and the activity level has crossed from a first side of a threshold to a second side of the threshold, it is determined that the user has left the location. Moreover, in this example, when it is determined that the user is at the location and that the activity level has not crossed from the first side to the second side, it is determined that the user is still at the location. In some embodiments, the first side of the threshold is below the threshold and the second side of the threshold is above the threshold. In various embodiments, the first side of the threshold is above the threshold and the second side is below the threshold.

In some embodiments, a user indicates to a monitoring device or a computing device that the user has exited or entered a location. For example, the user logs into a user account and indicates via a user interface of a monitoring device or an input device of a computing device that the user is exiting or entering a location. A processor, e.g., a processor of a server, a processor of a virtual machine, a processor of the computing device, or a processor of the monitoring device, or a combination thereof, etc., receives the indication from the user. The processor determines a time at which the user indicates that the user is entering or exiting the location and indicates the time on a graphical user interface that includes event data. In various embodiments, upon determining that the user has entered a location, the processor accesses the activity-location database to determine one or more activities that may be performed by the user at the location and generates one or more activity identifiers of the activities.

In some embodiments, a computing resource performs data synchronization, which includes synchronization of activity data received from various users and synchronization of geo-locations of the users. For example, activity data from one user is displayed to another user when both the users are within one location. As another example, activity data of one user is displayed to another user when both users are performing the same activity, e.g., walking, running, etc. As yet another example, activity data of one user is displayed to another user when both users are performing the same activity at the same location. As another example, activity data is displayed to two or more users who perform similar activities in disparate locations (e.g., a virtually shared walk).

In various embodiments, a computing resource recommends data to a user based on activity data received from a monitoring device used by the user and based on a location of the user. For example, when it is determined that a user is at a golf course and has not taken a number of golf swings, the recommendation data indicates to the user that the user may take an additional amount of golf swings to achieve a goal. As another example, when it is determined that a user is not going to (or is unlikely to based on knowledge of the user's historical activity patterns) reach his/her activity goal, e.g., walking a number of steps over a time period, running a distance over a time period, climbing or descending a number of stairs over a time period, bicycling for an amount of distance over a time period, bicycling for a number of pedal rotations of a bicycle over a time period, lifting a weight for a number of times over a time period, hitting a forehand for a number of times over a time period, hitting a backhand for a number of times over a time period, etc., and it is determined that the user is at a location, the computing resource generates the recommendation data to indicate to the user to perform an activity or to extend performing the activity at the location or at another location that is within a distance of the location. These recommendations can be provided as electronic notifications to the user's device, the user's smart phone, to the tracking device, or some other user interface. The recommendations can also be provided as voice notifications, in case the user is occupied in a task that limits viewing a screen, such as driving. The determination that the user is driving can be made using data regarding the speed/motion of the device, location data (e.g., in a car), etc.

In some embodiments, a user may stand on a monitoring device that determines a physiological parameter of the user. For example, a user stands on a scale that measures a weight, a body fat percentage, a biomass index, or a combination thereof, of the user.

Figure 1B:
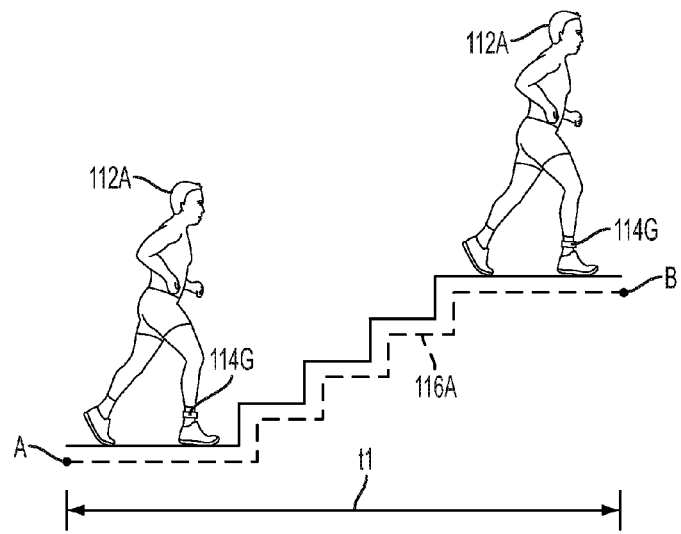
FIG. 1B is a diagram of a method for determining an amount of a type of movement of a monitoring device over a period of time, in accordance with one embodiment described in the present disclosure.

FIG. 1B is a diagram of an embodiment of a method for determining an amount of movement 116A of the monitoring device 114G, e.g., a number of stairs ascended by the monitoring device 114G, etc., over a period of time t1. The amount of movement 116A occurs when the user 112A is performing an activity of climbing stairs over the time period t1. A method of determining an amount of movement is performed by a position sensor of a monitoring device. Additionally, the method can simultaneously identify a location for the activity. The monitoring device 114G may be worn on the leg or foot (as depicted in FIG. 1B), or elsewhere on the body such as the wrist, forearm, upper arm, head, chest, or waist, or as an article of clothing such as a shirt, hat, pants, blouse, glasses, and the like.

A position sensor determines an amount of linear or angular movement of an arm of a user or of another body part of a user. For example, a position sensor determines that the user 112A wearing the monitoring device 114G on his leg has climbed a number of stairs, e.g., four, twenty, forty, etc., between positions A and B over the time period t1.

In some embodiments, instead of a number of stairs ascended, a position sensor determines a number of stairs descended by the monitoring device 114G.

Figure 1C:
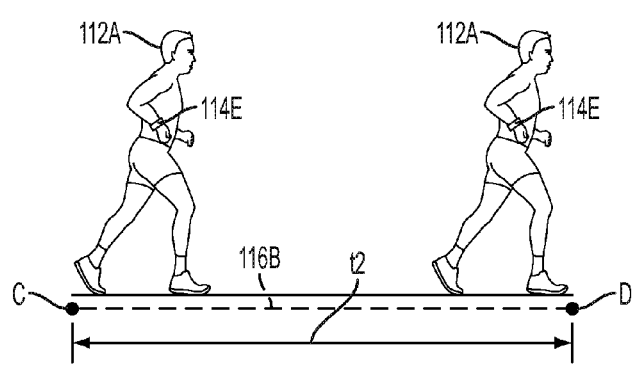
FIG. 1C is a diagram of a method for determining an amount of another type movement of a monitoring device over a period of time, in accordance with one embodiment described in the present disclosure.

FIG. 1C is a diagram of an embodiment of a method for determining an amount of movement 116B, e.g., an amount of distance traveled, a number of steps traveled, etc., of the monitoring device 114E over a period of time t2. For example, a position sensor determines that the user 112A wearing the monitoring device 114E on his hand has walked or ran a number of steps, e.g., four, fifty, hundred, etc., between positions C and D over the time period t2. The amount of movement 116B occurs when the user 112A is performing an activity of walking or running over the time period t2.

Figure 1D:
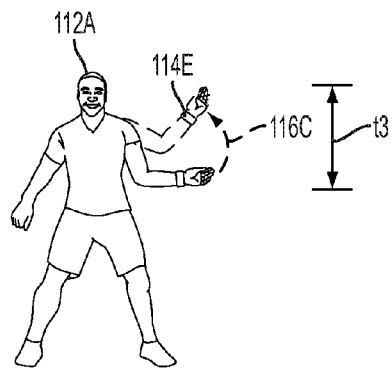
FIG. 1D is a diagram of a method for determining an amount of yet another type movement of a monitoring device over a period of time, in accordance with one embodiment described in the present disclosure.

FIG. 1D is a diagram of an embodiment of a method for determining an amount of movement 116C, e.g., an amount angular movement, etc., of the monitoring device 114E over a period of time t3. For example, a position sensor determines that a hand of the user 112A wearing the monitoring device 114E on his/her hand is displaced by an angle over the time period t3. The amount of movement 116C occurs when the user 112A is performing a sports activity, e.g., golfing, playing tennis, playing ping-pong, resistance training, etc., over the time period t3.

In some embodiments, a position sensor measures an angular displacement of a leg of the user 112A wearing the monitoring device 114G on his leg.

In various embodiments, a position sensor infers an activity performed by a user over a period of time based on one or more positions of a monitoring device that has the position sensor and that is worn by the user. For example, upon determining that a difference between a first y position and a second y position within a xyz co-ordinate system is greater than an amount and that x positions between the two y positions indicate a curved movement, a position sensor of a monitoring device determines that the user 112A is playing golf. As another example, upon determining that the user 112A covers less than a distance along an x-axis over a period of time, a position sensor of a monitoring device worn by the user 112A determines that the user 112A is walking and upon determining that the user 112A covers more than the distance along the x-axis over the period of time, the position sensor determines that the user 112A is running.

Figure 1E:
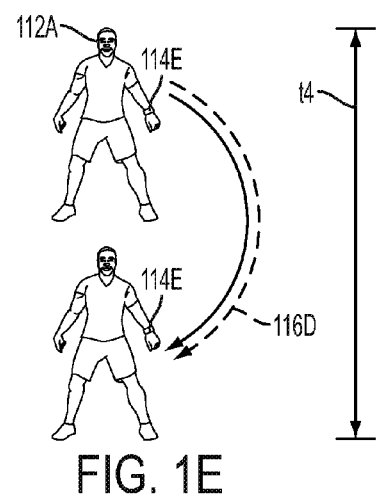
FIG. 1E is a diagram of a method for determining an amount of another type movement of a monitoring device over a period of time, in accordance with one embodiment described in the present disclosure.

FIG. 1E is a diagram of an embodiment of a method for determining an amount of movement 116D, e.g., an amount angular movement, etc., of the monitoring device 114E over a period of time t4. For example, a position sensor determines that the user 112A wearing the monitoring device 114E on his/her hand is displaced by an angle over the time period t4. The amount of movement 116D occurs when the user 112A is performing an activity, e.g., a sports activity, an exercise activity, etc., over the time period t4.

Examples of a period of time include a portion of a day, or a day, or a portion of a month, or a month, or a portion of a year, or a year, or a portion of a number of years, or a number of years.

Figure 2A:
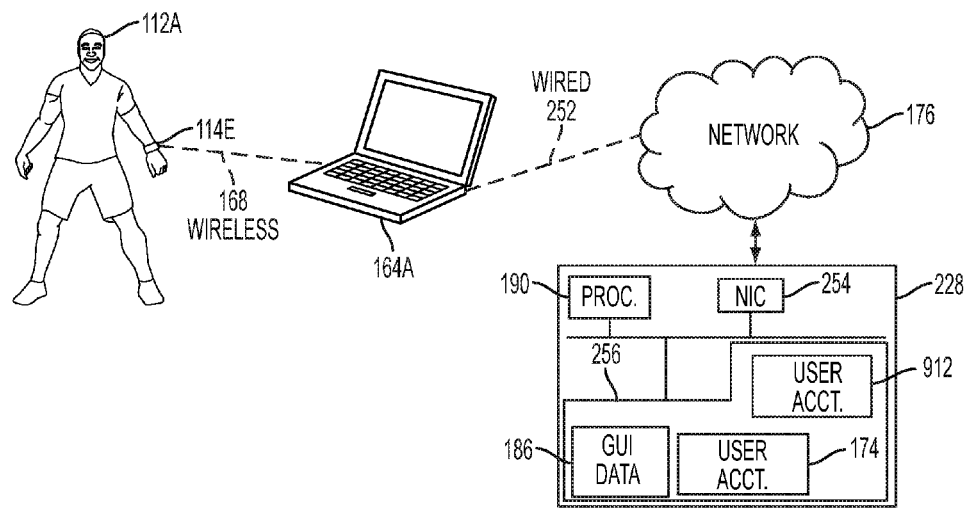
FIG. 2A is a diagram of a system for transferring data between a monitoring device and a server via a computing device and a network, in accordance with one embodiment described in the present disclosure.

FIG. 2A is a diagram of an embodiment of a system 250 for transferring data, e.g., activity data, geo-location data, etc., between the monitoring device 114E and a server 228 via a computing device 164A and the network 176. A wireless link 168 establishes a connection between the monitoring device 114E and the computing device 164A. For example, a Bluetooth device located within the monitoring device 114E establishes a Bluetooth connection with a Bluetooth dongle interfacing with the computing device 164A via a Universal Serial Bus (USB) interface. As another example, an ad hoc Wi-Fi transmission and reception is established between a Wi-Fi adapter of the monitoring device 114E and a Wi-Fi adapter of the computing device 164A. The wireless link 168 may be a Bluetooth or a Wi-Fi connection. A connection between the monitoring device 114E and the computing device 164A is used to transfer data between the monitoring device 114E and the computing device 164A.

In some embodiments, a geo-location and/or a position determined by the monitoring device 114E is sent from the monitoring device 114E via the computing device 164A to a server or a virtual machine for processing, e.g., analysis, determining event data, etc. The server or the virtual machine processes the geo-location and/or the position and sends processed data, e.g., event data, maps, routes, etc., to the computing device 164A for display on the computing device 164A.

In some embodiments, instead of the wireless link 168, a wired connection is used between the monitoring device 114E and the computing device 164A.

Moreover, a wired connection 252 is established between the computing device 164A and the server 228 via the network 176. A wired connection includes network components, e.g., one or more routers, one or more switches, one or more hubs, one or more repeaters, one or more servers, one or more cables, or a combination thereof, etc.

The server 228 includes a processor 190, a network interface controller (NIC) 254 and a memory device 256. The processor 190 is coupled with the memory device 256 and the NIC 254. An example of a NIC includes a network interface card. In some embodiments, a modem is used instead of a NIC.

The memory device 256 includes a user account 174 of the user 112A. The user 112A accesses the user account 174 when authentication information, e.g., username, password, fingerprints, footprints, thumbprints, or a combination thereof, etc., is authenticated by the processor 190 or another server of the network 176. The authentication information is provided by the user 112A via an input device, e.g., a mouse, a stylus, a keyboard, a keypad, a button, a touch screen, or a combination thereof, etc., of a monitoring device or of a computing device.

The user account 174 is accessed by the user 112A to review graphical user interface (GUI) data 186 on a display device of the computing device 164A or of the monitoring device 114E. The GUI data 186 includes geo-location data, a map, location in the form of location/activity identifiers, activity data in the form of activity levels, and/or physiological parameter of the user 112A. The activity data represents activities performed by the monitoring device 114E. The processor 190 associates, e.g., links, establishes a relationship between, etc., geo-location data, location, activity data, and/or physiological parameter of the user 112A with the user account 174 to allow access of the geo-location data, activity data, a map, location, and/or physiological parameter upon access of the user account 174. This relationship provides context to the activity, both in terms of what the activity was and where the activity occurred. This context can be used to define events that occur over a period of time, and the events can be presented on a GUI of a device, to provide useful information to a user regarding his or her activity over that period of time. Not only is the user provide with activity data, but the activity data is displayed in a graphical or data organized manner that identifies segmented activity data and associates it to the proper or inferred context.

Similarly, a user account 912 is accessed by the user 112B when authentication information received from the user 112B is authenticated. For example, the user 112B logs into the account 912 when authentication information received from the user 112B via a user interface of the computing device 166 or via an input device of a monitoring device is authenticated. The user account 912 is stored within the memory device 256 of the server 228. The user 112B accesses the user account 912 to review a GUI that includes event data showing activity levels of one or more activities performed by the user 112B.

In some embodiments, instead of using the monitoring device 114E to establish the wireless connection 168, any other monitoring device, e.g. the monitoring device 114A (FIG. 1A) or a monitoring scale is used.

It should be noted that in several embodiments, data is transferred from a monitoring device via a computing device and the network 176 to a virtual machine instead of the server 228.

In some embodiments, instead of the wired connection 252, a combination of a wireless connection and a wired connection is established.

In various embodiments, a user account, e.g., the user account 174, the user account 912, etc., is stored in a memory device of a computing device or on a memory device of a monitoring device. In these embodiments, processing of a geo-location and/or position is not done on the server 228 or a virtual machine to generate processed data, e.g., event data, location identifier, activity identifier, etc. but is done by a processor of the computing device and/or by a processor of a monitoring device to generate the processed data.

Figure 2B:
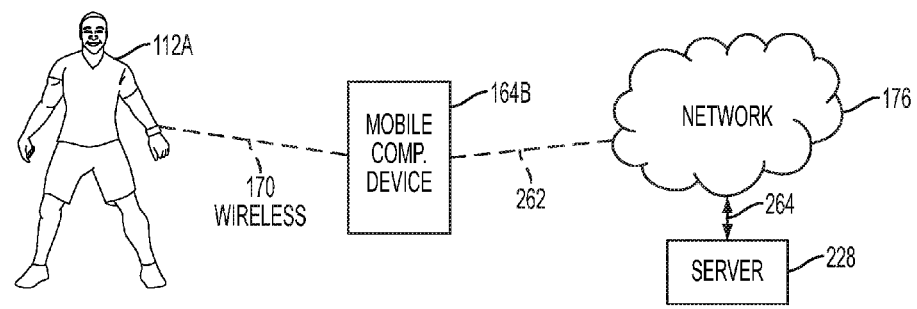
FIG. 2B is a diagram of an embodiment of a system for transferring data between a monitoring device and the server via a mobile computing device and the network, in accordance with one embodiment described in the present disclosure.

FIG. 2B is a diagram of an embodiment of a system 260 for transferring data, e.g., activity data, geo-location data, etc., between the monitoring device 114E and the server 228 via a mobile computing device 164B and the network 176. A wireless link 170 establishes a connection between the monitoring device 114E and the mobile computing device 164B. The wireless link 170 may be a Bluetooth connection, a Wi-Fi connection, a near field connection, a radio frequency connection, or an optical connection, etc. In some embodiments, instead of the wireless link 168, a wired connection is used between the monitoring device 114E and the mobile computing device 164B. A connection is used to transfer data between the monitoring device 114E and the mobile computing device 164B.

Moreover, the server 228 and the mobile computing device 164B are coupled with each other via a wireless connection 262, e.g., a Wi-Fi connection, etc., the network 176, and a connection 264. The connection 264 between the server 228 and the network 176 may be a wired or a wireless connection.

Figure 3A:
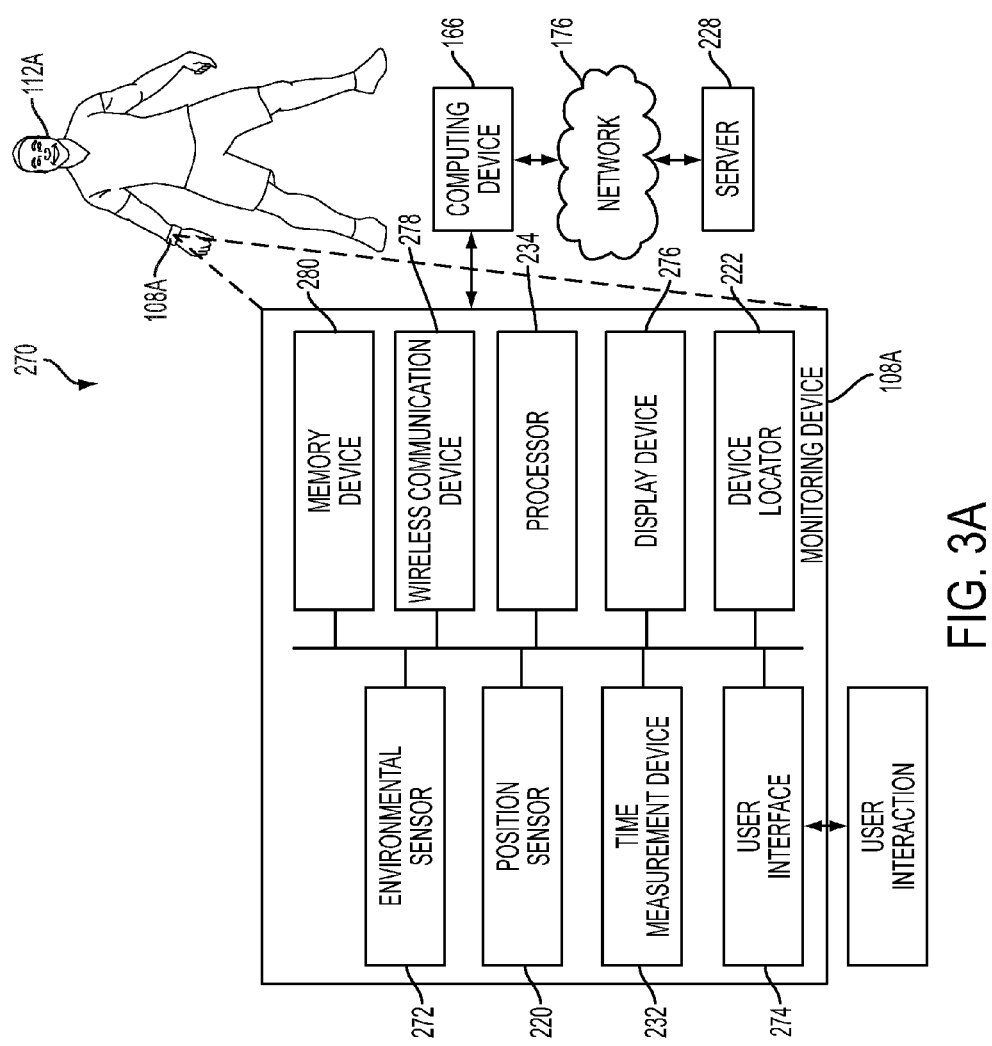
FIG. 3A is a diagram of a system to illustrate components of a monitoring device, in accordance with one embodiment described in the present disclosure.

FIG. 3A is a diagram of an embodiment of a system 270 to illustrate components of a monitoring device 108A. The system 270 includes the monitoring device 108A, a computing device 166, the network 176, and the server 228.

The monitoring device 108A is an example of any of the monitoring devices 114A, 114B, 114C, 114D, 114E, 114F, 114G, 114H, and 114I (FIG. 1A). The monitoring device 108A includes an environmental sensor 272, a position sensor 220, a time measurement device 232, a user interface 274, a device locator 222, a display device 276, a processor 234, a wireless communication device 278, and a memory device 280, all of which are coupled with each other.

Examples of the device locator 222 include a GPS transceiver, a mobile transceiver, etc. As used herein, a device locator may be referred to as a device or circuit or logic that can generate geo-location data. The geo-location data provides the appropriate coordinate location of the device or tracker, such as a location on a map or location in a room or building. In some embodiments, a GPS device provides the geo-location data. In other embodiments, the geo-location data can be obtained from various devices (e.g., cell towers, Wi-Fi device signals, other radio signals, etc., which can provide data points usable to locate or triangulate a location.

Examples of the environmental sensor 272 include a barometric pressure sensor, a weather condition sensor, a light exposure sensor, a noise exposure sensor, a radiation exposure sensor, and a magnetic field sensor. Examples of a weather condition include a temperature, humidity, a pollen count, air quality, rain conditions, snow conditions, wind speed, a combination thereof, etc. Examples of light exposure include ambient light exposure, ultraviolet (UV) light exposure, or a combination thereof, etc. Examples of air quality include particulate counts for varying sized particles, or level of carbon dioxide in air, or level of carbon monoxide in air, or level of methane in air, or level of other volatile organic compounds in air, or a combination thereof.

Examples of the position sensor 220 include an accelerometer, a gyroscope, a rotary encoder, a calorie measurement sensor, a heat measurement sensor, a moisture measurement sensor, a displacement sensor, an ultrasonic sensor, a pedometer, an altimeter, a linear position sensor, an angular position sensor, a multi-axis position sensor, or a combination thereof, etc. In some embodiments, the position sensor 220 measures a displacement, e.g., angular displacement, linear displacement, a combination thereof, etc., of the monitoring device 108A over a period of time with reference to an xyz coordinate system to determine an amount of activity performed by the user 112A during the period of time. In some embodiments, a position sensor includes a biological sensor, which is further described below. In various embodiments, a position sensor includes a motion sensor.

Examples of the time measurement device 232 include a watch, an oscillator, a clock, an atomic clock, etc. Examples of the user interface 274 include an input device for interacting with the user 112A. For example, the user interface 274 receives a selection of the GUI data 186 (FIG. 2A) from the user 112A. It should be noted that when the user interface 274 includes a touch screen, the touch screen 274 is integrated within the display device 276.

Examples of a display device includes a liquid crystal display (LCD) device, a light emitting diode (LED) display device, a plasma display device, etc. As an example, the display device 276 displays the GUI data 186. In some embodiments, all GUIs described herein are displayed by rendering the GUI data 186.

Examples of the memory device 280 are provided above. Examples of the wireless communication device 278 include a Wi-Fi adapter, a Bluetooth device, etc.

In some embodiments, the processor 234 receives one or more geo-locations measured by the device locator 222 over a period of time and determines a location of the monitoring device 108A based on the geo-locations and/or based on one or more selections made by the user 112A via the user interface 274 and/or based on information available within a geo-location-location database of the network 176. For example, the processor 234 determines that a location within the geo-location-location database corresponds to one or more geo-locations stored within the geo-location-location database. In this example, upon receiving the geo-locations from the device locator 222, the processor 234 determines the location based on the correspondence between the geo-locations and the location in the geo-location-location database. In some embodiments, the geo-location-location database includes a map of a geographical region, e.g., a city, a state, a county, a country, a continent, a geographical area, world, etc. The map is generated by the server 228 or another server based on one or more geo-locations.

The environmental sensor 272 senses and determines an environmental parameter, e.g., a barometric pressure, a weather condition, an amount of light exposure, an amount of noise, an amount of radiation, an amount of magnetic field, or a combination thereof, etc., of an environment in which the monitoring device 108A is placed. The device locator 222 determines a geo-location of the monitoring device 108A.

The time measurement device 232 determines an amount of time associated with one or more positions sensed by the position sensor 220, associated with one or more environmental parameters determined by the environmental sensor 272, associated with one or more geo-locations determined by the device locator 222, and/or associated with one or more locations determined by the processor 234. For example, the time measurement device 232 determines an amount of time for a number of positions that is reached by movement of the monitoring device 108A and that is determined by the position sensor 220. As another example, the time measurement device 232 determines an amount of time for a number of geo-locations reached by movement of the monitoring device 108A and that is determined by the device locator 222.

The wireless communication device 278 establishes a wireless link with the computing device 166 to send data, e.g., activity data, geo-location data, location data, a combination thereof, etc., to and/or receive the data and/or instructions from the computing device 166. Each computing device 164A and 164B (FIGS. 2A & 2B) is an example of the computing device 166. The instructions from the computing device 166 may be to send data, e.g., activity data, geo-location data, location data, a combination thereof, etc., to the computing device 166.

In some embodiments, the monitoring device 108A excludes the wireless communication device 278. In these embodiments, the monitoring device 108A communicates using a wired connection with the computing device 166.

In various embodiments, the time measurement device 232 is integrated as a part of the position sensor 220 and/or as a part of the environmental sensor 272 and/or as a part of the device locator 222.

In several embodiments, the monitoring device 108A excludes the environmental sensor 272.

In a number of embodiments, the monitoring device 108A includes a biological sensor coupled to the environmental sensor 272, the position sensor 220, the time measurement device 232, the user interface 274, the device locator 222, the display device 276, the processor 234, the wireless communication device 278, and the memory device 280. The biological sensor is further described below.

Figure 3B:
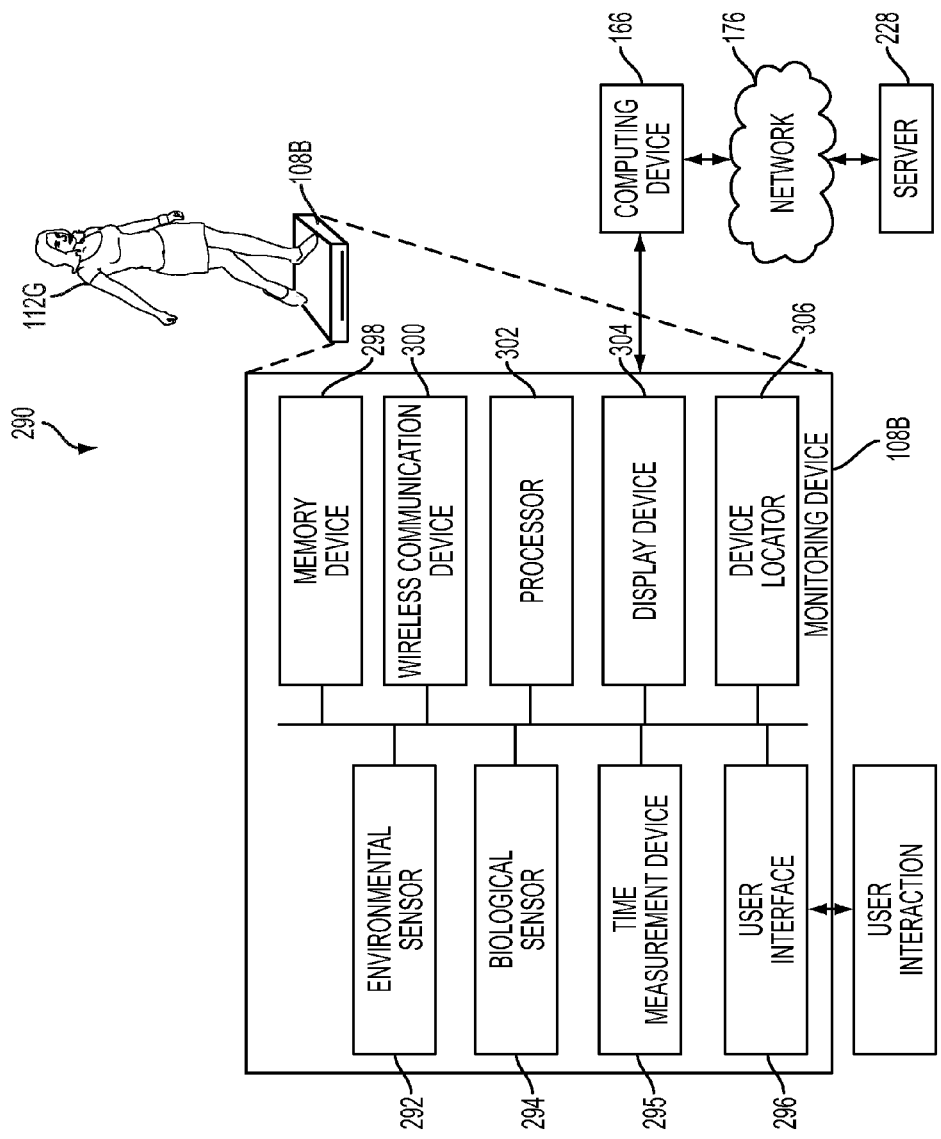
FIG. 3B is a diagram of a system to illustrate components of another monitoring device, in accordance with one embodiment described in the present disclosure.

FIG. 3B is a diagram of an embodiment of a system 290 to illustrate components of a monitoring device 108B. The system 290 includes the monitoring device 108B, the computing device 166, the network 176, and the server 228. An example of the monitoring device 108B includes a scale. The monitoring device 108B is placed on a floor and the user 112A stands on the monitoring device 108B. The monitoring device 108B includes an environmental sensor 292, a biological sensor 294, a time measurement device 295, a user interface 296, a device locator 306, a display device 304, a processor 302, a wireless communication device 300, and a memory device 298.

The environmental sensor 292 performs the same functions as that of the environmental sensor 272 (FIG. 3A) except that the environmental sensor 292 is of a different, e.g., larger, smaller, etc., size compared to a size of the environmental sensor 272. In some embodiments, the environmental sensor 272 is used in the monitoring device 108B instead of the environmental sensor 292.

The biological sensor 294 senses and determines a physiological parameter of the user 112A. For example, the biological sensor 294 determines a weight of the user 112A. As another example, the biological sensor 294 determines a body mass index of the user 112A. As yet another example, the biological sensor 294 determines a fingerprint or a footprint of the user 112A. As another example, the biological sensor 294 determines a heart rate, a hydration level, a body fat, a bone density, and/or a bioimpedance of the user 112A. Examples of the biological sensor 294 include a biometric sensor, a physiological parameter sensor, or a combination thereof.

The time measurement device 295 performs the same functions as that of the time measurement device 232 (FIG. 3A) except that the time measurement device 295 is different, e.g., larger, smaller, etc., in size compared to the time measurement device 232. As an example, the time measurement device 295 determines an amount of time for a number of physiological parameters measured by the biological sensor 294.

In some embodiments, the time measurement device 232 is used in the monitoring device 108B instead of the time measurement device 295.

Similarly, the user interface 296 performs the same functions as that of the user interface 274 (FIG. 3A) and is of a different size than that of the user interface 274. In various embodiments, the user interface 274 is used in the monitoring device 108B instead of the user interface 296.

Moreover, the memory device 298 performs the same functions as that of the memory device 280 (FIG. 3A) and is of a different size than that of the memory device 280. For example, the memory device 298 includes a different, e.g., larger, smaller, etc., number of memory cells compared to memory cells of the memory device 280. In various embodiments, the memory device 280 is used in the monitoring device 108B instead of the memory device 298.

Also, the wireless communication device 300 performs the same functions as that of the wireless communication device 278 (FIG. 3A) and is of a different size than that of the wireless communication device 278. For example, the wireless communication device 300 includes electrical components that allow a transfer data at a different, e.g., higher, lower, etc., rate with the computing device 166 compared to a rate of transfer of data between the wireless communication device 278 and the computing device 166. In various embodiments, the wireless communication device 278 is used in the monitoring device 108B instead of the wireless communication device 300.

Furthermore, the processor 302 performs the same functions as that of the processor 234 (FIG. 3A) and is of a different, e.g., larger, smaller, etc., size than that of the processor 234. For example, the processor 302 is of a size to achieve a different, e.g., higher, lower, etc., speed than that of the processor 234. In various embodiments, the processor 234 is used in the monitoring device 108B instead of the processor 302.

Moreover, the display device 304 performs the same functions as that of the display device 276 (FIG. 3A) and is of a different, e.g., larger, smaller, etc., size than that of the display device 276. In various embodiments, the display device 276 is used in the monitoring device 108B instead of the display device 304.

Also, the device locator 306 performs the same functions as that of the device locator 222 (FIG. 3A) and is of a different, e.g., larger, smaller, etc., size than that of the device locator 222. In various embodiments, the device locator 222 is used in the monitoring device 108B instead of the device locator 306.

In some embodiments, the monitoring device 108B includes a position sensor (not shown) that performs the same functions as that of the position sensor 220 (FIG. 3A). The position sensor of the monitoring device 108B is coupled to the environmental sensor 292, the biological sensor 294, the time measurement device 295, the user interface 296, the device locator 306, the display device 304, the processor 302, the wireless communication device 300, and the memory device 298. In various embodiments, the position sensor 220 is implemented within the monitoring device 108B.

Figure 4A:
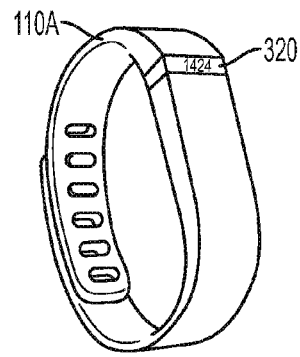
FIG. 4A is an isometric view of a monitoring device that is worn around a hand of a user or around a leg of the user, in accordance with one embodiment described in the present disclosure.

FIG. 4A is an isometric view of an embodiment of a monitoring device 110A that is worn around a hand of a user or around a leg of the user. For example, the monitoring device 110A has a band that is unclasped to allow the monitoring device 110A to extend around a wrist of a user or a leg of the user. After the monitoring device 110A extends around the wrist, the band is clasped to fit the monitoring device 110A to the wrist of the user or to the leg of the user. As another example, the monitoring device 110A has an elastic band that is stretched to allow a grip of the monitoring device 110A to expand. The monitoring device 110A is then slipped around a palm of a user to a wrist of the user or is slipped around a foot of the user to an ankle of the user. The elastic band is then released to fit the monitoring device 110A to the wrist of the user or the ankle of the user. In some embodiments, the monitoring device 110A is worn on a forearm or an upper arm of a user. In other embodiments, the monitoring device can be carried, held, stored in a bag, attached to a shoe, attached to a shirt or pants, etc. In other embodiments, a single person can hold or wear multiple devices. The multiple devices can track the same body part or object or can track/monitor multiple body parts, or objects. For instance, the user can wear one on his/her wrist, one in a shoe, one on his pants, a hat, a visor, or any other object that can track some movement and/or location of the user.

The monitoring device 110A includes a display screen 320 of a display device that displays activity data of one or more activities performed by a user over a period of time, chronological data, geo-location data, or a combination thereof. Examples of a display screen include an LCD screen, an LED screen, a plasma screen, etc. Examples of chronological data include a time of day, a day, a month, a year, etc. The monitoring device 110A is an example of any of the monitoring devices 114A, 114B, 114C, 114D, 114E, 114G, 114H, 114I (FIG. 1A), and 108A (FIG. 3A).

The monitoring device 110A includes one or more input devices that allows a user to switch between displaying different types of data, e.g., from activity data to chronological data, from chronological data to activity data, from one type of activity data to another type of activity data, from geo-location data to activity data, from activity data to geo-location data, etc., and to adjust or set chronological data. Types of activity data include calories burned by a user, weight gained by a user, weight lost by a user, stairs ascended by a user, stairs descended by a user, steps taken by a user during walking or running, floors descended by a user, floors climbed by a user, rotations of a bicycle pedal rotated by a user, distance covered by a vehicle operated by a user, golf swings taken by a user, forehands of a sport played by a user, backhands of a sport played by a user, or a combination thereof, etc.

Again, it should be noted that in some embodiments, the monitoring device 110A is implemented as a watch, a wristband, or a bracelet, that is worn/held by the user 112A.

Figure 4B:
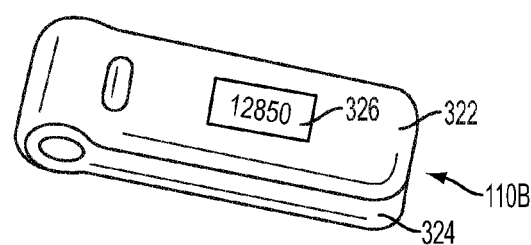
FIG. 4B is an isometric view of another monitoring device that fits to an article of clothing or a belt worn by a user, in accordance with one embodiment described in the present disclosure.

FIG. 4B is an isometric view of an embodiment of a monitoring device 110B that fits to an article of clothing or a belt worn by a user. For example, the monitoring device 110B has a pivoting clip that opens to allow the monitoring device 110B to extend with respect to a pocket of a shirt worn by a user. After the monitoring device 110B extends with respect to the pocket, the clip is retracted to fit the monitoring device 110B to the pocket. The clip may be located between an upper portion 322 and a lower portion 324 of the monitoring device 110B to allow the upper portion 322 to extend from and pivot with respect to the lower portion 324.

The monitoring device 110B includes a display screen 326 that displays activity data, chronological data, geo-location data, or a combination thereof. The monitoring device 110B is an example of the monitoring device 108A (FIG. 3A). The monitoring device 110B includes one or more input devices that allow a user to switch between displaying different types of data and to adjust or set chronological data.

Figure 4C:
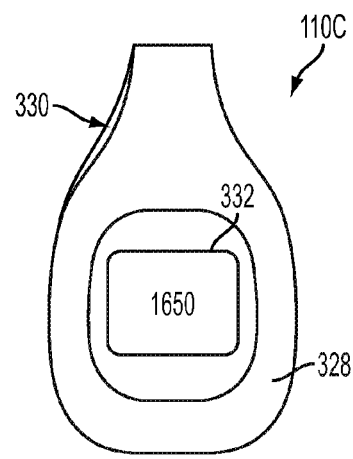
FIG. 4C is a view of yet another monitoring device that fits to an article of clothing or a belt worn by a user, in accordance with one embodiment described in the present disclosure.

FIG. 4C is a view of an embodiment of a monitoring device 110C that fits to an article of clothing or a belt worn by a user. For example, the monitoring device 110C has a flexible pivoting clip that opens to allow the monitoring device 110C to extend with respect to a pocket of a pant worn by a user. After the monitoring device 110C extends around the pocket, the clip is retracted to fit the monitoring device 110C to the pocket. The clip may be located between an upper portion 328 and a lower portion 330 of the monitoring device 110C to allow the upper portion 328 to extend from and pivot with respect to the lower portion 330.

The monitoring device 110C includes a display screen 332 that displays data, e.g., activity data, chronological data, geo-location data, or a combination thereof, etc. The monitoring device 110C is an example of the monitoring device 108A (FIG. 3A). The monitoring device 110C includes one or more input devices that allow a user to switch between displaying different types of data and to adjust or set chronological data.

Figure 4D:
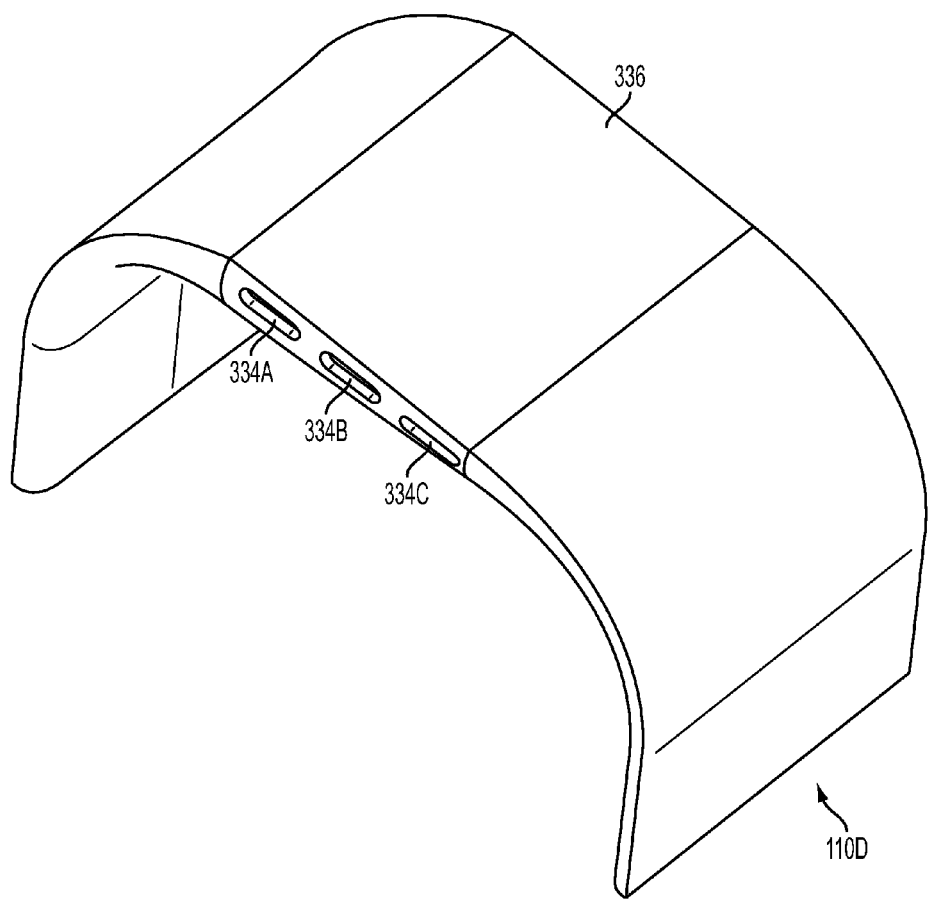
FIG. 4D is an isometric view of another monitoring device that fits to an arm of a user, in accordance with one embodiment described in the present disclosure.

FIG. 4D is an isometric view of an embodiment of a monitoring device 110D that fits with respect to an arm of a user. For example, the monitoring device 110D includes a hook and loop clasp that is extended to loop around a wrist of a user and is then retracted to hook to the wrist. In some embodiments, the monitoring device 110D is implemented within a wrist watch. The monitoring device 110D includes a number of buttons 334A, 334B, and 334C to allow the monitoring device 110D to switch between different types of data, e.g., geo-location data, location, chronological data, activity data, physiological parameter, etc., and to adjust or set chronological data.

The monitoring device 110D includes a display screen 336 that displays activity data, chronological data, geo-location data, physiological parameter, location data, the GUI data 186 (FIG. 2A), or a combination thereof. The monitoring device 110D is an example of any of the monitoring devices 114A, 114b, 114C, 114D, 114E, 114G, 114H, 114I (FIG. 1A), and 108A (FIG. 3A).

It should be noted that in some embodiments, instead of being implemented as a watch, the monitoring device 110D is implemented as a wristband or a bracelet that is worn by the user 112A.

Monitoring devices have shapes and sizes adapted for coupling to, e.g., secured to, worn, etc., the body or clothing of a user. The monitoring devices collect one or more types of physiological and/or environmental data from embedded sensors and/or external devices and communicate or relay the data to other devices, including devices capable of serving as an Internet-accessible data sources, thus permitting the collected data to be viewed, for example, using a web browser or network-based application. For example, while the user 112A is wearing or holding a monitoring device, the monitoring device may calculate and store the user's step count using one or more sensors. The monitoring device then transmits data representative of the user's step count to an account on a virtual machine, a computer, or a mobile phone, where the data may be stored, processed, and visualized by the user 112A.

Indeed, the monitoring device may measure or calculate a plurality of activity data and/or physiological parameters in addition to, or in place of, the user's step count. These activity data and/or physiological parameters include, but are not limited to, energy expenditure, e.g., calorie burn, etc., floors climbed, floors descended, heart rate, heart rate variability, heart rate recovery, geo-location, elevation, speed and/or distance traveled, swimming lap count, swimming stroke type and count detected, bicycle distance and/or speed, blood pressure, blood glucose, skin conduction, skin temperature, body temperature, electromyography, electroencephalography, weight, body fat, caloric intake, nutritional intake from food, medication intake, sleep periods, sleep phases, sleep quality, pH levels, hydration levels, respiration rate, or a combination thereof. The monitoring device may also measure or calculate parameters related to an environment around the user 112A, such as, e.g., barometric pressure, weather conditions (e.g., temperature, humidity, pollen count, air quality, rain/snow conditions, wind speed, etc.), light exposure (e.g., ambient light, UV light exposure, time and/or duration spent in darkness, etc.), noise exposure, radiation exposure, magnetic field, or a combination thereof.

In some embodiments, the monitoring device quantifies work productivity against noise levels and/or against air quality and/or against temperature and/or against pressure and/or against humidity and/or against pollen count and the quantification is identified as a level within event data. In several embodiments, the monitoring device quantifies stress levels against noise levels and/or against an amount of time spent by the user 112A at work and/or against an amount of time spent by the user 112A exercising outside a work location and/or against an amount of time spent by the user 112A in a gym and/or an amount of time spent by the user 112A at his parent's home, and the quantification is identified as a level within event data. In some embodiments, a stress level is quantified, e.g., measured, determined, etc., based on heart rate variability (HRV) and/or galvanic skin response (GSR). The HRV and/or the GSR are measured by a biological sensor.

Furthermore, a monitoring device or a computing device collating data streams may calculate parameters derived from the activity data and/or physiological parameters. For example, monitoring device or a computing device may calculate a user's stress and/or relaxation levels through a combination of heart rate variability, skin conduction, noise pollution, and sleep quality. In another example, a monitoring device or a computing device may determine an efficacy of a medical intervention (e.g., medication) through a combination of medication intake, sleep and/or activity data. In yet another example, the monitoring device or a computing device may determine an efficacy of an allergy medication through the combination of pollen data, medication intake, sleep and/or other activity data.

FIG. 5 is a block diagram of an embodiment of the computing device 166. The computing device 166 includes a processor 226, a memory device 338, an input device 240, an input/output interface (I/O) 342, a device locator 344, a wireless communication device 346, an I/O 348, a graphical processing unit (GPU) 350, a display device 352, an I/O 354, a NIC 356, and an I/O 358, all of which are coupled to each other via a bus 360.

An I/O is a parallel interface, a serial interface, or a USB interface between two devices that are coupled to the I/O. For example, the I/O 358 is an interface between the NIC 356 and the bus 360.

Examples of the processor 226 and the memory device 338 are provided above. Moreover, examples of the input device 340 and the device locator 344 are provided above. Furthermore, examples of the wireless communication device 346, the display device 352, and the NIC 356 are provided above. The GPU 350 executes a rendering technique to display data, e.g., GUI, web page, etc., on the display device 352.

The wireless communication device 346 receives geo-location data and activity data from the wireless communication device 278 (FIG. 3A) of the monitoring device 108A and/or the wireless communication device 300 (FIG. 3B) of the monitoring device 108B. The processor 226 determines a group of activity data and a location/activity identifier based on the activity data and the geo-location data.

In some embodiments, the computing device 166 includes a wired communication device in addition to or instead of the wireless communication device 300. Examples of the wired communication device include a USB interface, a parallel interface, and a serial interface.

In several embodiments, the user 112A provides via the user interface 274 (FIG. 3A) of the monitoring device 108A to the processor 234 or via the input device 340 (FIG. 5) of the computing device 166 to the processor 226 one or more locations, e.g., a home of the user 112A, coffee shop, work, gym, a home of a friend of the user 112A, a home of a family member of the user 112A, a work place of the user 112A, a place, a street, a building, etc., that the user 112A visits over a period of time. In some embodiments, the user 112A provides via the user interface 274 (FIG. 3A) of the monitoring device 108A to the processor 234 or via the input device 340 (FIG. 5) of the computing device 166 to the processor 226 a size of a location and a type of a location, e.g., work place, sandwich place, pizza place, eatery, gym, golf course, park, running place, walking place, eating place, etc. Examples of a size of a location include a number of floors within the location, a square footage of a location, a number of offices in the location, a number of rooms in the location, a number of people that can fit in the location, a height of the location, a width of the location, a length of the location, a radius of a circle that identifies the location, a diameter of a circle that identifies the location, or a combination thereof.

The one or more locations, the type of location, and/or the size of the location received from the user 112A are sent by the monitoring device 108A or by the monitoring device 108B via the computing device 166 and the network 176 to the server 228 to be stored in the geo-location-location database. In some embodiments, the one or more locations, the type of location, and/or the size of the location received from the user 112A are sent by the monitoring device 108A or by the monitoring device 108B via the network 176 to the server 228 without using the computing device 166 to be stored in the geo-location-location database.

In some embodiments, upon accessing the geo-location-location database, the processor 226 or the processor 234 determines that the geo-location-location database does not include a location corresponding to one or more geo-locations visited by the user 112A over a period of time. The processor 226 determines whether the user 112A is within a radius that includes one or more geo-locations of the user 112A. Upon determining that the user 112A is within the radius for more than a number of instances of time, the processor 226 generates a prompt to provide to the user 112A via the display device 352 or the processor 234 generates the prompt to provide to the user 112A via the display device 276. The prompt requests the user 112A to provide the location corresponding to the one or more geo-locations that are within the radius and that are visited by the user 112A.

In a number of embodiments, the processor 234 determines that among multiple locations, a location within the geo-location-location database is closest to a geo-location of the user 112A wearing a monitoring device, and determines the location to correspond to the geo-location-location of the user 112A.

In some embodiments, the processor 234 receives a selection, e.g., an expansion of a bubble-shaped or another shaped graphical element or displayed on the display device 276, a contraction of a bubble-shaped or another shaped graphical element displayed on the display device 276, etc., from the user 112A and the selection indicates that a location corresponds to a different set of geo-locations than that indicated by the geo-location-location database. Upon receiving the selection, the processor 234 determines that the location corresponds to the different set of geo-locations than that indicated by the geo-location-location database.

It should be noted that a graphical element has one or more graphical properties, e.g., a shape, a color, a shade, a texture, or a combination thereof. For example, a graphical element includes a block, a line, a box, a dot, a pin, a circle, a bubble, or a combination thereof.

Figure 6A:
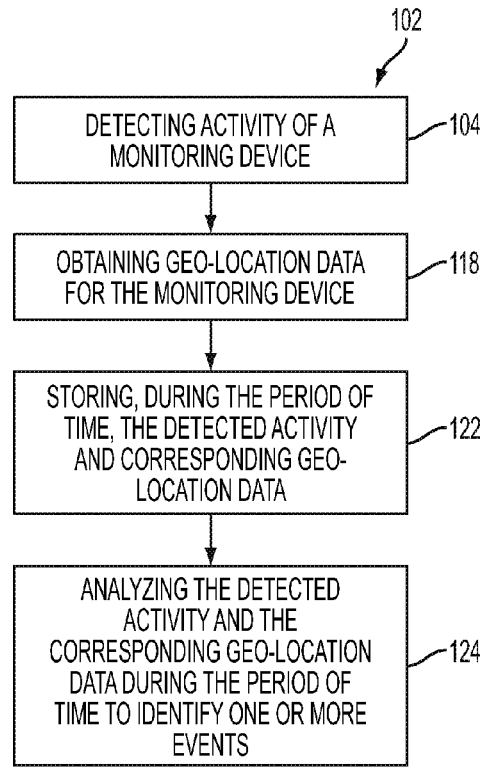
FIG. 6A is a flowchart of a method for segmenting a period of time into identification of locations of a user performing activities, in accordance with one embodiment described in the present disclosure.

FIG. 6A is a flowchart of an embodiment of a method 102 for segmenting a period of time into identification of locations of a user performing activities. The method 102 is executed by the monitoring device 108A (FIG. 3A).

The method 102 includes detecting, in an operation 104, an activity of the monitoring device 108A when the monitoring device 108A is worn by the user 112A (FIG. 1A). It should be noted that when the monitoring device 108A is worn by the user 112A, the activity of the monitoring device 108A is the same as that of the user 112A. The activity includes an amount of movement of the monitoring device 108A and is performed for a period of time. In some embodiments, the activity includes a number of calories burned by the user 112A. Examples of the activity of the user 112A detected by the monitoring device 108A include running, or walking, or jogging, or sleeping, or moving around, or a sports activity, or sleep, or a combination thereof.

The amount of movement of the user 112A includes an amount of movement of a body part of the user 112A. For example, the amount of movement of the user 112A includes an amount of stairs ascended by the user 112A, or an amount of stairs descended by the user 112A, a number of forehands of a sport played by the user 112A, or a number of backhands of the sport, or a number of serves of the sport made by the user 112A, or a number of times a golf swing is made by the user 112A, or a number of times a soccer ball is kicked by the user 112A, or a number of times a ball is thrown by the user 112A, a number of rotations of a bicycle made by the user 112A, or a number of times a paddle, e.g., a brake pedal, an accelerator pedal, etc., of a vehicle is pushed by the user 112A, or a number of times a hand movement is made by the user 112A, or a number of times a leg movement is made by the user 112A, or a number of times a steering wheel of a vehicle is rotated partially or fully by the user 112A, or an amount of calories burned by the user 112A, or an amount of distance traveled by the user 112A, an amount of steps walked or ran by the user 112A, or an amount of hours slept by the user 112A, or an amount of time for which the user 112A is active, or a combination thereof.

The detection of the activity is performed by the position sensor 220 (FIG. 3A) of the monitoring device 108A. For example, the position sensor 220 determines the amount of movement of the user 112A. The position sensor 220 determines the amount of movement at each amount of time, e.g., second, minute, hour, a fraction of a second, a fraction of a minute, a fraction of an hour, etc., that is measured by the time measurement device 232 (FIG. 3A) of the monitoring device 108A.

The method 102 further includes obtaining, in an operation 118, geo-location data for the monitoring device 108A. For example, the geo-location data includes a latitude, an altitude, and/or a longitude of the monitoring device 108A. The geo-location data is obtained by the device locator 222 (FIG. 3A) of the monitoring device 108A. For example, signals are sent between the device locator 222 and another device, e.g., a cell tower, a satellite, etc., to determine a geo-location of the device locator 222, and the geo-location of the device locator 222 is the same as a geo-location of the monitoring device 108A. The geo-location of the monitoring device 108A is the same as a geo-location of the user 112A when the user 112A is wearing the monitoring device 108A.

The method 102 also includes storing, in an operation 122, during the period of time of activity performed by the user 112A, the activity that is detected in the operation 104 and the corresponding geo-location data that is obtained in the operation 118. The geo-location data that is obtained in the operation 118 corresponds to the activity detected in the operation 104 when the geo-location is obtained and the activity is detected at the same time or during the same time period. For example, when the user 112A wearing the monitoring device 108A is performing an activity at a longitude 1 and a latitude 1, a geo-location that includes the longitude 1 and the latitude 1 corresponds to the activity. In this example, the position sensor 220 determines that the user 112A is performing the activity and the device locator 222 determines that the user 112 is at the longitude 1 and latitude 1 at the same time the user 112A is performing the activity. To further illustrate, the detected activity corresponds to the geo-location data when the activity is detected at a time the monitoring device 108A is located at the geo-location.

The operation 122 of storing is performed by the memory device 280 (FIG. 3A) of the monitoring device 108A or by a combination of the processor 234 of the monitoring device 108A and the memory device 280 of the monitoring device 108A. For example, the processor 234 writes, e.g., stores, etc., data to be stored in the memory device 280.

Figure 7A:
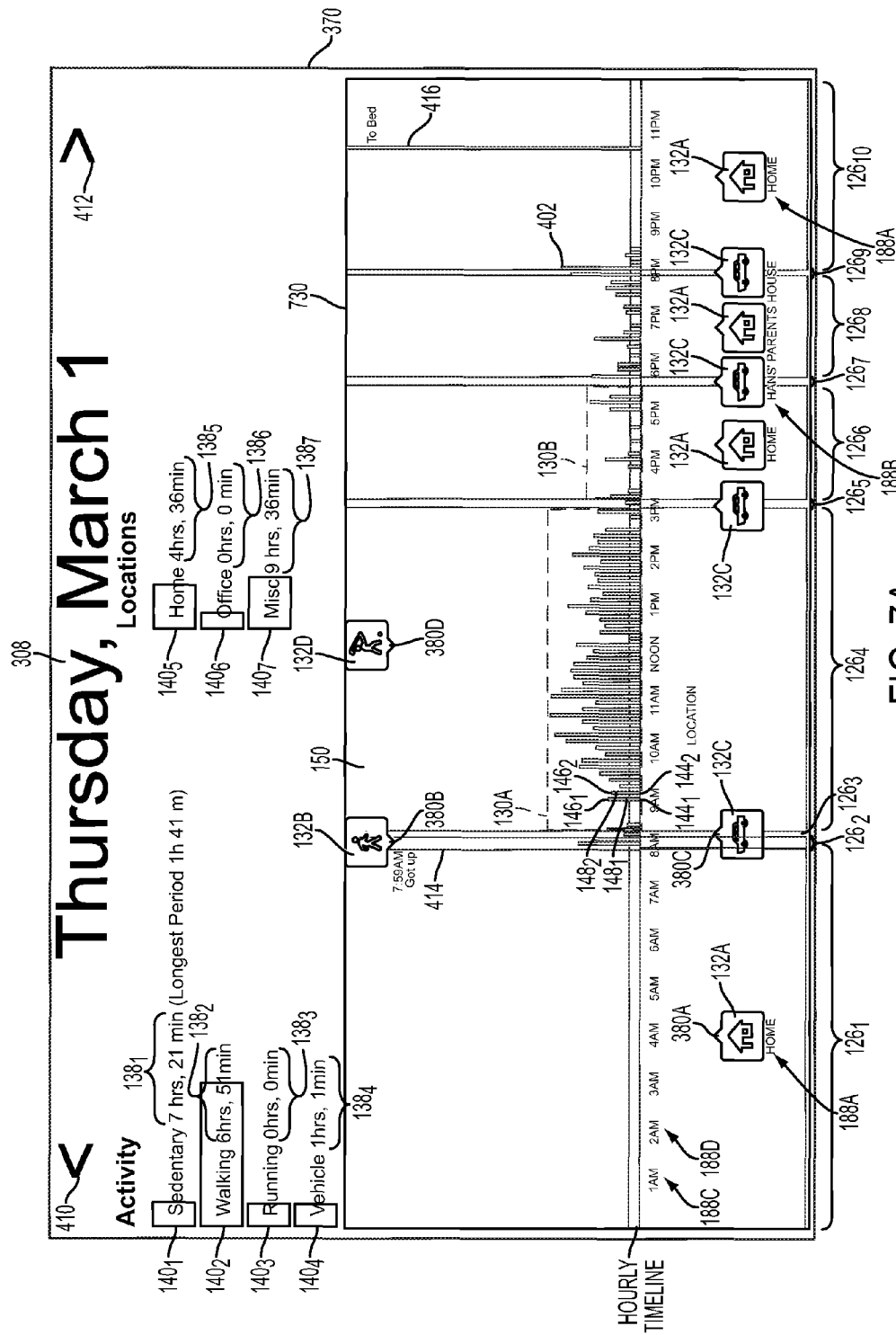
FIG. 7A is a graphical user interface (GUI) that displays one or more events and that is generated by executing the method of FIG. 6A, 6B, 6C, 6E, or 6F, in accordance with one embodiment described in the present disclosure.
Figure 7B:
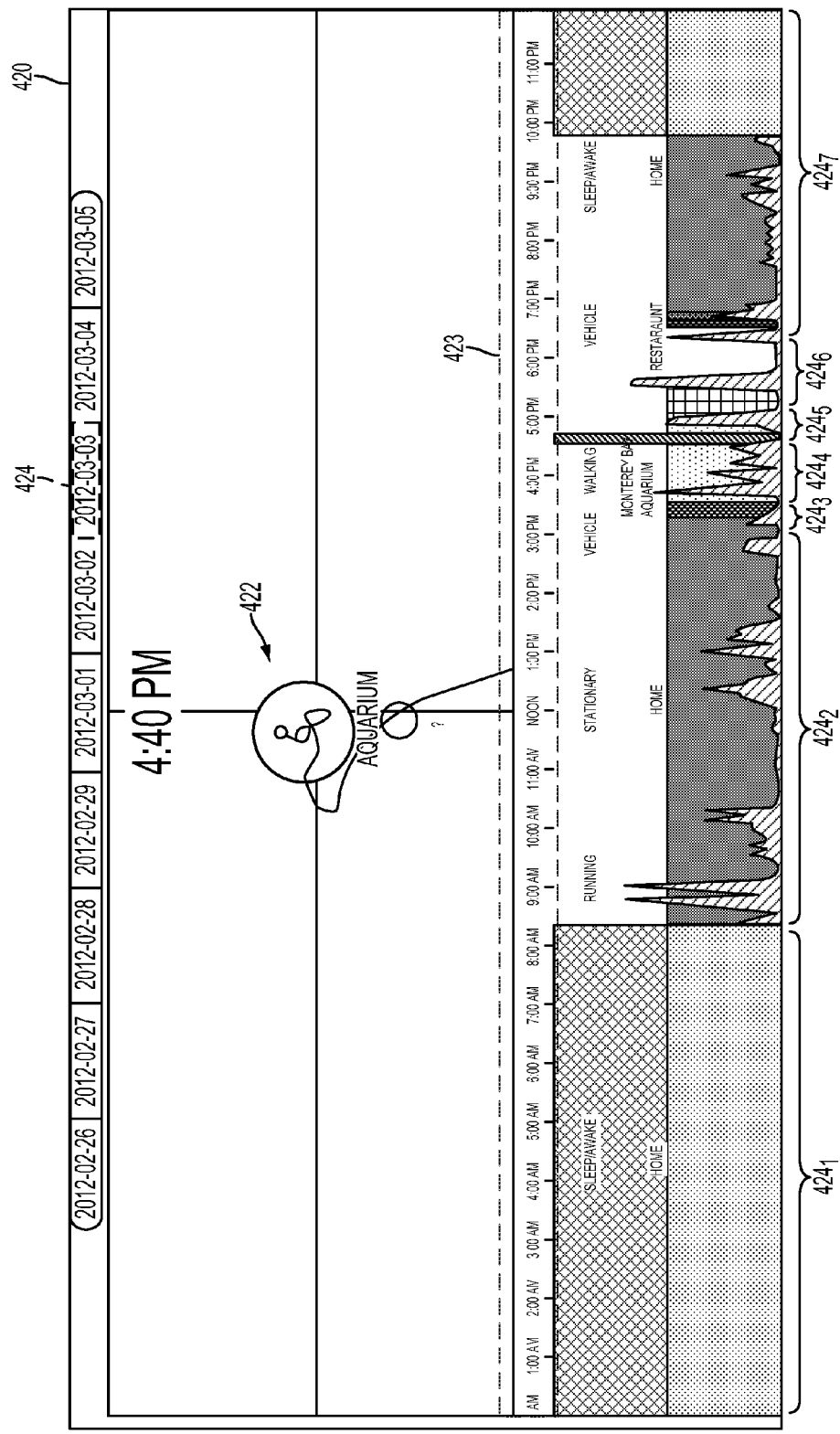
FIG. 7B is a diagram of another GUI that displays one or more events and that is generated by executing the method of FIG. 6A, 6B, 6C, 6E, or 6F in accordance with one embodiment described in the present disclosure.
Figure 7D:
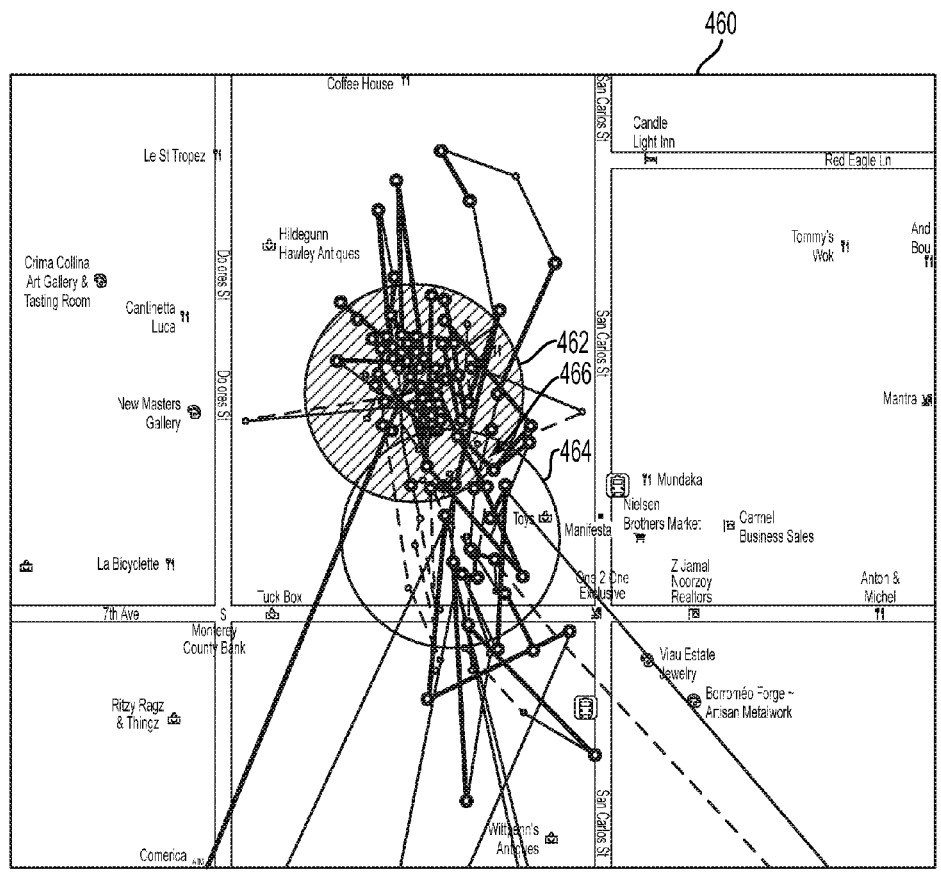
FIG. 7D is a diagram of a GUI to illustrate a method of allowing a user to choose a location in case of common geo-locations between multiple locations, in accordance with one embodiment described in the present disclosure.
Figure 7E:
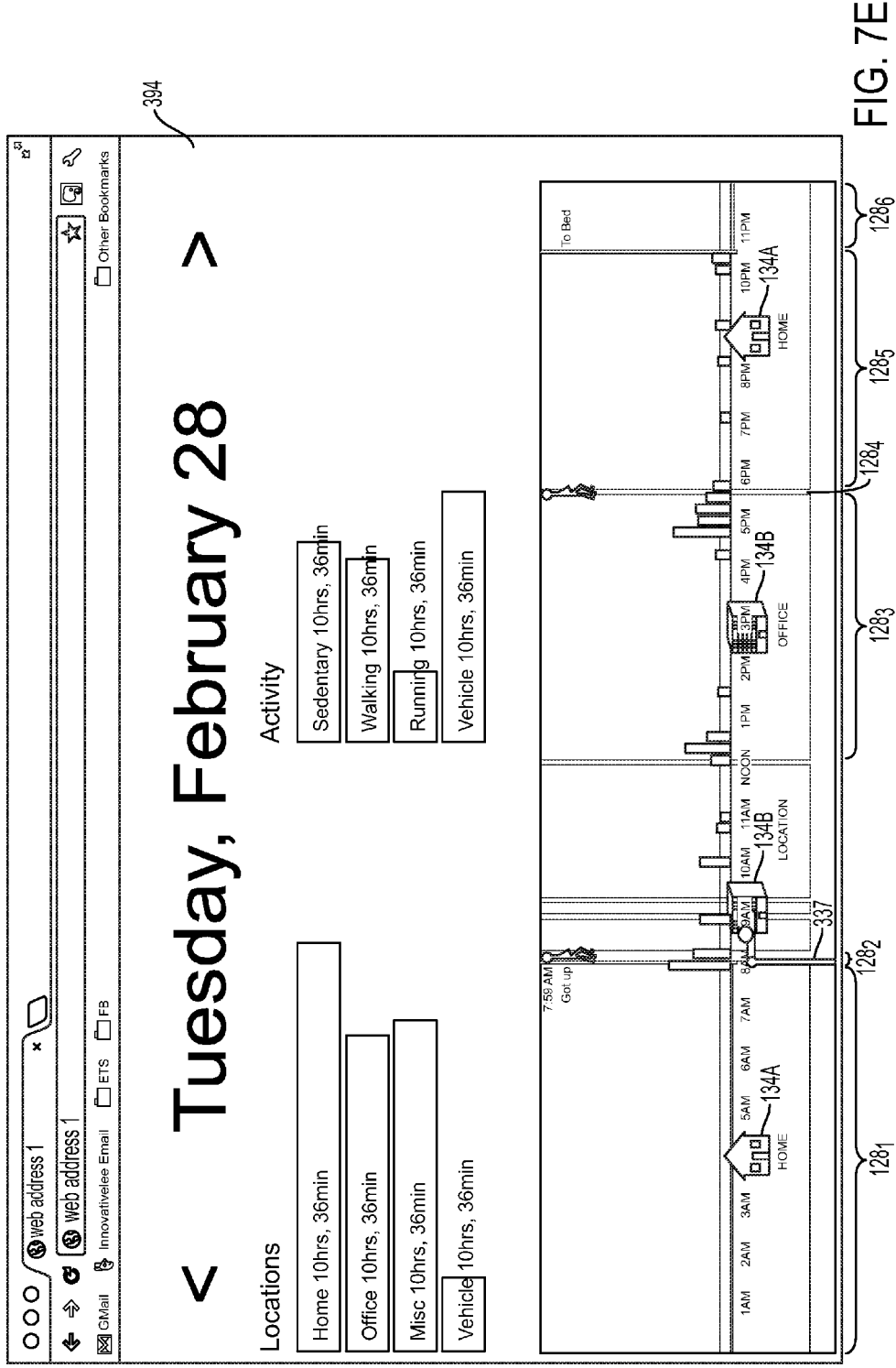
FIG. 7E is a diagram of a web page that includes a GUI that displays one or more events and that is generated by executing the method of FIG. 6A, 6B, 6C, 6E, or 6F, in accordance with one embodiment described in the present disclosure.

The method 102 further includes analyzing, in an operation 124, the activity detected in the operation 104 and the corresponding geo-location data obtained in the operation 118 to identify one or more events, e.g., an event $126_1$, an event $126_2$, an event $126_3$, an event $126_4$, an event $126_5$, an event $126_6$, an event $126_7$, an event $126_8$, an event $126_9$, an event $126_{10}$, an event $128_1$, an event $128_2$, an event $128_3$, an event $128_4$, an event $128_5$, an event $128_6$, etc., which are described with reference to FIGS. 7A and 7E. The events $126_1$, $126_2$, $126_3$, $126_4$, $126_5$, $126_6$, $126_7$, $126_8$, $126_9$, and $126_{10}$ are displayed within an event region 730 of FIG. 7A. The events $128_1$, $128_2$, $128_3$, $128_4$, $128_5$, and $128_6$ are displayed within a GUI 394 (FIG. 7E).

Each event occurs over a period of time. For example, the event $126_1$ occurs over a time period, e.g., from 12 AM to 8 AM, etc., and the event $126_4$ occurs over a time period, e.g., from a time between 8 AM and 9 AM to 3 PM, etc.

As further shown in FIG. 7A, each event $126_1$, $126_2$, $126_3$, $126_4$, $126_5$, $126_6$, $126_7$, $126_8$, $126_9$, and $126_{10}$ is a portion of a GUI 370, which is an example representation of the GUI data 186 (FIG. 2A). For example, each event $126_1$, $126_2$, $126_3$, $126_4$, $126_5$, $126_6$, $126_7$, $126_8$, $126_9$, and $126_{10}$ includes a textual and/or a graphical data portion of the GUI 370. To further illustrate, the event $126_4$ includes a graphical data portion that shows activity levels, e.g., amounts, etc., of an activity performed by the user 112A. Moreover, in this illustration, the event $126_4$ includes a time period during which the activity is performed and indicates the activity, e.g., golfing, etc. In this illustration, the activity indicates a location, e.g., a golf course. As another illustration, the event $126_6$ includes a graphical data portion that shows activity levels of an activity performed by the user 112A. Moreover, in this illustration, the event $126_6$ includes a time period during which the activity is performed and includes a location, e.g., a home of the user 112A, etc., at which the activity is performed.

Each event is associated, e.g., linked, corresponded, related, etc., with a group of activity data and one or more of the groups of activity data is associated, e.g., linked, corresponded, etc., related, with a location/activity identifier. For example, referring to FIG. 7A, the event $126_4$ includes a group 130A of activity data and the event $126_6$ includes a group 130B of activity data. The group 130A includes activity levels of an activity performed by the user 112A during a period of time and the group 130A is associated with a location/activity identifier 132D. Similarly, the group 130B includes activity levels of an activity performed by the user 112A during a period of time, e.g., a time period between a time between 3 pm and 4 pm and a time between 5 pm and 6 pm, etc., and the group 130B is associated with a location/activity identifier 132A.

Moreover, similarly, a group of activity data of the event $126_1$ is associated with the location/activity identifier 132A, a group of activity data of the event $126_2$ is associated with a location/activity identifier 132B, a group of activity data of the event $126_3$ is associated with a location/activity identifier 132C, a group of activity data of the event $126_5$ is associated with the location/activity identifier 132C, a group of activity data of the event $126_7$ is associated with the location/activity identifier 132C, a group of activity data of the event $126_8$ is associated with the location/activity identifier 132A, a group of activity data of the event $126_9$ is associated with a location/activity identifier 132C, and a group of activity data of the event $126_{10}$ is associated with a location/activity identifier 132A. Furthermore, with reference to FIG. 7E, a group of activity data of the event $128_1$ is associated with a location/activity identifier 134A and a group of activity data of the event $128_3$ is associated with a location/activity identifier 134B. A group of activity data is associated with a location/activity identifier to provide a context as to which activity is performed and where. For example, an amount of calories burned by a user are displayed in a background in which an icon representing an activity of walking performed by the user is shown and/or an icon representing a public park is shown. The amount of calories is burned when the user is walking and/or in the public park and/or is walking in the public park.

Referring back to FIG. 6A, a location/activity identifier is generated by the processor 234 using the geo-location data, which is obtained in the operation 118, and/or activity data, which is obtained in the operation 104. For example, the processor 234 (FIG. 3A) of the monitoring device 108A determines that the geo-location-location database indicates a correspondence between a location of the user 112A and a set that includes one or more longitudes at which an activity is performed by the user 112A, one or more latitudes at which the activity is performed, and/or one or more altitudes at which the activity is performed, and assigns the location/activity identifier 132D to represent the location. As another example, the processor 234 determines that a distance traveled by the user 112A in a period of time is within an upper limit and a lower limit. The period of time is received from the time measurement device 232 of the monitoring device 108A. The distance traveled by the user 112A is received from the position sensor 220 and/or the device locator 222 of the monitoring device 108A. As another example, the processor 234 receives a selection from the user 112A via the user interface 274 (FIG. 3A) of the monitoring device 108A that one or more geo-locations at which the user 112A performs an activity correspond to a location of the user 112A, and assigns a location/activity identifier to represent the location.

The operation 124 is performed by the processor 234 (FIG. 3A) based on the activity detected in the operation 104 and/or the geo-location data obtained in the operation 118, and a time period during which the activity is performed. The processor 234 receives one or more amounts of time of performance of an activity during a time period from the time measurement device 232 (FIG. 3A), and/or receives one or more geo-locations at which the activity is performed during the time period from the device locator 222 (FIG. 3A), and receives one or more activity levels of the activity from the position sensor 220 (FIG. 3A) to perform the operation 124. For example, the processor 234 determines that the user 112A is in a vehicle upon determining that a speed of travel of the user 112A is greater than $s_1$ miles per hour. The speed $s_1$ is a running or walking speed of one or more users. The processor 234 determines a speed of travel of the user 112A based on geo-location data obtained in an hour of one or more geo-locations of the user 112. Geo-location data is received from the device locator 222 (FIG. 3A) of the monitoring device 108A and a measurement of the hour is received from the time measurement device 232 (FIG. 3A).

As another example, the processor 234 determines whether the user 112A is in a vehicle, or is riding a bicycle or a skateboard, or is undergoing ambulatory motion based on a speed of the user 112A and motion of a body portion of the user 112A. To illustrate, when the processor 234 determines that a speed of the user 112A is greater than a pre-determined number of miles per hour and motion of the body portion is less than a pre-determined amount of motion, the processor 234 determines that the user 112A is in a vehicle and is not walking or running. As another illustration, when the processor 234 determines that a speed of the user 112A is less than the pre-determined number of miles per hour and motion of the body portion is greater than the pre-determined amount of motion, the processor 234 determines that the user 112A is performing the ambulatory motion. Examples of ambulatory motion include walking, running, jogging, exercising, etc. An example of the body portion includes an arm of the user 112A. In various embodiments, a speed of the user 112A is determined by a device locator or a processor based on an amount of distance between two geo-locations and time of the user 112A at each of the geo-locations. In some embodiments, a speed of the user 112A is determined by a position sensor or a processor based an amount of distance between two positions and time of occurrence of each of the positions.

As yet another example, the processor 234 determines that the user 112A is running upon determining that a speed of travel of the user 112A is greater than $s_2$ miles per hour and a number of steps taken by the user 112A is greater than $ss_1$ per hour. The speed $s_2$ is a walking speed of one or more users. A number of steps are received by the processor 234 from the position sensor 220 (FIG. 3A) of the monitoring device 108A. As another example, the processor 234 determines that the user 112A is walking upon determining that a number of steps taken by the user 112A is less than $ss_1$ per hour and greater than $ss_2$ per hour. As yet another example, the processor 234 determines that the user 112A is in a vehicle upon determining that a speed of travel of the user 112A is greater than $s_3$ miles per hour and a number of steps taken by the user 112A is less than $ss_3$ per hour.

As another example, the processor 234 determines that the user 112A is moving around upon determining that a number of steps taken by the user 112A is less than $ss_4$ per hour. As yet another example, the processor 234 determines that the user 112A is sedentary upon determining that the user 112A is not walking, running, not moving around, and not in a vehicle. As another example, the processor 234 determines that the user 112A is sleeping upon determining that the user 112A is sedentary for greater than an amount of time.

In some embodiments, the processor 234 determines a speed of travel of the user 112A based on geo-location data obtained over a period of time of one or more geo-locations of the user 112 and the period of time.

The time period during which the activity is performed at a location is determined by the processor 234 based on a sum of amounts of time measured by the time measurement device 232 for performing the activity at one or more geo-locations corresponding to, e.g., included within, linked with, etc., the location.

The operation 124 of analyzing the detected activity and the corresponding geo-location data during the period of time includes determining a time element of segregation of the activity detected at the operation 104. For example, a period of time during which an activity is performed is segmented into one or more time elements. As another example, a period of time during which an activity is performed is segmented into one or more time elements, and each time element includes a graphical property and/or text to represent the time element. Examples of a time element include a fraction of a minute, or a minute, or a fraction of an hour, or an hour, etc. Further examples of a time element are shown as a time element $144_1$ and a time element $144_2$ in FIG. 7A. The time element $144_1$ is a time of day at which a golf activity having an activity level is performed by the user 112A. Moreover, the time element $144_2$ is another time of day at which a golf activity having an activity level is performed by the user 112A. The activity level at the time element $144_2$ is lower than the activity level at the time element $144_1$. In some embodiments, the activity level at the time element $144_2$ is higher than or the same as the activity level at the time element $144_1$. The time element $144_1$ includes text, e.g., 9 AM, etc.

The operation 124 of analyzing the detected activity and the corresponding geo-location data during the period of time further includes determining an activity level for each time element. For example, an activity level $146_1$ (FIG. 7A) is determined as being performed at the time element $144_1$ and an activity level $146_2$ (FIG. 7A) is determined as being performed at the time element $144_2$. As another example, the activity level $146_1$ (FIG. 7A) is determined as being performed at the time element $144_1$ and is determined to include text and/or a graphical property, e.g., a dark gray bar, etc., and the activity level $146_2$ (FIG. 7A) is determined as being performed at the time element $144_2$ and is determined to include text and/or a graphical property, a dark gray bar, etc.

The operation 124 of analyzing the detected activity and the corresponding geo-location data during the period of time also includes determining a location/activity identifier of a location and/or activity for each time element and for each activity level. For example, the processor 234 determines that an activity level that occurs at a time element is of an activity that occurs at one or more geo-locations that correspond to a location and/or that correspond to an activity, e.g., a home of the user 112, a building, a park, an office, golfing, walking, running, a commercial place, an eatery, a work place, a vehicle, a golf course, a sandwich shop, or any other location, etc., and determines a location/activity identifier that represents the location and/or activity.

As another example, the processor 234 determines that the activity level $146_1$ is of an activity that occurs at one or more geo-locations of a golf course and determines the location/activity identifier 132D that represents golfing. In this example, the processor 234 accesses correspondence between geo-location data and location data stored within the geo-location-location database to determine whether the one or more geo-locations correspond to the golf course and/or also accesses position data of the monitoring device 108A from the position sensor 220 to determine that the activity is golfing. As yet another example, the processor 234 determines that the activity level $146_2$ is of an activity that occurs at one or more geo-locations of a golf course and determines the location/activity identifier 132D. In this example, the processor 234 applies a selection received from the user 112A via the user interface 274 (FIG. 3A) to determine that one or more geo-locations at which the activity level $146_2$ occurs correspond to a golf course. In this example, the geo-locations at which the activity level $146_2$ occurs are the same or different from one or more geo-locations determined by the processor 234 from the geo-location-location database to correspond to a golf course.

Examples of a location/activity identifier include a graphical element, e.g. an icon, an icon having a pointer, a symbol, a symbol having a pointer, a trademark, a trademark having a pointer, a registered mark, a registered mark having a pointer, an animation icon, an animation icon having a pointer, an animation, an animation having a pointer, a video icon, a video icon having a pointer, a video, a video having a pointer, an audio icon, an audio icon having a pointer, an audio, an audio having a pointer, a multimedia icon, a multimedia icon having a pointer, a multimedia, a multimedia having a pointer, or a combination thereof, etc., that represents a location at which the activity is performed.

A location/activity identifier has a graphical element and/or text. For example, the location/activity identifier 380B includes an icon of a person walking. As another example, the location/activity identifier 380D includes an icon of a person golfing with a golf club.

The operation 124 of analyzing the detected activity and the corresponding geo-location data during the period of time further includes associating the activity level with the time element and the location/activity identifier. Upon determining the location/activity identifier for each time element and for each activity level, the processor 234 associates, e.g., establishes a link between, establishes a correspondence between, etc., the time element and the activity level with the location/activity identifier. For example, the processor 234 establishes a link between the time element $144_1$, the activity level $146_1$, and the location/activity identifier 132D. As another example, the processor 234 establishes a link between the time element $144_2$, the activity level $146_2$, and the location/activity identifier 132D.

The operation 124 of analyzing the detected activity and the corresponding geo-location data during the period of time also includes aggregating the associated activity levels and time elements over the period of time to indicate, using the associated location/activity identifier, a location of occurrence of the activity levels and of a group of activity data. The group of activity data includes the activity levels and the period of time. The processor 234 aggregates, e.g., combines, accumulates, etc., over a period of time the activity levels and time elements that are associated with a location/activity identifier of an activity. The period of time over which the processor 234 aggregates is continuous, e.g., from 1 pm to 2 pm on a day, from January to February of a year, from year 2000 to year 2004 of a decade, etc.

The aggregated activity levels, time elements, and the associated location/activity identifier are represented, by the processor 234, within one or more graphical elements and/or text of a background that represent an event to generate or identify the event. For example, the processor 234 assigns one or more graphical elements to an area, within the GUI 370 (FIG. 7A), to generate the event $126_4$ that includes the group 130A of activity data, the location/activity identifier 380D and a background 150, e.g., a gray-shaded area, a shaded area, an area having a graphical property, etc. The group 130A of activity data and the location/activity identifier 380D are overlaid on the background 150. The event $126_4$ includes the time element $144_1$ aligned, e.g., vertically, horizontally, oblique, etc., with the activity level $146_1$ and further includes the location/activity identifier 132D including or attached to a pointer 380D. The pointer 380D points to the event $126_4$ that includes the activity level $146_1$ and the time element $144_1$. Similarly, as shown in FIG. 7A, a pointer 380A that is included within or is attached to the location/activity identifier 132A points to the event $126_1$, a pointer 380B that is included within or is attached to the location/activity identifier 132B points to the event $126_2$, and a pointer 380C that is included within or is attached to the location/activity identifier 132C points to the event $126_3$.

It should be noted that in some embodiments, a location/activity identifier does not include and is not attached to a pointer. For example, the event $126_4$ includes the location/activity identifier 132D without the pointer 380D.

In various embodiments, a group of activity data includes a location/activity identifier in addition to one or more activity levels and one or more time elements. For example, the group 130A of activity data includes one or more activity levels, one or more time elements, and the location/activity identifier 380D.

In several embodiments, each activity level is assigned a graphical property by the processor 234. For example, as shown in FIG. 7A, the activity level $146_1$ is assigned a graphical property $148_1$ and the activity level $146_2$ is assigned a graphical property $148_2$. The graphical property $148_2$ may be the same or different from the graphical property $148_1$. For example, the graphical property $148_2$ has the same color as that of the graphical property $148_1$. As another example, the graphical property $148_2$ has the same texture and color as that of the graphical property $148_1$.

In some embodiments, the method 102 is performed by the monitoring device 108B (FIG. 3B) except instead of the operation 104, the biological sensor 294 performs an operation of detecting a physiological parameter of the user 112A who is located on the monitoring device 108B. Moreover, in these embodiments, the operation 118 of obtaining geo-location data for the monitoring device 108B is performed by the device locator 306 (FIG. 3B). Further, in these embodiments, the operation 122 of storing the detected physiological parameter and the corresponding geo-location data is performed by the processor 302 (FIG. 3B) or by a combination of the processor 302 and the memory device 298 (FIG. 3B). In these embodiments, the operation 124 of analyzing the detected physiological parameter and the corresponding geo-location data during the period of time to identify one or more events is performed by the processor 302 (FIG. 3B) of the monitoring device 108B.

Figure 6B:
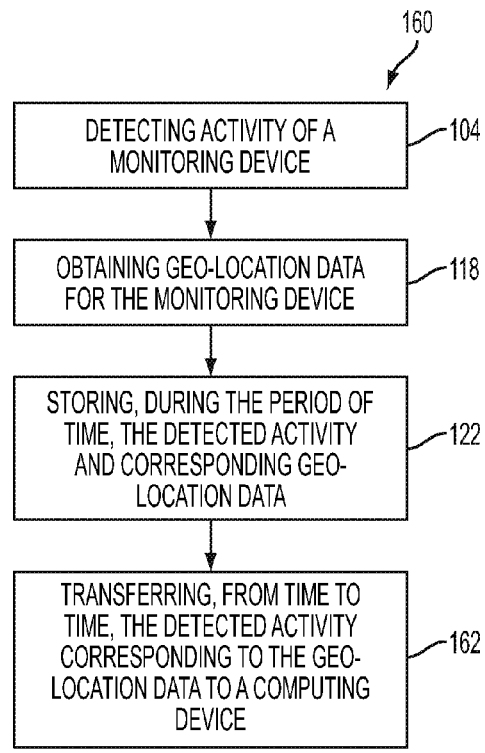
FIG. 6B is a flowchart of another method for segmenting a period of time into identification of locations of a user performing activities, in accordance with one embodiment described in the present disclosure.

FIG. 6B is a flowchart of an embodiment of a method 160 for segmenting a period of time into identification of locations of a user performing activities. The method 160 is executed by the monitoring device 108A (FIG. 3A). In the method 160, the operations 104, 118, and 122 are performed.

The method 160 includes transferring, e.g., sending, etc., in an operation 162, from time to time, to the computing device 166 (FIG. 5) the activity that is detected at the operation 104 and that corresponds to the geo-location data that is obtained at the operation 118. For example, activity data is transferred periodically, e.g., every fraction of a second, every second, every minute, every fraction of a minute, etc., or aperiodically, e.g., randomly, etc., to the computing device 166 upon reception of request from the computing device 166.

The operation 162 of transferring is performed by the wireless communication device 278 (FIG. 3A) via a wireless link, e.g., the wireless link 168 (FIG. 2A), the wireless link 170 (FIG. 2B), etc., between the monitoring device 108A (FIG. 3A) and the computing device 166. For example, the wireless communication device 278 executes a Bluetooth or a Wi-Fi protocol to transfer data to the computing device 166 via a wireless link. In some embodiments in which a wired link is used between the monitoring device 108A and the computing device 166, the operation 162 of transferring is performed by a wired communication device of the monitoring device 108A and the wired communication device is connected via a wired link to the wired communication device of the computing device 166. In various embodiments, the wireless communication device 278 transfers data via a wireless communication link and the network 176 (FIG. 3A) to the server 228 (FIG. 3A) without transferring data via the computing device 166. In several embodiments, a wired communication device of the monitoring device 108A transfers via a wired communication link and the network 176 to the server 228 without transferring data via the computing device 166. For example, the wired communication device of the monitoring device 108A executes a communication protocol, e.g., a Transmission Control Protocol over Internet Protocol (TCP/IP), a User Datagram Protocol over Internet Protocol (UDP/IP), etc., to communicate data with the server 228 via the network 176.

In some embodiments, the operations 104, 118, and 112 are performed by the monitoring device 108B (FIG. 3B) with the changes described above with respect to the method 102 (FIG. 6A). Moreover, in these embodiments, the operation 162 of transferring, from time to time, the detected activity corresponding to the geo-location data to the computing device 166 is performed by the wireless communication device 300 of the monitoring device 108B or by a wired communication device of the monitoring device 108B.

Figure 6C:
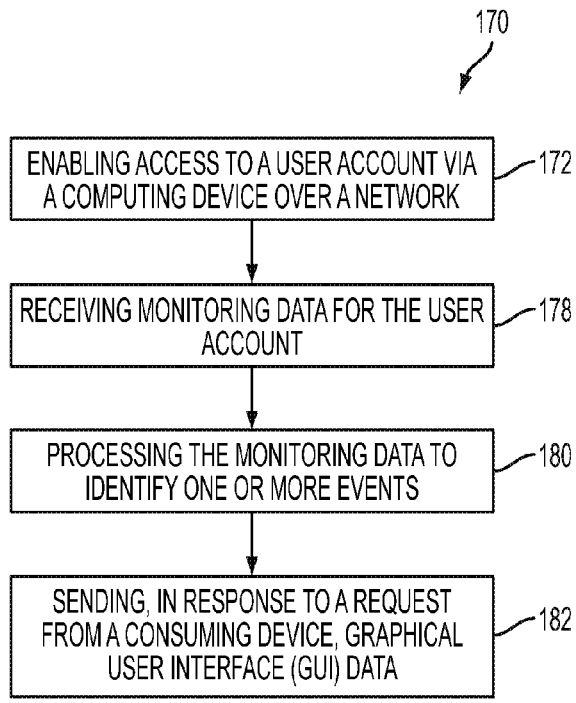
FIG. 6C is a flowchart of yet another method for segmenting a period of time into identification of locations of a user performing activities, in accordance with one embodiment described in the present disclosure.

FIG. 6C is a diagram of an embodiment of a method 170 for segmenting a period of time into identification of locations of a user performing activities. The method 170 is executed by the server 228 (FIGS. 2A & 2B). The method 170 includes an operation 172 of enabling access to the user account 174 (FIG. 2A) via the computing device 166 (FIG. 5) over the network 176 (FIG. 2A). The processor 190 (FIG. 2A) of the server 228 performs the operation 172 of enabling access to the user account 174.

The user 112A (FIG. 1A) uses the user interface 274 (FIG. 3A) of the monitoring device 108A or the input device 340 (FIG. 5) of the computing device 166 to provide the authentication information to access the user account 174. Upon receiving the authentication information via the network 176, the processor 190 (FIG. 2A) of the server 228 or another processor of another server determines whether the authentication information is authentic. Upon determining that the authentication information is authentic or upon receiving the determination from the other processor of the other server, the processor 190 enables access to the user account 174 to the user 112A. When access to the user account 174 is enabled, a representation of the user account 174 is rendered by the processor 234 on the display device 276 (FIG. 3A) of the monitoring device 108A or is rendered by the processor 226 of the computing device 166 on the display device 352 (FIG. 5) of the computing device 166.

The method 170 further includes receiving, in an operation 178, monitoring data for the user account 174. The monitoring data includes the activity detected at the operation 104 (FIGS. 6A & 6B) of the monitoring device 108A (FIG. 3A). The monitoring data includes geo-location data obtained at the operation 118 (FIG. 6A).

The operation of receiving 178 is performed by the NIC 254 (FIG. 2A) of the server 228. The monitoring data is received, via the network 176 (FIGS. 2A, 2B, & 3A), from the NIC 356 (FIG. 5) of the computing device 166 that has received the monitoring data from the wireless communication device 278 (FIG. 3A) of the monitoring device 108A or from a wired communication device of the monitoring device 108A. In some embodiments, the monitoring data is received from the wireless communication device 278 of the monitoring device 108A and the network 176 without use of the computing device 166.

In some embodiments, the NIC 254 applies a communication protocol to receive the monitoring data. For example, the NIC 254 depacketizes one or more packets to obtain the monitoring data.

The method 170 includes processing, in an operation 180, the monitoring data to identify one or more events. The operation 180 of processing is similar to the operation 124 (FIG. 6A) of analyzing the detected activity and the corresponding geo-location data during a period of time to identify one or more events. For example, the operation 180 is the same as the operation 124 except that the operation 180 is performed by the processor 190 (FIG. 2A) of the server 228. The operation 180 is performed to generate the GUI data 186 (FIG. 2A). The GUI data 186 includes event data of one or more events. For example, the GUI data 186 includes data that is rendered to display the GUI 370 (FIG. 7A). As another example, the GUI data 186 includes data that is rendered to display the GUI 394 (FIG. 7E).

The method 170 includes sending, in an operation 182, in response to a request from a consuming device the GUI data 186 (FIG. 2A). Examples of the consuming device include the computing device 166 (FIG. 5) or the monitoring device 108A (FIG. 3A). For example, when the user 112A is provided access to the user account 174 (FIG. 2A), a request is received from the NIC 356 (FIG. 5) to send the GUI data 186. Upon receiving the request, the NIC 254 (FIG. 2A) of the server 228 applies a communication protocol for sending the GUI data 186 via the network 176 to the NIC 356 of the computing device 166 for display on the display device 352 of the computing device 166. As another example, when the user 112A is provided access to the user account 174, a request is received from the wireless communication device 278 of the monitoring device 108A or a wired communication device of the monitoring device 108A via the network 176. Upon receiving the request, the NIC 254 (FIG. 2A) of the server 228 applies a communication protocol for sending the GUI data 186 via the network 176 to the wireless communication device 278 of the monitoring device 108A or to the wired communication device of the monitoring device 108A. The GUI data 186 is sent via the computing device 166 or without using the computing device 166.

The GUI data 186 includes graphics, e.g., graphical elements that represent the events $146_1$ and $146_2$ (FIG. 7A), that represent the background 150 (FIG. 7A), that represent the location/activity identifiers 132A, 132B, 132C, and 132D (FIG. 7A), etc. The GUI data 186 further includes text, e.g., text 188A ("e.g., HOME" in FIG. 7A) that describes, e.g., identifies, etc., a location that the user 112A has reached during a day, text 188B ("e.g., HANS' PARENTS HOUSE" in FIG. 7A) that describes another location that the user 112A has reached during the day another time of the day, text 188C (e.g., "1 AM" in FIG. 7A) that represents a time of the day, text 188D (e.g., "2 AM" in FIG. 7A) that represents yet another time of the day, etc.

The graphics and text segments a period of time over which one or more activities are performed into events that are graphically distinct from each other. For example, as shown in FIG. 7A, the event $126_2$ that includes activity data of an activity of walking is graphically distinct, e.g., has a lighter shade, etc., than the event $126_4$ that includes activity data of an activity of golfing. As another example, as shown in FIG. 7A, an event includes activity data representing an activity is represented by different graphical elements than an event that includes activity data representing the same or a different activity.

Figure 6D:
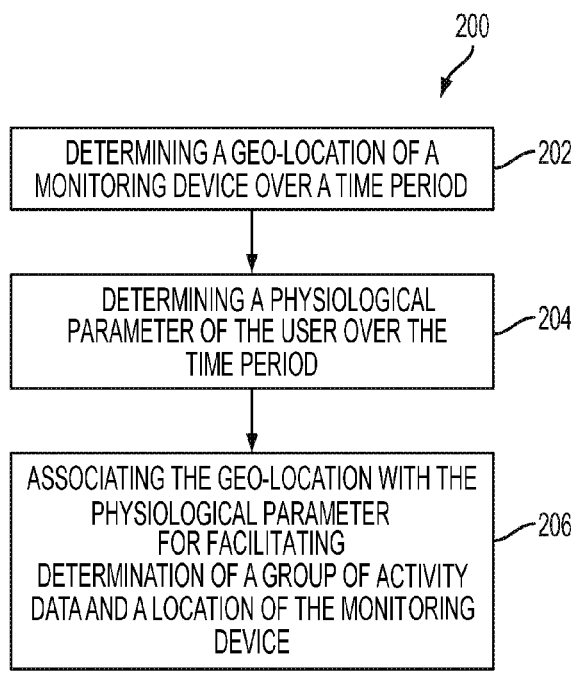
FIG. 6D is a flowchart of a method for segmenting a period of time into identification of locations of a user performing activities, in accordance with one embodiment described in the present disclosure.

FIG. 6D is a flowchart of an embodiment of a method 200 for segmenting a period of time into identification of locations of a user performing activities. The method 200 is executed by the monitoring device 108B (FIG. 3B).

The method 200 includes determining, in an operation 202, a geo-location of the monitoring device 108B over a time period. The geo-location of the monitoring device 108B is determined by the device locator 306 (FIG. 3B). The method 200 further includes determining, in an operation 204, a physiological parameter of the user 112A over a period of time. The operation 204 is performed by the biological sensor 294 (FIG. 3B) of the monitoring device 108B. For example, the biological sensor 294 measures a change in weight of the user 112A over a period of time for which the geo-location is determined in the operation 202. As another example, the biological sensor 294 measures a change in BMI of the user 112A over a period of time for which the geo-location is determined in the operation 202. A period of time is measured by the time measurement device 395 (FIG. 3B).

The method 200 also includes associating, in an operation 206, the geo-location determined in the operation 202 with the physiological parameter determined in the operation 204 to facilitate determination of a group of activity data and a location of the monitoring device 108B. The processor 302 (FIG. 3B) of the monitoring device 108B performs the operation 206. For example, the processor 302 establishes a link between the geo-location data and the physiological parameter. The processor 302 determines a location of the monitoring device 108B based on the geo-location data and the geo-location-location database. The processor 302 further determines a group of activity data that includes one or more amounts of a physiological parameter that provide a measure of an activity performed over a period of time. For example, when the user 112A exercises over a period of time, the user 112A may lose weight. As another example, when the user 112A is sedentary over a period of time, the user 112A may gain weight. The processor 302 then generates event data that includes a relation between the location and the group of activity data. For example, the processor 302 determines that one or more amounts of a physiological parameter occur at a location over a period of time and generates a relationship, e.g., correspondence, link, etc., between the amounts, the location, and the time period.

Figure 6E:
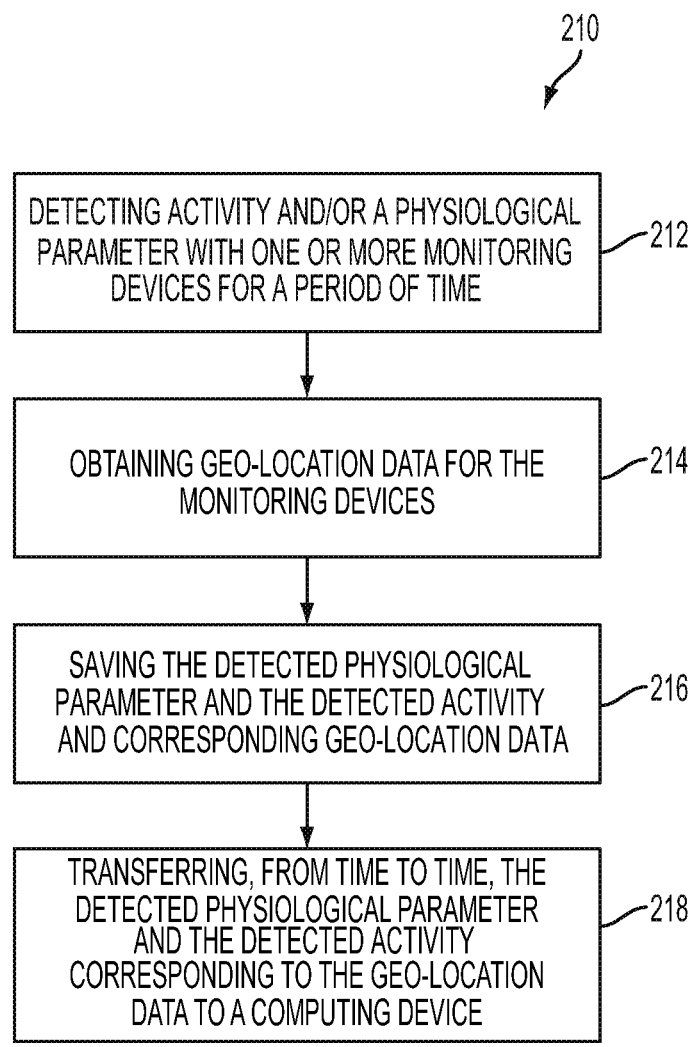
FIG. 6E is a flowchart of another method for segmenting a period of time into identification of locations of a user performing activities, in accordance with one embodiment described in the present disclosure.

FIG. 6E is a flowchart of an embodiment of a method 210 for segmenting a period of time into identification of locations of a user performing activities. The method 210 is performed by one or more monitoring devices, e.g., the monitoring device 108A, the monitoring device 108B, a combination thereof, etc.

The method 210 includes an operation 212 of detecting an activity and/or a physiological parameter of the user 112A with one or more monitoring devices for a period of time. For example, the position sensor 220 of the monitoring device 108A (FIG. 3A) detects an activity performed by the user 112A and the biological sensor 294 of the monitoring device 108B (FIG. 3B) detects a physiological parameter of the user 112A.

The method 210 further includes an operation 214 of obtaining geo-location data for the monitoring devices for the period of time for which the operation 212 is performed. For example, geo-location data of geo-location of the monitoring device 108A is measured by the device locator 222 of the monitoring device 108A (FIG. 3A) and geo-location data of geo-location of the monitoring device 108B is measured by the device locator 306 of the monitoring device 108B (FIG. 3B). A period of time is measured by the time measurement device 232 (FIG. 3A) of the monitoring device 108A and by the time measurement device 295 of the monitoring device 108B (FIG. 3B).

The method 210 includes an operation 216 of saving, in an operation 216, the detected physiological parameter and the detected activity in the operation 212. For example, the operation 216 of saving the detected activity is performed by the processor 234 of the monitoring device 108A and/or by the processor 234 and the memory device 280 of the monitoring device 108A. As another example, the operation 216 of saving the detected physiological parameter is performed by the processor 302 of the monitoring device 108B and/or by the memory device 298 (FIG. 3B) of the monitoring device 108B.

The method 210 includes an operation 218 of transferring, from time to time, the detected physiological parameter and the detected activity corresponding to the geo-location data to the computing device 166 (FIG. 5) and/or to the server 228. For example, the operation 218 of transferring is performed by the wireless communication device 278 (FIG. 3A) of the monitoring device 108A or by a wired communication device of the monitoring device 108A. As another example, the operation 218 of transferring is performed by the wireless communication device 300 of the monitoring device 108B or by a wired communication device of the monitoring device 108B. The detected activity and the detected physiological parameter are transferred wirelessly to the wireless communication device 224 (FIG. 5) of the computing device 166. In some embodiments, the detected activity and the detected physiological parameter are transferred via a wired link, e.g., a cable, a wire, etc., to the wired communication device (not shown) of the computing device 166. In several embodiments, the detected activity and the detected physiological parameter are transferred via a wired link or a combination of a wireless link and a wired link and the network 176 to the server 228 without use of the computing device 166.

Moreover, in some embodiments, the geo-location data is also transferred, from time to time, to the computing device 166 and/or to the server 228. For example, the wireless communication device 278 (FIG. 3A) of the monitoring device 108A transfers geo-location data to the wireless communication device 224 of the computing device 166 or a wired communication device of the monitoring device 108A transfers the geo-location data to the wired communication device of the computing device 166. As another example, the geo-location data is transferred wirelessly by the wireless communication device 300 of the monitoring device 108B or by a wired communication device of the monitoring device 108B to the computing device 166. In several embodiments, the geo-location data is transferred via a wired link or a combination of a wireless link and a wired link and the network 176 to the server 228 without use of the computing device 166.

Figure 6F:
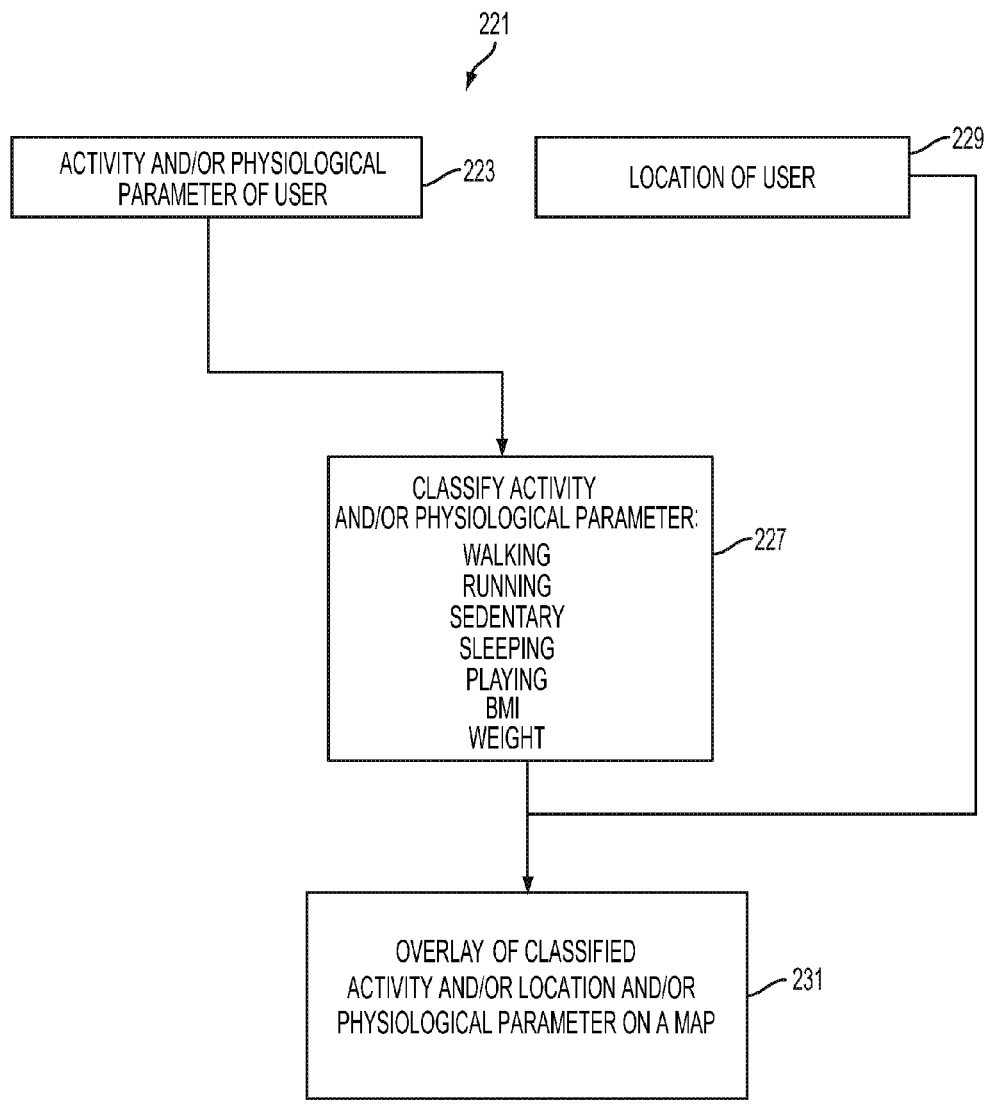
FIG. 6F is a flowchart of a method for combining a map with event data, in accordance with one embodiment described in the present disclosure.

FIG. 6F is a flowchart of an embodiment of a method 221 for segmenting a period of time into identification of locations of a user performing activities. The method 221 is performed by the monitoring device 108A, the monitoring device 108B, by the computing device 166, or a combination thereof.

The method 221 includes receiving, in an operation 223, detected activity and/or physiological parameter of the user 112A. For example, the processor 234 (FIG. 3A) of the monitoring device 108A receives detected activity from the position sensor 220 (FIG. 3A). As another example, the processor 302 of the monitoring device 108B receives detected physiological parameter from the biological sensor 294 (FIG. 3B) of the monitoring device 108B. As yet another example, the processor 226 of the computing device 166 (FIG. 5) receives the detected activity from the monitoring device 108A and/or receives the physiological parameter from the monitoring device 108B.

The method 221 includes an operation 227 of classifying detected activity and/or the physiological parameter. For example, the processor 234 (FIG. 3A) of the monitoring device 108A classifies the amount of movement into walking, running, sedentary, sleeping, moving around, or playing a sport. As another example, the processor 302 of the monitoring device 108B classifies the physiological parameter into a type of physiological parameter, e.g., BMI, heart rate, blood pressure, weight, etc. As another example, the processor 226 of the computing device 166 classifies the detected activity and/or the physiological parameter.

The method 221 further includes an operation 229 of determining a location of the user 112A. For example, the processor 234 of the monitoring device 108A determines a location of the user 112A based on geo-location data and/or based on detected activity and/or based on the geo-location-location database. The geo-location data is received by the processor 234 from the device locator 222 of the monitoring device 108A and the detected activity is received by the processor 234 from the position sensor 220 (FIG. 3A) of the monitoring device 108A. Moreover, a determination of a location based on the geo-location data is made by the processor 234 based on the geo-location data and/or the activity data and/or the geo-location-location database.

As another example, the processor 226 of the computing device 166 determines a location of the user 112A based on geo-location data and/or based on detected activity and/or based on a physiological parameter, and/or based on the geo-location-location database. The geo-location data is received by the processor 226 from the device locator 222 of the monitoring device 108A or from the device locator 306 of the monitoring device 108B and the detected activity is received by the processor 226 from the position sensor 220 (FIG. 3A) of the monitoring device 108A and/or a physiological parameter is received from the biological sensor 294 of the monitoring device 108B. Moreover, a determination of a location based on the geo-location data is made by the processor 234 based on the geo-location data and/or the activity data and/or the physiological parameter and/or the geo-location-location database. For example, upon determining that there is a lack of change beyond an amount in a physiological parameter over a period of time, the processor 234 determines that the user 112A has not left one or more geo-locations that corresponds to his/her home during the period of time.

In some embodiments, the processor 226 classifies an activity based on a physiological parameter of the user 112A, and/or a movement of the user 112A, and/or a location of the user 112A. For example, a heart rate of the user 112A is monitored, a movement of an arm of the user 112A is determined, and a location of the user 112A is determined to determine that the user 112A is training with weights in a gym and not swimming in the gym. As another example, an amount of calories burned by the user 112A is measured, a movement of an arm of the user 112A is determined, and a location of the user 112A is determined to indicate that the user 112A is swimming in a gym as opposed to running in the gym.

The method 221 further includes an operation 231 of overlaying of the classified activity performed by the user 112A and/or of the classified physiological parameter of the user 112A and/or of a location arrived at by the user 112A on a map. For example, the processor 234, the processor 302, or the processor 226 determines generates event data that includes the map, the classified activity, and/or the classified physiological parameter. In some embodiments, instead of the operation 231, an operation of overlaying the map is performed on the classified activity and/or the classified physiological parameter and/or the location arrived at by the user 112A.

In various embodiments, event data is generated based on positions that are obtained by a position sensor of a monitoring device and geo-locations obtained by a device locator of the computing device 166. The geo-locations are of the computing device 166 when carried by the user 112A. The computing device 166 transfers the geo-locations via a NIC and the network 176 to the server 228. Moreover, the monitoring device transfers the positions via a communication device and the network 176 to the server 228. The server 228 receives the geo-locations and the positions and generates the event data. In some embodiments, instead of the server 228, a virtual machine generates the event data.

In some embodiments, a monitoring device receives the geo-location data that is obtained by a device locator of the computing device 166 and generates event data based on positions and the geo-locations. The monitoring device includes a position sensor that determines the positions of the monitoring device. The monitoring device receives the geo-locations via a communication device of the monitoring device and a communication device of the computing device 166. The geo-locations are of the computing device 166 when carried by the user 112A.

In several embodiments, the computing device 166 receives positions that are obtained by a position sensor of a monitoring device and generates event data based on positions and the geo-locations. The geo-locations are of the computing device 166 when carried by the user 112A. The monitoring device includes a position sensor that determines the positions of the monitoring device.

In various embodiments, a portion of the event data is generated by a processor of a monitoring device and the remaining portion is generated by a processor of the computing device 166. In several embodiments, a portion of event data is generated by a processor of a monitoring device, another portion of the event data is generated by a processor of the computing device 166, and the remaining portion is generated by a processor of the server 228. In various embodiments, a portion of event data is generated by a processor of a monitoring device, another portion of the event data is generated by a processor of the computing device 166, and the remaining portion is generated by a virtual machine. In some embodiments, a portion of event data is generated by a processor of a monitoring device and the remaining portion is generated by a virtual machine or by the server 228. In various embodiments, a portion of event data is generated by a processor of the computing device 166 and the remaining portion is generated by a virtual machine or by the server 228.

FIG. 7A is an embodiment of the GUI 370 that displays the events $126_1$ thru $126_{10}$. In some embodiments, the processor 234 (FIG. 3A) highlights, e.g. bolds, colors, shades, etc., an activity level that is higher than or lower than the remaining activity levels by a threshold. The highlight distinguishes the activity level from one or more activity levels of one or more events that occur during a period of time. For example, the processor 234 provides a different color to an activity level 402 compared to remaining activity levels of the event $126_{10}$ when the processor 234 determines that the activity level 402 is greater than the remaining activity levels by a threshold.

The GUI 370 is rendered by the processor 234 of the monitoring device 108A to be displayed on the display device 276 (FIG. 3A) of the monitoring device 108A or by the processor 226 (FIG. 5) of the computing device 166 to be displayed on the display device 352 (FIG. 5) of the computing device 166.

The processor 234 or the processor 226 combines amounts of time of a common activity over one or more periods of time to indicate a combined amount of time, e.g., a combined amount of time $138_1$, a combined amount of time $138_2$, a combined amount of time $138_3$, a combined amount of time $138_4$, etc., of performance of the common activity and a level, e.g., a level $140_1$, a level $140_2$, a level $140_3$, a level $140_4$, etc., of the common activity performed. For example, as shown in FIG. 7A, the user 112A drove a vehicle for 1 hour and 1 minute on a date 308 of March 1, Thursday. As another example, the processor 234 or the processor 226 sums periods of time for which the user 112A performed the common activity on the date 308. To illustrate, a period of time of occurrence of the event $126_2$, a period of time of occurrence of the event $126_5$, a period of time of occurrence of the event $126_7$, and a period of time of occurrence of the event $126_9$ are summed to determine a total time period of occurrence of a common activity of driving a vehicle.

Examples of a common activity are the same as that of an activity except that the common activity is the same over multiple periods of time. For example, a common activity is walking, running, golfing, etc.

In various embodiments, the processor 234 or the processor 226 combines activity levels of performance of the common activity over the combined amount of time to generate a combined activity level for each common activity. For example, activity levels of the event $126_2$, activity levels of the event $126_5$, activity levels of the event $126_7$, and activity levels of the event $126_9$ are summed to generate a combined activity level of a common activity of driving over the total time period to generate a combined activity level $140_4$. Similarly, other combined activity levels $140_1$, $140_2$, and $140_3$ are generated.

Moreover, in some embodiments, the processor 234 or the processor 226 combines amounts of time of one or more activities performed at a common location over one or more periods of time to generate a combined amount of time, e.g., a combined amount of time $138_5$, a combined amount of time $138_6$, a combined amount of time $138_7$, etc., of performance of the one or more activities at the common location. For example, time of performance of all activities performed at a home of the user 112 on the date 308 are combined to generate the combined amount of time $138_5$. As another example, time of performance of all activities performed at an office of the user 112 on March 1 are combined to generate the combined amount of time $138_6$. A common location is a location at which one or more activities, e.g., a common activity, etc., are performed over one or more periods of time.

In several embodiments, the processor 234 or the processor 226 combines activity levels of performance of the one or more activities at the common location over a combined amount of time to generate a combined activity level, e.g., a combined activity level $140_5$, a combined activity level $140_6$, a combined activity level $140_7$, etc., of one or more activities performed at the common location. For example, activity levels of an activity of walking done by the user 112A at a home of the user 112A on the date 308 are combined to generate the combined activity level $140_5$. As another example, activity levels of one or more activities performed during the events $126_1$, $126_6$, and $126_{10}$ are combined to generate the combined activity level $140_5$.

The GUI 370 further includes a reverse button 410 and a forward button 412. The user 112A selects the reverse button 410 via the user interface 274 (FIG. 3A) or via the input device 340 (FIG. 5) to view a GUI that displays one or more events, one or more combined activity levels, and/or one or more combined amounts of time on a date prior to the date 308. Similarly, the user 112A selects the forward button 412 via the user interface 274 (FIG. 3A) or via the input device 340 (FIG. 5) to view a GUI that displays one or more events, one or more combined activity levels, and/or one or more combined amounts of time on a date after the date 308.

In various embodiments, the GUI 370 includes a time at which there is a change in an activity level beyond a limit in an amount of time. For example, the GUI 370 includes a wake-up time 414 and a bed time 416. The position sensor 220 (FIG. 3A) determines an amount of activity and based on the amount, the processor 234 or the processor 226 determines whether the amount of activity has crossed the limit in an amount of time. Upon determining that the amount of activity has crossed the limit in an amount of time, the processor 234 or the processor 226 indicates, e.g., highlights, etc., a time at which the level is crossed on the GUI 370. For example, the processor 234 highlights the wake-up time 414 and the bed time 316.

It should be noted that a GUI generated by the processor 234 is displayed on the display device 276 (FIG. 3A), a GUI generated by the processor 302 is displayed on the display device 304 (FIG. 3B), and a GUI generated by the processor 226 is displayed on the display device 352 (FIG. 5).

It should further be noted that in some embodiments, any GUI described herein as being generated by the processor 234 or by the processor 226 for display may instead be generated by the processor 302 of the monitoring device 108B for display on the display device 304.

In some embodiments, event data includes an environmental parameter that is received from the environmental sensor 272 of the monitoring device 108A by the processor 234 (FIG. 3A) or from the environmental sensor 292 of the monitoring device 108B by the processor 302 (FIG. 3B) or from the environmental sensor 272 via the wireless communication device 278 (FIG. 3A) of the monitoring device 108A by the NIC 356 (FIG. 5) of the computing device 166 or from the environmental sensor 292 via the wireless communication device 300 (FIG. 3A) of the monitoring device 108B by the NIC 356 (FIG. 5) of the computing device 166.

In several embodiments, the processor 226 or the processor 234 does not generate event data when an activity of the event data occurs for less than a period of time, e.g., two minutes, three minutes, etc.

In a number of embodiments, the processor 226 or the processor 234 replaces a current location identifier with a previous and a future location identifier when the user 112A is at the previous, current, and future locations within a time limit and when the previous location identifier and the future location identifier are the same. The previous location is a location at which the user 112A was before arriving at the current location. The current location is a location at which the user 112A is before the user 112A arrives at the future location. For example, the processor 234 determines based on the correspondence between one or more geo-locations, one or more positions of the user 112A, and the previous location and based on the correspondence between one or more geo-locations, one or more positions of the user 112A, and the future location that the previous location and the future location are the same.

In this example, the processor 234 further determines that the current location is different from the previous and future locations and the user 112A has arrived at the previous, current, and future locations within a time limit that is received from the time measurement device 232. In this example, the processor 234 determines that the current location is different from the previous locations based on the correspondence between one or more geo-locations, one or more positions of the user 112A, and the previous location and based on the correspondence between one or more geo-locations, one or more positions of the user 112A, and the future location and based on the correspondence between one or more geo-locations, one or more positions of the user 112A, and the current location. In this example, the processor 234 determines that the current location is the same as the previous and future locations upon determining that the previous and future locations are the same and that the user 112A arrives at the previous, current, and future locations within the time limit.

In several embodiments, the processor 226 or the processor 234 replaces a current activity identifier with a previous and a future activity identifier when the user 112A performs the previous, current, and future activities within a time limit and when the previous activity identifier and the future activity identifier are the same. The previous activity is an activity that the user 112A performs before performing the current activity and the current activity is an activity that the user 112A performs before performing the future activity. For example, the processor 234 determines based on positions of the user 112A and/or geo-location data of the user 112A that the previous activity and the future activity are the same and that the current activity is different from the previous and the future activities. In this example, the processor 234 further determines that the previous, current, and future activities are performed within a time limit that is received from the time measurement device 232. In this example, the processor 234 determines that the current activity is the same as the previous and future activities upon determining that the previous and future activities are the same and that the user 112A performs the previous, current, and future activities within the time limit.

In some embodiments, the processor 226 or the processor 234 applies a Markov model to determine whether to replace the current location identifier that is different from the previous and future location identifiers with the previous or future location identifier. In a number of embodiments, the processor 226 or the processor 234 applies a Markov model to determine whether to replace the current activity identifier that is different from the previous and future activity identifiers with the previous or future activity identifier.

In some embodiments, a user resizes and/or repositions an overlay, e.g., an activity identifier, a location identifier, etc., to improve the precision of an event. For example, an overlay indicates that the user 112A is performing an activity at a first activity level at a time. The user 112A changes a position and/or size of the overlay to indicate that the user 112A is performing the activity at a second activity level at the time. The first and second activity levels are displayed within the same GUI. The user 112A changes a position and/or size of an overlay via an input device of the computing device 166 or via a user interface of a monitoring device.

FIG. 7B is a diagram of a GUI 420 that is generated by executing the method 102 (FIG. 6A), 160 (FIG. 6B), 170 (FIG. 6C), 210 (FIG. 6E), or 221 (FIG. 6F). A map 422 includes a location, e.g., an aquarium, etc., visited by the user 112A and further includes a route to the location. The map 422 is displayed within the GUI 420. The map 422 is generated based on geo-location data. Moreover, the GUI 420 includes a timeline 423 of activities performed by the user 112A on a date 424 of Mar. 1, 2012. The date 424 is displayed within the GUI 420 on top of the map 422.

The user 112A selects the date 424 among multiple dates displayed on top of the map 422 via the user interface 274 (FIG. 3A) of the monitoring device 108A or via the input device 340 (FIG. 5) of the computing device 166. When the date 424 is selected, the processor 234 of the monitoring device 108A (FIG. 3A) generates the GUI 420 to display the GUI 420 on the display device 276 (FIG. 3A) or the processor 226 (FIG. 5) of the computing device 166 generates the GUI 420 to display the GUI 420 on the display device 352 (FIG. 5) of the computing device 166.

The GUI 420 includes events $424_1$, $424_2$, $424_3$, $424_4$, $424_4$, $424_5$, $424_6$, and $424_7$. The event $424_4$ includes activity levels of an activity performed at the aquarium by the user 112A.

FIG. 7C is a diagram illustrating a method for establishing boundaries between two locations over one or more periods of time. A boundary is a boundary of a location. A boundary also indicates a time at which the user 112A enters or exits a location having the boundary. For example, a boundary A includes outside walls of a home of the user 112A and a time at which the user 112A enters the home or exits the home. As another example, a boundary B includes outside walls of a building where the user 112A works and a time at which the user 112A enters the building or leaves the building. As yet another example, a boundary C includes outside walls of a sandwich shop and a time at which the user 112A enters the sandwich shop or leaves the sandwich shop. As another example, a boundary D includes a line that limits an area of a golf course and a time at which the user 112A enters the golf course or leaves the golf course. As an example, a boundary E includes a body of a vehicle and a time at which the user 112A enters the vehicle or leaves the vehicle.

The processor 234 of the monitoring device 108A (FIG. 3A) or the processor 226 (FIG. 5) of the computing device 166 determines boundaries where the user 112A arrives at, e.g., enters, etc., and departs from, e.g., exits, etc., a location. For example, the processor 234 receives from the device locator 222 (FIG. 3A) a geo-location 1 of the monitoring device 108A. Continuing with the example, the processor 234 determines that the geo-location 1 corresponds to a location 1, e.g., a street, a vehicle, etc., outside a location 2, e.g., a building, a street, etc. The location 2 corresponds to a geo-location 2. The processor 234 determines that the user 112A is at the location 1 at a time tx and at the location 2 at a time ty. In this example, the processor 226 receives the geo-location 1 from the device locator 222 and the geo-location 2 from the device locator 222 and the times tx and ty from the time measurement device 232 (FIG. 3A). In this example, there is a lack of geo-location data of the user 112A between the times tx and ty.

In the example, the processor 234 further determines a speed of an activity of the user 112A performed at the time tx or at the time ty. The processor 234 determines a speed of the user 112A between the times tx and ty. Further, in this example, the processor 234 calculates speed as a ratio of a distance between the geo-locations 2 and 1 and a difference between the times ty and tx. In this example, based on the speed, the processor 226 determines an amount of time taken by the user 112A to reach an entry of the location 2. A geo-location corresponding to the entry of the location 2 is obtained from the device locator 222 by the processor 234 and/or an amount of movement corresponding to the entry of the location 2 is obtained from the position sensor 220 of the monitoring device 108A, and the entry is determined from geo-location, the amount of movement, and/or the geo-location-location database by the processor 234. In this example, the processor 234 adds the amount of time taken to reach the entry from the time tx to determine a time of entry by the user 112A into the location 2 from the location 1.

It should be noted that the processor 234 of the monitoring device 108A or the processor 226 of the computing device 166 determines geo-location data as located along a straight line between two boundaries. For example, geo-location data is located on a straight line 440 between the boundary A and the boundary B, geo-location data is located on a straight line 442 between the boundary B and the boundary C, and geo-location data is located on a straight line 444 between a point 448 and the boundary D.

In some embodiments, geo-location data is determined for minute time intervals, e.g., times between the times tx and ty, every minute, every fraction of a minute, etc., is compared to the geo-location data on a straight line between two boundaries or between a boundary and a point. The processor 234 or the processor 226 performs the comparison. The geo-location data determined for the minute time intervals may be decimated by the processor 234 or the processor 226. The processor 234 or the processor 226 determines whether a divergence between the geo-location data obtained at the minute time intervals and geo-location data on a straight line between two boundaries exceeds a value. Upon determining that the divergence exceeds the value, the processor 234 or the processor 226 determines that there is a boundary at a point of the divergence.

For example, a divergence between geo-location data on the straight line 440 and geo-location data, obtained at minute time intervals, on a curve 446 exceeds a value. In this example, the boundary A exists at a point of the divergence. On the other hand, upon determining that the divergence does not exceed the value, the processor 234 or the processor 226 determines that there is no boundary at the point of lack of divergence. For example, a divergence between geo-location data on the straight line 444 and geo-location data, obtained at minute time intervals, on a straight line 446 does not exceed the value. In this example, there is no boundary formed at the point 448 at which the lines 444 and 446 start to intersect.

FIG. 7D is a diagram of a GUI 460 to illustrate a method of allowing a user to choose a location in case of common geo-locations between multiple locations. The GUI 460 is generated by executing the method 221 (FIG. 6F). As shown in the GUI 460, the processor 234 or the processor 226 determines that a location 462 and a location 464 has one or more common geo-locations 466. The locations 462 and 464 may be determined by the processor 226 or the processor 234 based on the geo-location-location database. The processor 234 generates a prompt and displays the prompt via the display device 276 (FIG. 3A) to the user 112A. Similarly, the processor 226 generates the prompt to display via the display device 352 (FIG. 5). The prompt indicates to the user 112A to select the location 462 or the location 464 as a location corresponding to the geo-locations 466. The user 112 selects via the user interface 274 (FIG. 3A) or via the input device 340 (FIG. 5) the location 462 or the location 464 as corresponding to the geo-locations 466. Upon receiving the selection of the location 462 or the location 464, the processor 226 or the processor 234 associates the selected location to correspond to the geo-locations 466.

In various embodiments, instead of a prompt, a notification, e.g., a prompt, an email, an update, an increment in a number, a message, etc., is generated to display on a display device.

In several embodiments, a notification includes an invitation to meet at a location to perform one or more activities at the location. For example, an invitation is sent from the user account 912 to the user account 174 requesting the user 112A permission to meet at a location, e.g., park, gym, etc., to perform an activity, e.g., swim, run, walk, etc. The user 112A may accept or reject the invitation via the user account 174.

In various embodiments, a notification includes a request for permission to post data that the user 112B is performing an activity at a location with the user 112A. For example, the request includes a permission to indicate that user 112B is walking with the first user 112B at a park. As another example, the request includes a permission to indicate that user 112B is exercising with the first user 112B at a gym. The permission may include a website on which the data is to be posted. The website may be a social network website, a web site owned by the user 112B, or a website that is associated with maintaining event data, e.g., a website having the web address 1, a website having the web address 2, or a website having the web address 3, etc.

In some embodiments, the user 112A expands a size of the location 462 via the user interface 274 (FIG. 3A) to indicate to include one or more geo-locations within the location 466 to indicate to the processor 226 that the one or more geo-locations within the location 466 are within the location 462. The processor 226 then associates the one or more geo-locations with the location 462 instead of with the location 466.

In various embodiments, one or more geo-locations are located outside the location 466. The user 112A expands a size of the location 462 via the user interface 274 (FIG. 3A) to indicate to include the one or more geo-locations to indicate to the processor 226 that the one or more geo-locations are within the location 462. The processor 226 then associates the one or more geo-locations with the location 462.

FIG. 7E is a diagram of an embodiment of a web page 470 that includes the GUI 394 that further includes the events $128_1$, $128_2$, $128_3$, $128_4$, $128_5$, and $128_6$. The GUI 394 is similar to the GUI 370 (FIG. 7A) except that the GUI 394 is displayed within the web page 470 and the GUI 394 includes a time 337 of exit by the user 112A of his/her home. In some embodiments, the GUI 394 includes a time of entry or exit by the user 112A of a location.

A web page is displayed when the wireless communication device 278 (FIG. 3A) or a wired communication device of the monitoring device 108A sends a request for the web page to the server 228 via the network 176 without using the computing device 166 (FIG. 3A). In some embodiments, the request for a web page is sent from the NIC 356 of the computing device 166 via the network 176 to the server 228.

Upon receiving the request for a web page, the server 228 sends the web page via the network 176 to the computing device 166. The NIC 356 of the computing device receives a web page and the web page is displayed on the display device 352 (FIG. 5) of the computing device 166.

Similarly, in some embodiments, upon receiving the request for a web page, the server 228 sends the web page via the network 176 to the monitoring device 108A. The wireless communication device 278 (FIG. 3A) or a wired communication device of the monitoring device 108A receives a web page and the web page is displayed on the display device 276 (FIG. 3A) of the monitoring device 108A.

Figure 7F:
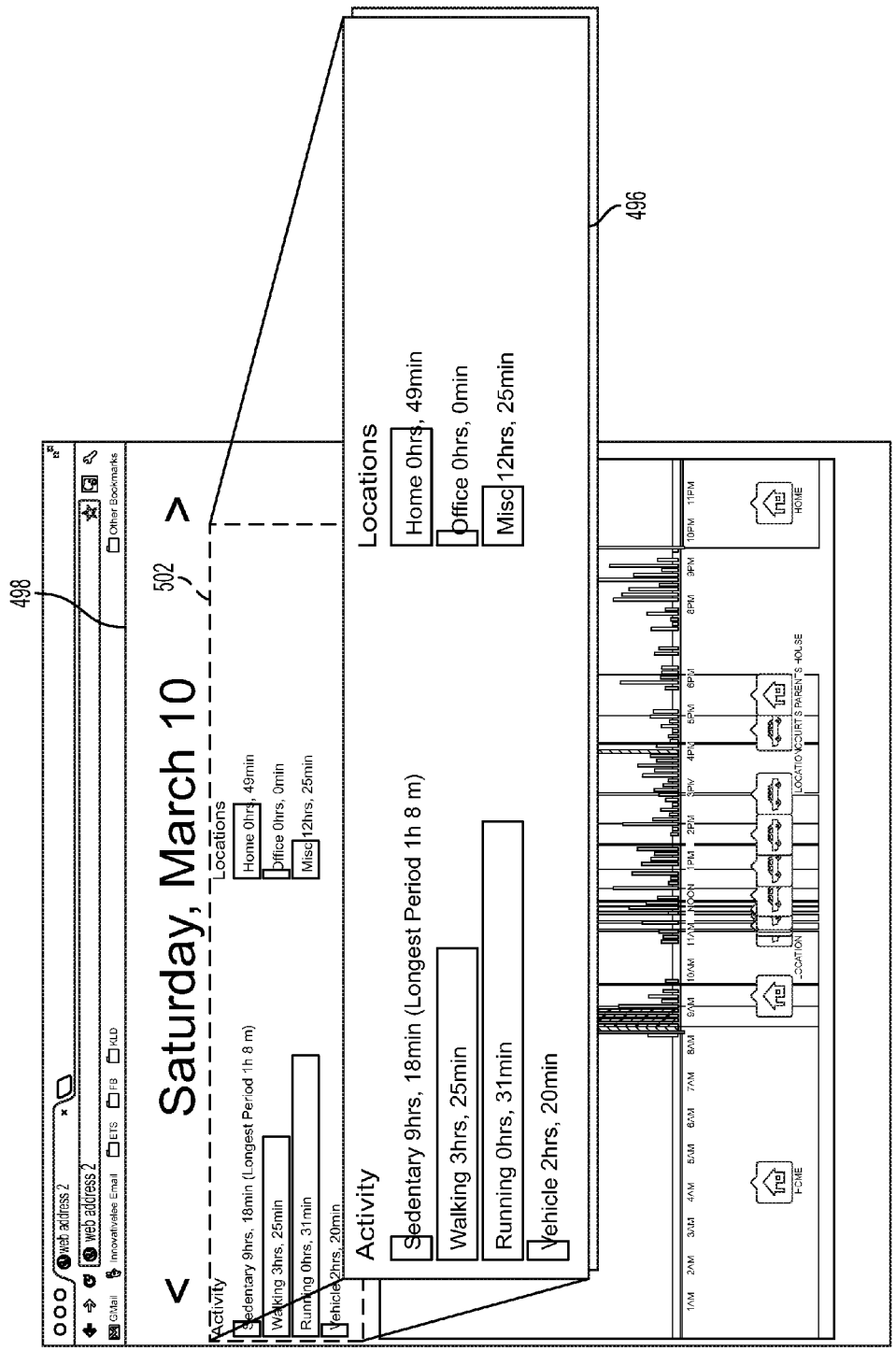
FIG. 7F is a zoom-in of a portion of a GUI to illustrate activity levels of one or activities performed by a user over a period of time and to illustrate activity levels associated with one or more locations at which the activities are performed, in accordance with one embodiment described in the present disclosure.

FIG. 7F is a diagram of an embodiment of a zoom-in 496 of a portion 502 of a GUI 498. The GUI 496 is generated by executing the method 102 (FIG. 6A), 160 (FIG. 6B), 170 (FIG. 6C), or 210 (FIG. 6E). In some embodiments, the zoom-in 496 is displayed on the display device 276 (FIG. 3A) of the monitoring device 108A or on the display device 352 (FIG. 5) of the computing device 166. The zoom-in 496 is displayed when the user 112A selects the portion 502 via the user interface 274 (FIG. 3A) or via the input device 340 (FIG. 5).

Figure 7G:
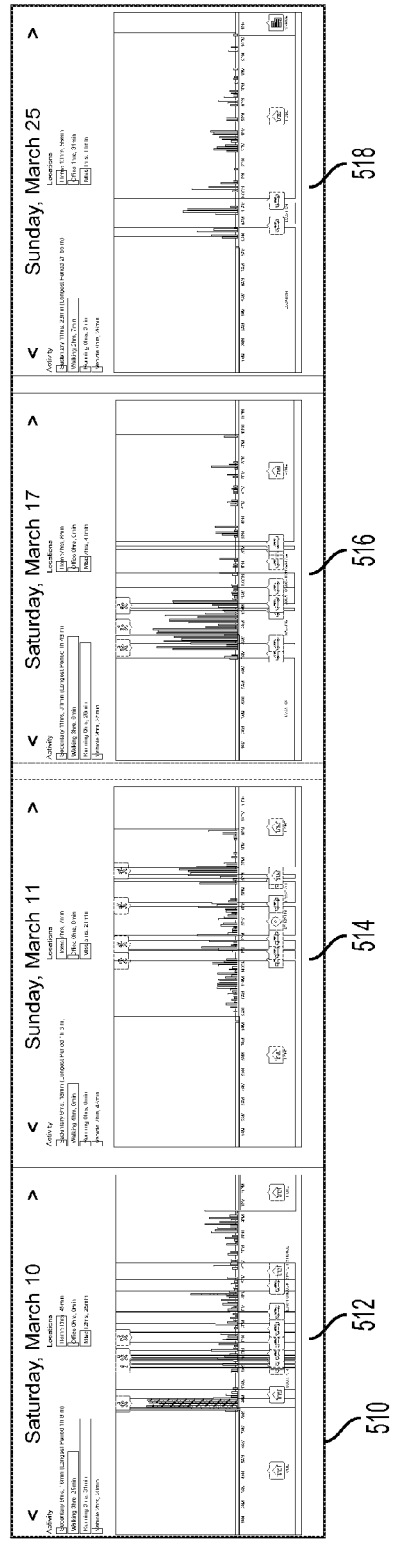
FIG. 7G is a diagram of a daily journal GUI that includes one or more GUIs that include event data for periods of time, in accordance with one embodiment described in the present disclosure.

FIG. 7G is a diagram of an embodiment of a daily journal GUI 510. The daily journal GUI 510 is generated when the processor 234 or the processor 226 combines one or more GUIs 512, 514, 516, and 518. Each GUI 512, 514, 516, and 518 is generated by executing the method 102 (FIG. 6A), 160 (FIG. 6B), 170 (FIG. 6C), or 210 (FIG. 6E). The GUIs 512, 514, 516, and 518 have chronologically-ordered dates of one or more activities performed by the user 112A at one or more locations over one or more periods of time. In some embodiments, the GUIs 512, 514, 516, and 518 have consecutive dates, which are dates of activities performed by the user 112A. The daily journal GUI 510 is displayed by the processor 234 on the display device 276 (FIG. 3A) of the monitoring device 108A or is displayed by the processor 226 on the display device 352 (FIG. 5) of the computing device 166.

Each GUI 512, 514, 516, and 518 is displayed in a row. In some embodiments, each GUI 512, 514, 516, and 518 is displayed in a column or parallel to an oblique line.

Figure 7H:
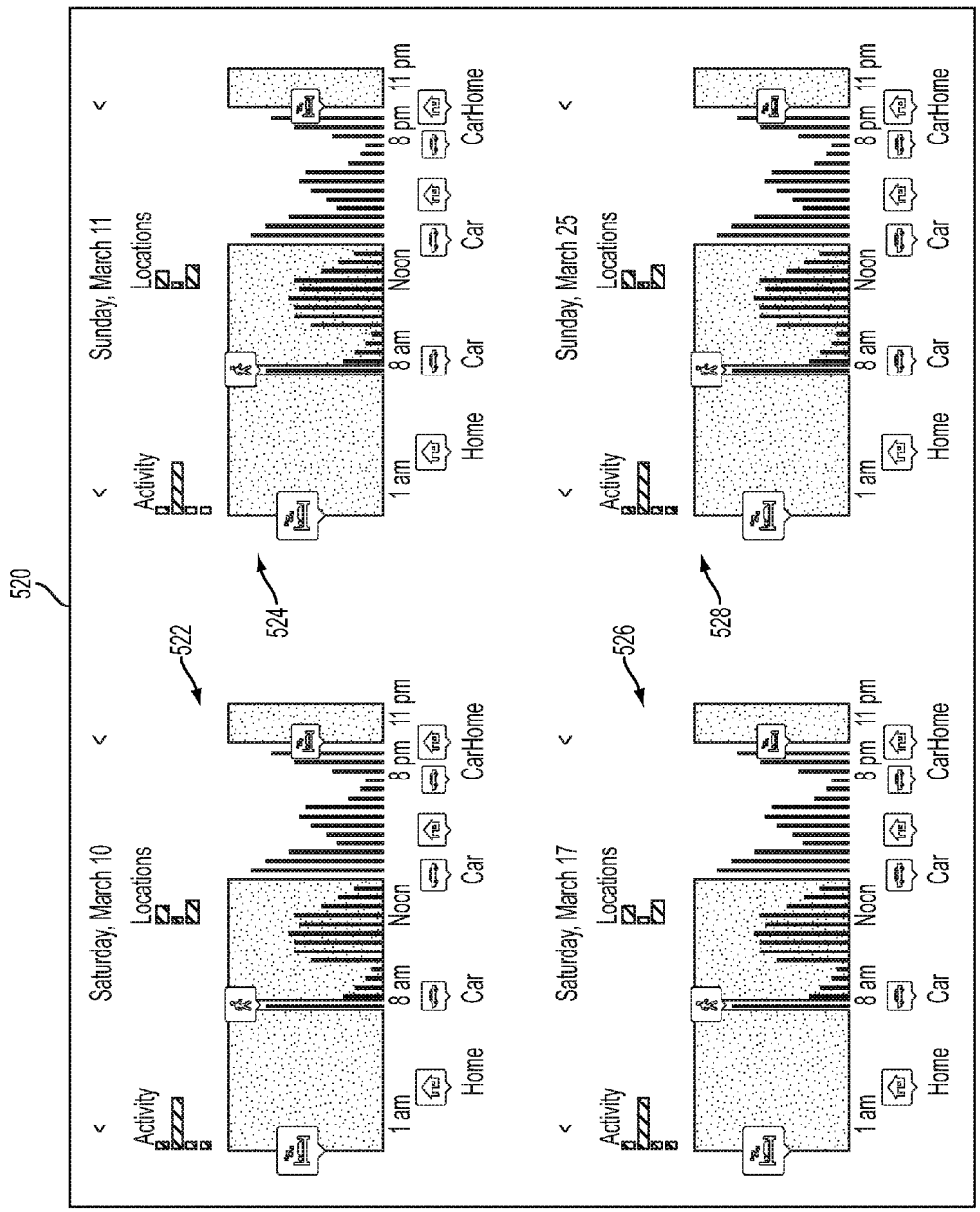
FIG. 7H is a diagram of another daily journal GUI that includes one or more GUIs that include event data for periods of time, in accordance with one embodiment described in the present disclosure.

FIG. 7H is a diagram of an embodiment of a daily journal GUI 520. The daily journal GUI 520 is generated when the processor 234 or the processor 226 combines one or more GUIs 522, 524, 526, and 528. Each GUI 522, 524, 526, and 528 is generated by executing the method 102 (FIG. 6A), 160 (FIG. 6B), 170 (FIG. 6C), or 210 (FIG. 6E). The GUIs 522, 524, 526, and 528 have chronologically-ordered dates of one or more activities performed by the user 112A at one or more locations over one or more periods of time. In some embodiments, the GUIs 522, 524, 526, and 528 have consecutive dates, which are dates of activities performed by the user 112A. The daily journal GUI 520 is displayed by the processor 234 on the display device 276 (FIG. 3A) of the monitoring device 108A or is displayed by the processor 226 on the display device 352 (FIG. 5) of the computing device 166.

Each GUI 522, 524, 526, and 528 is displayed in an orderly fashion.

Figure 7I:
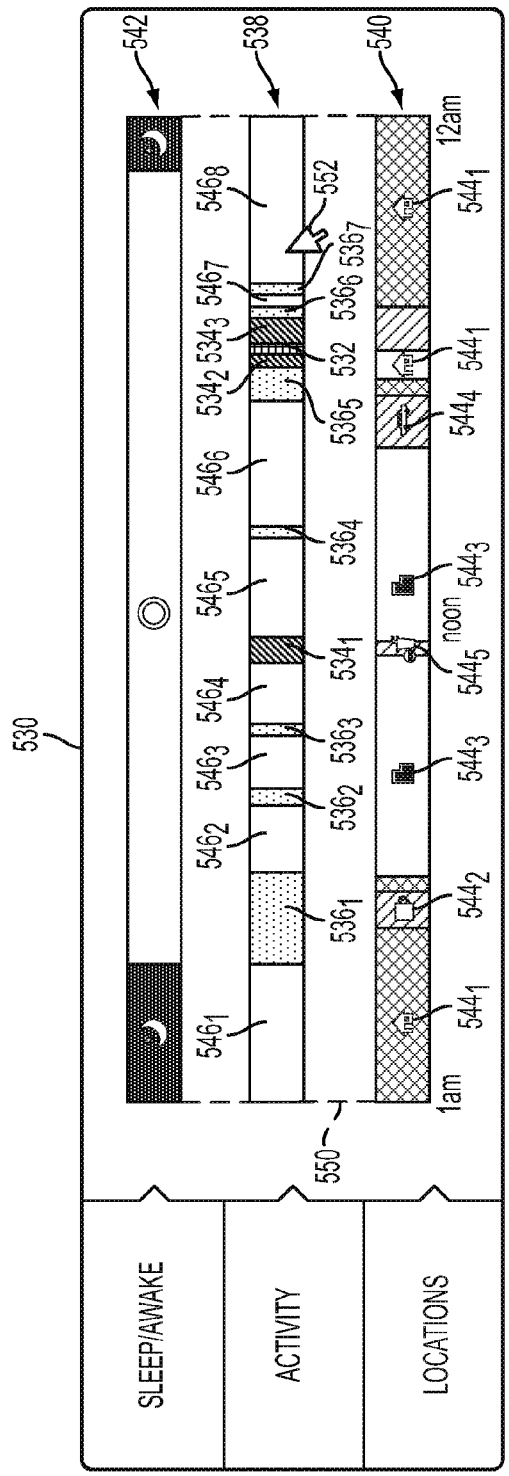
FIG. 7I is a GUI that provides an overview of one or more levels of one or more activities performed by a user at one or more locations over a period of time, in accordance with one embodiment described in the present disclosure.

FIG. 7I is a diagram of an embodiment of a GUI 530 that provides an overview of one or more activities 538 performed by the user 112A at one or more locations 540 over a period of time. The activities 538 are graphical elements. Similarly, the locations 540 are graphical elements. The GUI 530 is generated by executing the method 102 (FIG. 6A), 160 (FIG. 6B), 170 (FIG. 6C), or 210 (FIG. 6E). The GUI 530 also includes a time line 542 that shows a relationship of time periods, e.g., a night time period, a day time period, etc., with performance of the activities 538 and the locations 540. The activities 538, the locations 540, and the time line 542 are aligned with respect to each other along a column 550. The locations 540 include one or more location/activity identifiers $544_1$, $544_2$, $544_3$, and $544_4$.

The activities 538 include a sedentary activity $546_1$, a sedentary activity $546_2$, a sedentary activity $546_3$, a sedentary activity $546_4$, a sedentary activity $546_4$, a sedentary activity $546_5$, a sedentary activity $546_6$, a sedentary activity $546_7$, and a sedentary activity $546_8$. The activities 538 further include a lightly active activity $536_1$, a lightly active activity $536_2$, a lightly active activity $536_3$, a lightly active activity $536_4$, a lightly active activity $536_5$, a lightly active activity $536_6$, and a lightly active activity $536_7$. The activities 538 further includes a moderately active activity $534_1$, a moderately active activity $534_2$, a moderately active activity $534_3$, and a highly active activity $532$.

It should be noted that an activity level of the sedentary active activity is lower than an activity level of the lightly active activity. An activity level of the lightly active activity is lower than an activity level of the moderately active activity and an activity level of the moderately active activity is lower than an activity level of the highly active activity. For example, a number of calories burned during the sedentary active activity is lower than a number of calories burned during the lightly active activity, a number of calories burned during the lightly active activity is lower than a number of calories burned during the moderately active activity, and a number of calories burned during the moderately active activity is lower than a number of calories burned during the highly active activity. As another example, an amount of activity performed at the sedentary active activity is lower than an amount of activity performed at the lightly active activity, an amount of activity performed at the lightly active activity is lower than an amount of activity performed at the moderately active activity, and an amount of activity performed at the moderately active activity is lower than an amount of activity performed at the highly active activity.

Each activity is vertically aligned with a location. For example, the sedentary activity $546_1$ is vertically aligned with the location $544_1$. As another example, the lightly active activity $536_1$ is vertically aligned with the locations $544_1$ and $544_2$.

In some embodiments, when an activity is aligned, e.g., vertically, horizontally, etc. with a location, the activity is performed at the location. For example, the monitoring device 108A worn by the user 112A captures positions used to determine an activity performed within a home of the user 112A.

Moreover, it should be noted that although four activities are shown in FIG. 7I, in some embodiments, any number of activities may be shown. Furthermore, in some embodiments, the activities 538, the locations 540, and the time line 542 are aligned with respect to each other along a row instead of the column 550. For example, each of the activities 538, the locations 540, and the time line 542 are made vertical instead of horizontal to be aligned with respect to each other along a row.

A cursor 552 is displayed on the GUI 530 by the processor 226 or by the processor 234. When the user 112A uses the user interface 274 (FIG. 3A) or the input device 340 (FIG. 5) to point the cursor 552 to a portion of the activities 538 and selects the portion, a progressively detailed GUI 560 is displayed. The GUI 560 is displayed in FIG. 7J.

Figure 7J:
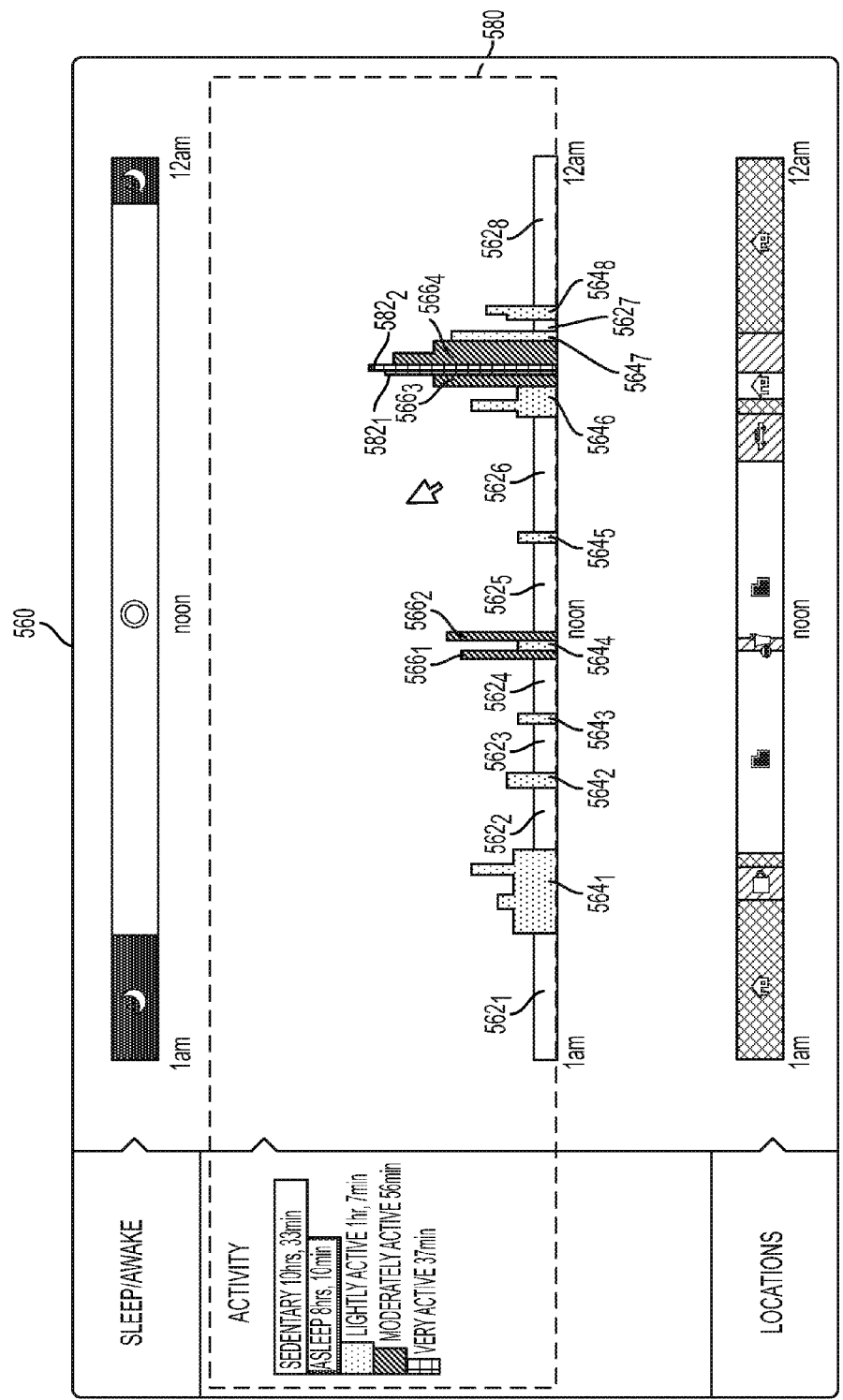
FIG. 7J is a diagram of a GUI that includes a detailed view of activities displayed in the GUI of FIG. 7I, in accordance with one embodiment described in the present disclosure.

FIG. 7J is a diagram of an embodiment of the GUI 560. The GUI 560 is generated by executing the method 102 (FIG. 6A), 160 (FIG. 6B), 170 (FIG. 6C), or 210 (FIG. 6E). The GUI 560 includes a detailed view of the activities 538 (FIG. 7I) The detailed view is shown as activities 580. For example, the GUI 560 includes a detailed view of each activity level of the GUI 530 (FIG. 7I). To illustrate, the highly active activity 532 (FIG. 7I) is detailed as one or more highly active activity levels $582_1$ and $582_2$ of the activity. As another illustration, the sedentary activities $546_1$ thru $546_8$ are detailed as one or more sedentary activity levels $562_1$, $562_2$, $562_3$, $562_4$, $562_5$, $562_6$, $562_7$, and $562_8$. As yet another illustration, the lightly active activities $536_1$ thru $536_7$ are detailed as one or more lightly active activity levels $564_1$, $564_2$, $564_3$, $564_4$, $564_5$, $564_6$, $564_7$, and $564_8$. As another illustration, the moderately active activities $534_1$ thru $534_3$ are detailed as one or more moderately active activity levels $566_1$, $566_2$, $566_3$, and $566_4$. In some embodiments the activities 580 are graphical elements.

In some embodiments, each location/activity identifier of the GUI 530 is detailed by the processor 226 or by the processor 234 into a detailed location/activity identifier within the GUI 560. For example, a building identifier within the GUI 530 is detailed, within the GUI 560 into one or more rooms of the building when the user 112A uses the user interface 274 (FIG. 3A) or the input device 340 (FIG. 5) to point the cursor 552 to a portion of the locations 540 (FIG. 7I) and to select the portion.

In various embodiments, the GUI 560 includes a detailed view, which includes one or more activity levels, of an activity of the GUI 530. The activity of the GUI 530 is one at which the user 112A points to and selects with the pointer 552. In some embodiments, the GUI 560 includes a detailed location/activity identifier of a location/activity identifier, on the GUI 530, at which the user 112A points to and selects with the pointer 552.

Figure 7K:
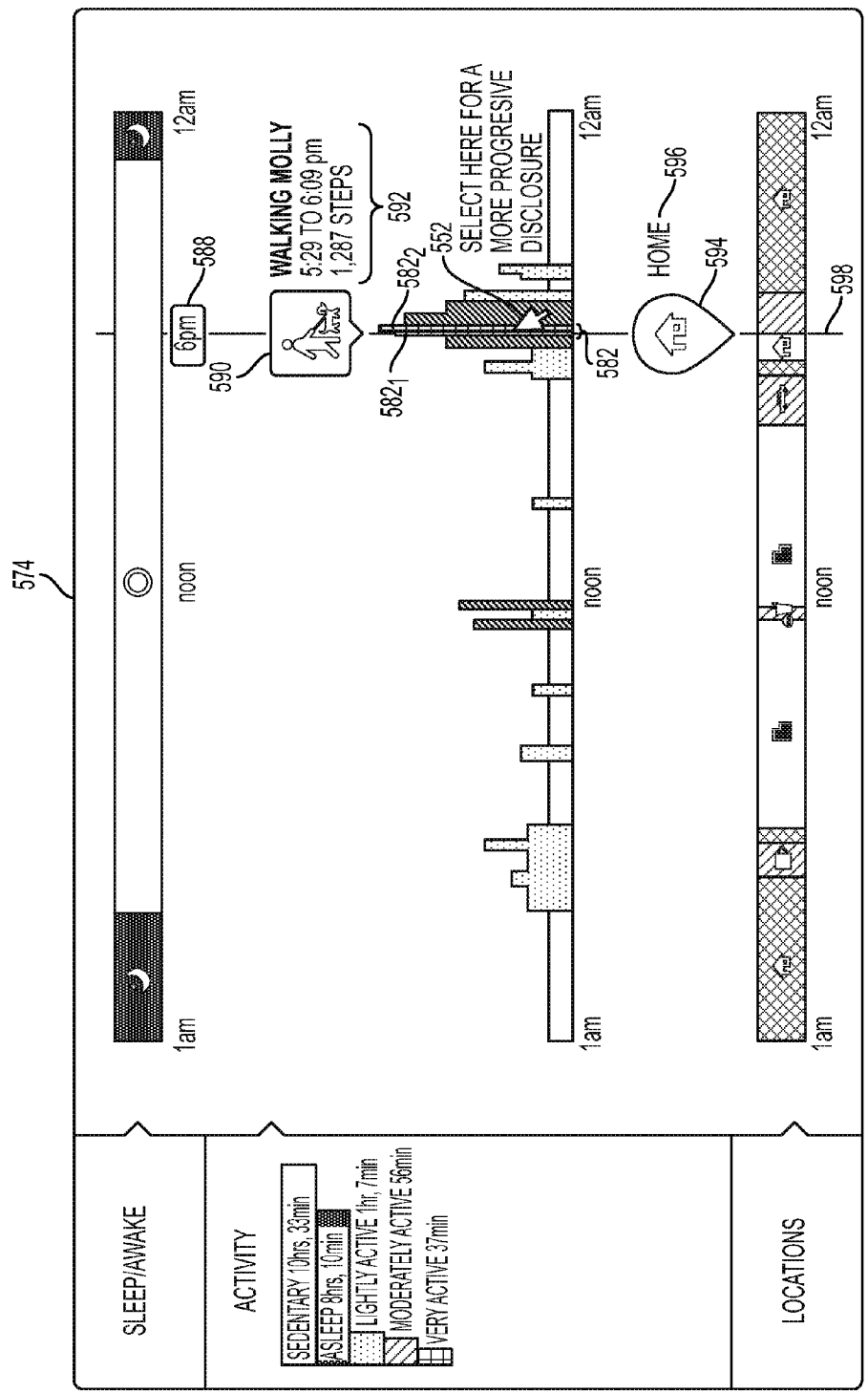
FIG. 7K is a diagram of a GUI that includes a more detailed view of activities displayed in the GUI of FIG. 7J, in accordance with one embodiment described in the present disclosure.

FIG. 7K is a diagram of an embodiment of the GUI 574. The GUI 574 is the same as the GUI 560 (FIG. 7J) except that the GUI 574 shows a more detailed view of one or more activities performed by the user 112A, of a time period during which the activities are performed, and/or of a location at which the activities are performed, compared to that shown in the GUI 560. For example, when the user 112A uses the user interface 274 (FIG. 3A) or the input device 340 (FIG. 5) to point the cursor 552 to a portion, e.g., an activity level $582_1$ (FIG. 7J), etc., of the activities 580 (FIG. 7J) and to select the portion, a detailed view of the portion is displayed within the GUI 574. To illustrate, the detailed view of the portion includes a graphical element 588 that displays a time at which the activity level $582_1$ occurs, a location/activity identifier 590 identifying an activity, e.g., walking, running, etc., performed at a location by the user 112A. The activity level $582_1$ and an activity level $582_2$ are portions of an activity level 582.

The detailed view further includes text 592 that describes the activity, having the activity level $582_1$, performed by the user 112A, time of occurrence of the activity, and activity data, e.g., number of steps, calories burned, etc., of the activity. The detailed view further includes a location/activity identifier 594 that represents a location closest to a location of performance of the activity identified by the location/activity identifier 590. For example, the location/activity identifier 594 is a home icon of a home of the user 112A and the home is at a location closest to a location where the user 112A walks a dog. The detailed view further includes text 596 describing a location identified by the location/activity identifier 594. The graphical element 588, the location/activity identifier 590, and the location/activity identifier 594 are aligned along a line 598. In some embodiments, the graphical element 588, the location/activity identifier 590, and the location/activity identifier 594 are not aligned with respect to each other. In various embodiments, the detailed view excludes the text 592 and/or excludes the text 596. In several embodiments, the detailed view excludes the location/activity identifier 590 and/or excludes the location/activity identifier 596. The GUI 574 is generated by executing the method 102 (FIG. 6A), 160 (FIG. 6B), 170 (FIG. 6C), or 210 (FIG. 6E).

Figure 7L:
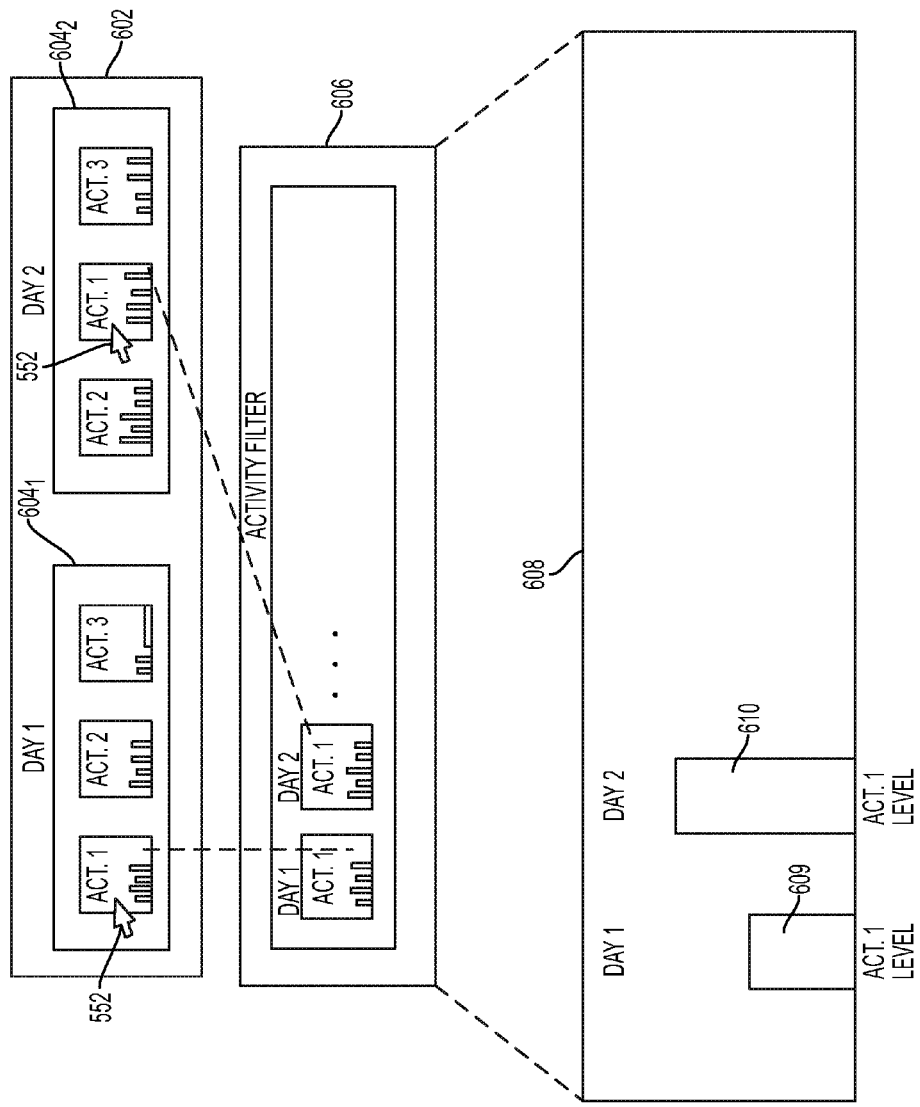
FIG. 7L is a diagram illustrating a method of combining activity levels over a period of time, in accordance with one embodiment described in the present disclosure.

FIG. 7L is a diagram illustrating an embodiment of a method of combining activity levels over a period of time. The method of combining activity levels over a period of time is performed by the processor 226 or by the processor 234. In the method of combining activity levels, a GUI 602 is displayed by the processor 226 or by the processor 234.

The GUI 602 includes a display 604₁ of activity levels of a number of activities, e.g., an activity 1, an activity 2, and an activity 3, etc. performed by the user 112A during a day 1. The activities shown in the display 604₁ are performed in the order shown. For example, the activity 1 is performed during the day 1 before the activity 2 is performed during the day 1 and the activity 2 is performed during the day 1 before the activity 3 is performed during the day 1.

Moreover, the GUI 602 includes a display 604₂ of activity levels of a number of activities, e.g., an activity 2, an activity 1, and an activity 3, etc. performed by the user 112A during a day 2. The activities shown in the display 604₂ are performed in the order shown. For example, the activity 2 is performed during the day 2 before the activity 1 is performed during the day 2 and the activity 1 is performed during the day 2 before the activity 3 is performed during the day 2.

The user 112A uses the user interface 274 (FIG. 3A) or the input device 340 (FIG. 5) to point the cursor 552 to the activity 1 performed during the day 1 to select the activity 1 performed during the day 1 and drag the activity 1 performed during the day 1 to a GUI 606, which is an activity filter. The user 112A then uses the user interface 274 (FIG. 3A) or the input device 340 (FIG. 5) to point the cursor 552 to the activity 1 performed during the day 2 to select the activity 1 performed during the day 2 and drag the activity 1 performed during the day 2 to the GUI 606. In some embodiments, the processor 226 or the processor 234 receives a selection from the user 112A via the user interface 274 (FIG. 3A) or the input device 340 (FIG. 5) of the activity 1, the activity 2, or the activity 3 over a period of time, e.g., day 1, day 2, etc., within the GUI 602 and the processor 234 drags the activities performed during the period of time to present in the GUI 606.

When the user 112A uses the user interface 274 (FIG. 3A) or the input device 340 (FIG. 5) to point the cursor 552 to the activity 1 performed during the day 1 within the GUI 606 and selects the activity 1 performed during the day 1 or to point the cursor 552 to the activity 1 performed during the day 2 and selects the activity 1 performed during the day 2 within the GUI 606, a GUI 608 is generated and displayed. The GUI 608 includes an aggregate, e.g., total, etc., activity level 609 of the activity 1 performed during the day 1 and includes an aggregate activity level 610 of the activity 1 performed during the day 2. Any aggregation of activity levels is performed by the processor 226 or by the processor 234.

In some embodiments, upon receiving the selection of the activity 1, the activity 2, or the activity 3 over a period of time, e.g., day 1, day 2, etc., within the GUI 602, the processor 226 or the processor 234 generates a GUI, e.g., the GUI 608, having aggregate activity levels of the activity over the period of time for which the activity is selected.

Figure 7M:
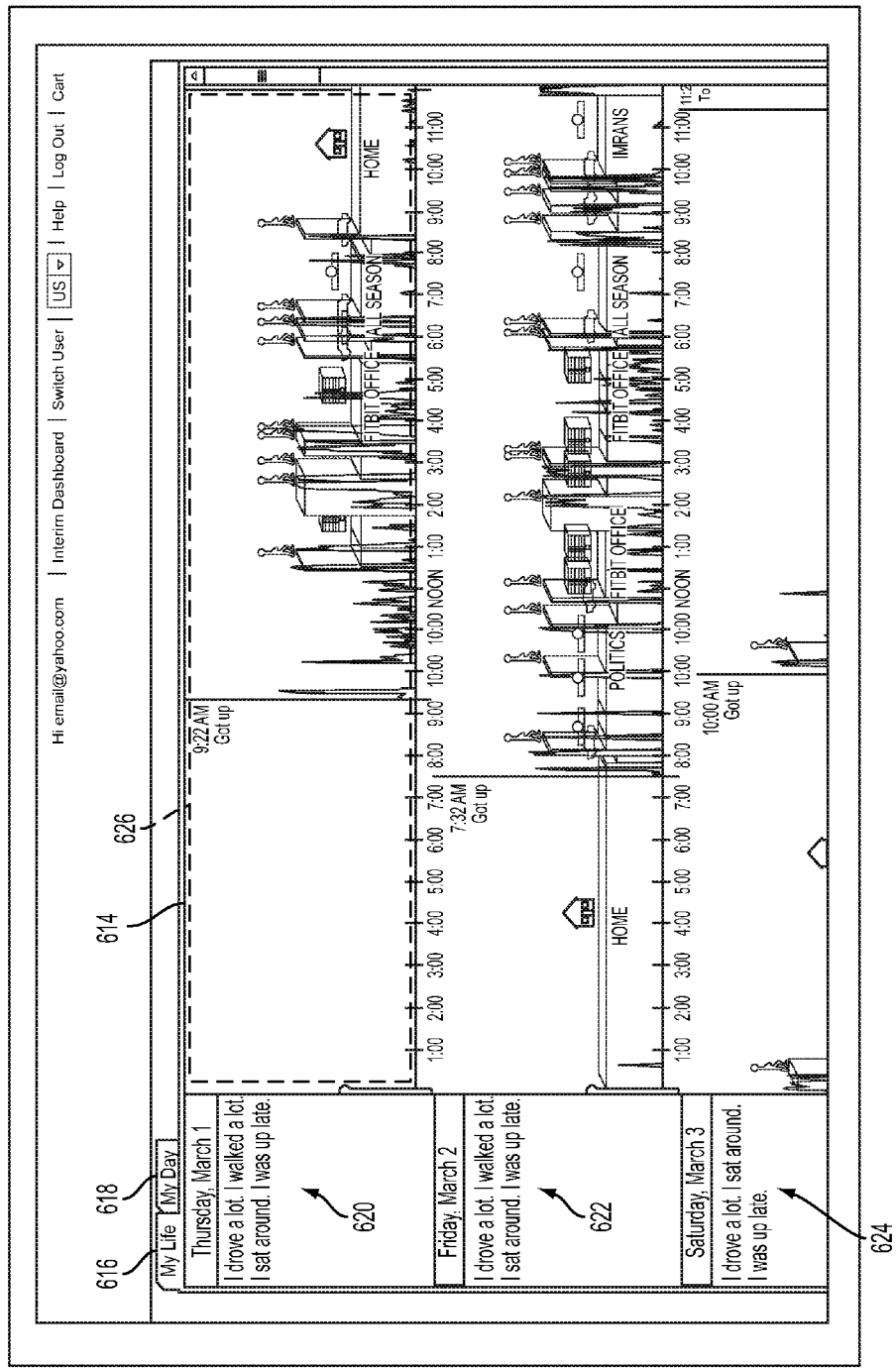
FIG. 7M is a diagram of a GUI that describes an aggregate level of one or more activities performed by a user over a period of time, in accordance with one embodiment described in the present disclosure.

FIG. 7M is a diagram of an embodiment of a GUI 614 that describes an aggregate level of one or more activities performed by the user 112A over a period of time. The processor 226 or the processor 234 determines an aggregate amount of an activity performed by the user 112A over a period of time. The processor 234 or the processor 234 generates a simplified description of the aggregate amount of the activity and displays the simplified description on a corresponding display device. For example, when the user 112A selects a tab 616 via the user interface 274 (FIG. 3A) or the input device 340 (FIG. 5), simplified descriptions 620, 622, and 624 are displayed within the GUI 614 for one or more periods of time. The simplified description 620 is of activities performed by the user 112A on Thursday, March 1, the simplified description 622 is of activities performed by the user 112A on Friday, March 2, and the simplified description 624 is of activities performed by the user 112A on Saturday, March 3.

Each simplified description of activities performed during a period of time is displayed besides a corresponding sequence of events occurring during the period of time. For example, the simplified description 620 of activities performed on Thursday, March 1 is displayed besides one or more events 626 occurring on Thursday, March 1.

Figure 7N:
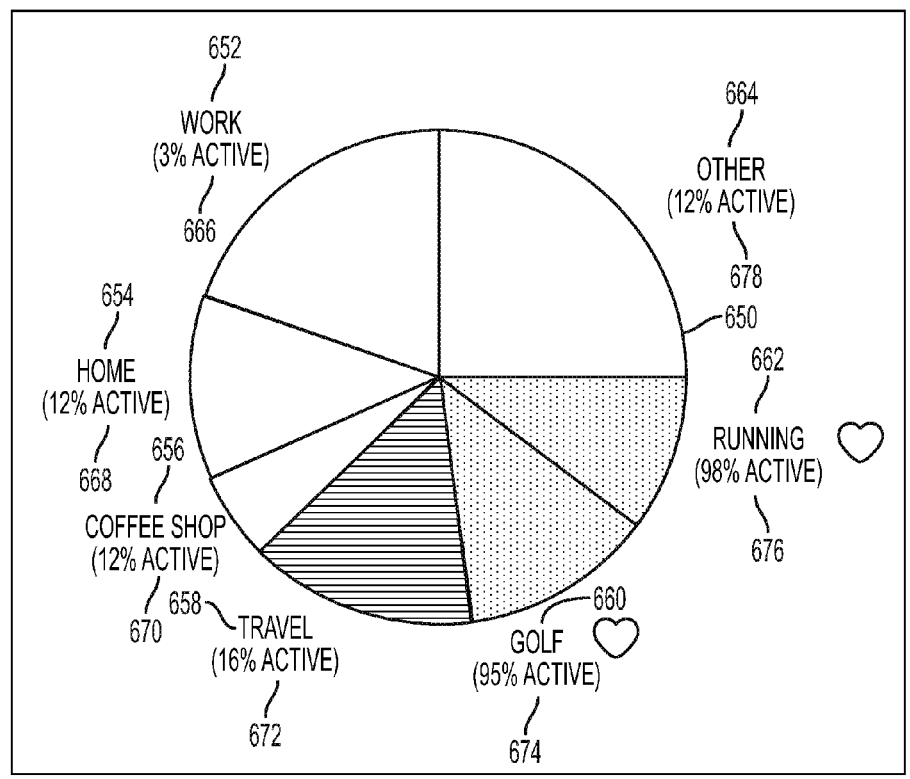
FIG. 7N is a diagram of a pie-chart of locations at which a user performs one or more activities and of percentages of activity levels at one or more locations over a period of time, in accordance with one embodiment described in the present disclosure.
Figure 70:
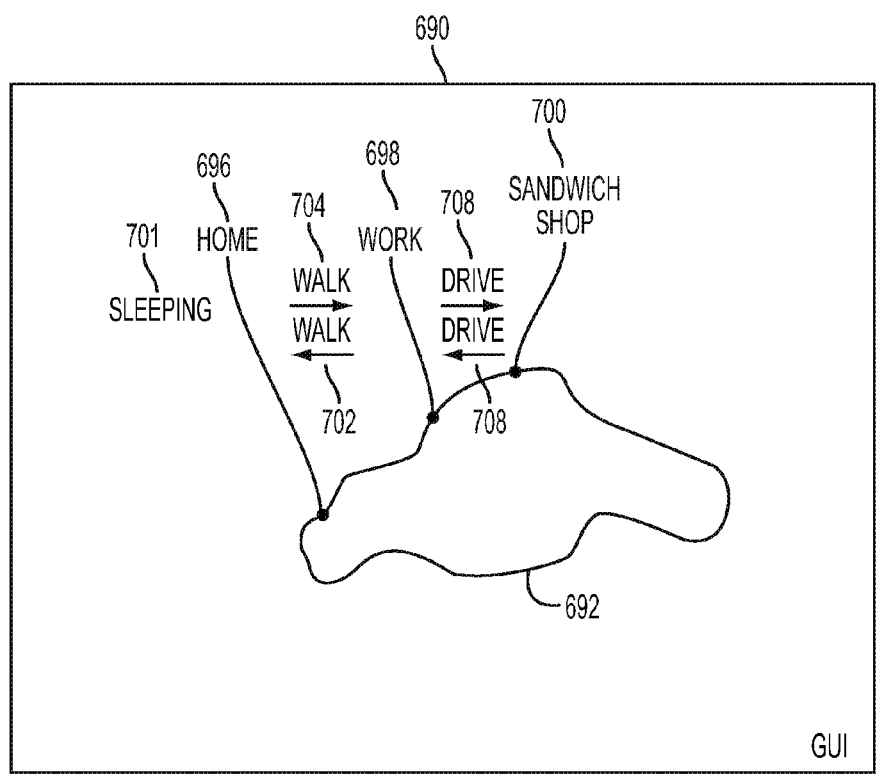

FIG. 7N is a diagram of an embodiment of a pie-chart 650 of locations at which the user 112A performs one or more activities and of percentages of activity levels at the locations over a period of time. The period of time is represented by the pie-chart 650. The pie-chart 650 is generated by the processor 226 or the processor 234.

The pie-chart 650 is segmented into a location 652, a location 654, a location 656, an activity 658, an activity 660, an activity 662, and a location/activity 664. When the user 112A is at the location 652, the user 112A has an activity level of 666. Similarly, when the user 112A is at the location 654, the user 112A has an activity level of 668. When the user 112A is at the location 656, the user 112A has an activity level of 670. Moreover, when the user 112A is performing the activity 658, the user 112A has an activity level of 672. When the user 112A is performing the activity 660, the user 112A has an activity level of 674. Also, when the user 112A is performing the activity 662, the user 112A has an activity level of 676. When the user 112A is performing the activity 664 or is at the location 664, the user 112A has an activity level of 678.

In some embodiments, an activity level of an activity performed at a location by the user 112A is determined by the processor 226 or the processor 234 in terms of a percentage of an amount of activity that would have been performed at the location. For example, the processor 226 or 234 determines that a maximum amount of activity that can be performed by the user 112A or any other user at the location 652 is n. The processor 226 or 234 receives an amount of activity actually performed by the user 112A as m. The processor 226 or 234 determines a percentage (m/n)×100 as the activity level 666.

In various embodiments, any other type of graph, e.g., a bar graph, a line graph, etc., is generated by the processor 226 or the processor 234 instead of a pie chart.

FIG. 7O is a diagram of an embodiment of a GUI 690 that includes an overlay of a map 692 on one or more locations 696, 698, and 700 that the user 112A visits during a period of time to perform one or more activities 701, 702, 704, and 708 performed by the user 112A during the period of time. The GUI 690 is generated by the processor 226 or by the processor 234. The GUI 690 is generated by executing the method 221 (FIG. 6F).

The GUI 690 includes a map 692 of a path traveled by the user 112A during a period of time, text describing the locations 696, 698, and 700 and text describing the activities 701, 702, 704, and 708.

In some embodiments, instead of text describing the locations 696, 698, and 700, one or more graphical elements or a combination of the graphical elements and text describing the locations are used within the GUI 690 to indicate the locations. In various embodiments, instead of text describing the activities 701, 702, 704, and 708, one or more graphical elements or a combination of the graphical elements and text describing the activities are used within the GUI 690 to indicate the activities.

In a number of embodiments, the one or more locations 696, 698, and 700 are overlaid on the map 692.

Figure 7P:
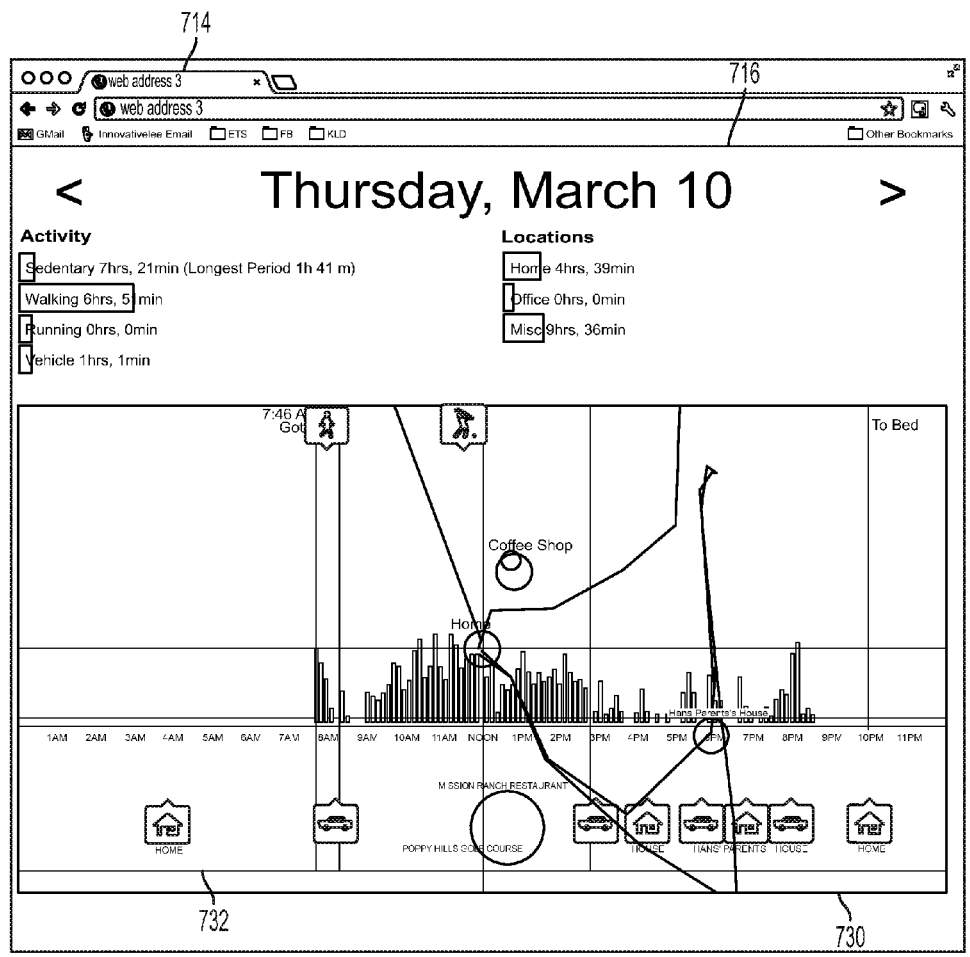
FIG. 7P is a diagram of a web page that illustrates that a map is overlaid on an event region to indicate a geo-location of a user at a time within a time period in which the user performs one or more activities, in accordance with one embodiment described in the present disclosure.

FIG. 7P is a diagram of an embodiment of a web page 714 that illustrates that a map 732 is overlaid on the event region 730 to indicate a geo-location of the user 112A at a time, e.g., an hour, a minute, etc., within a time period in which the user 112A performs one or more activities. The web page 714 includes a GUI 716 that further includes the map 732 and the event region 730. When the user 112A selects a time, e.g., 11 AM, NOON, 1 PM, etc., on the GUI 370 (FIG. 7A) via the user interface 274 (FIG. 3A) or the input device 340 (FIG. 5), a map, e.g., the map 732, etc., is overlaid by the processor 226 or the processor 234 on the GUI 370 to indicate a geo-location of the user 112A at the time. For example, the geo-location is indicated by centering the map at the geo-location of the user 112A at the time.

The GUI 716 is generated by executing the method 102 (FIG. 6A), 160 (FIG. 6B), 170 (FIG. 6C), or 210 (FIG. 6E) in combination with the method 221 (FIG. 6F).

In some embodiments, the event region 730 is overlaid on the map 732.

Figure 7Q:
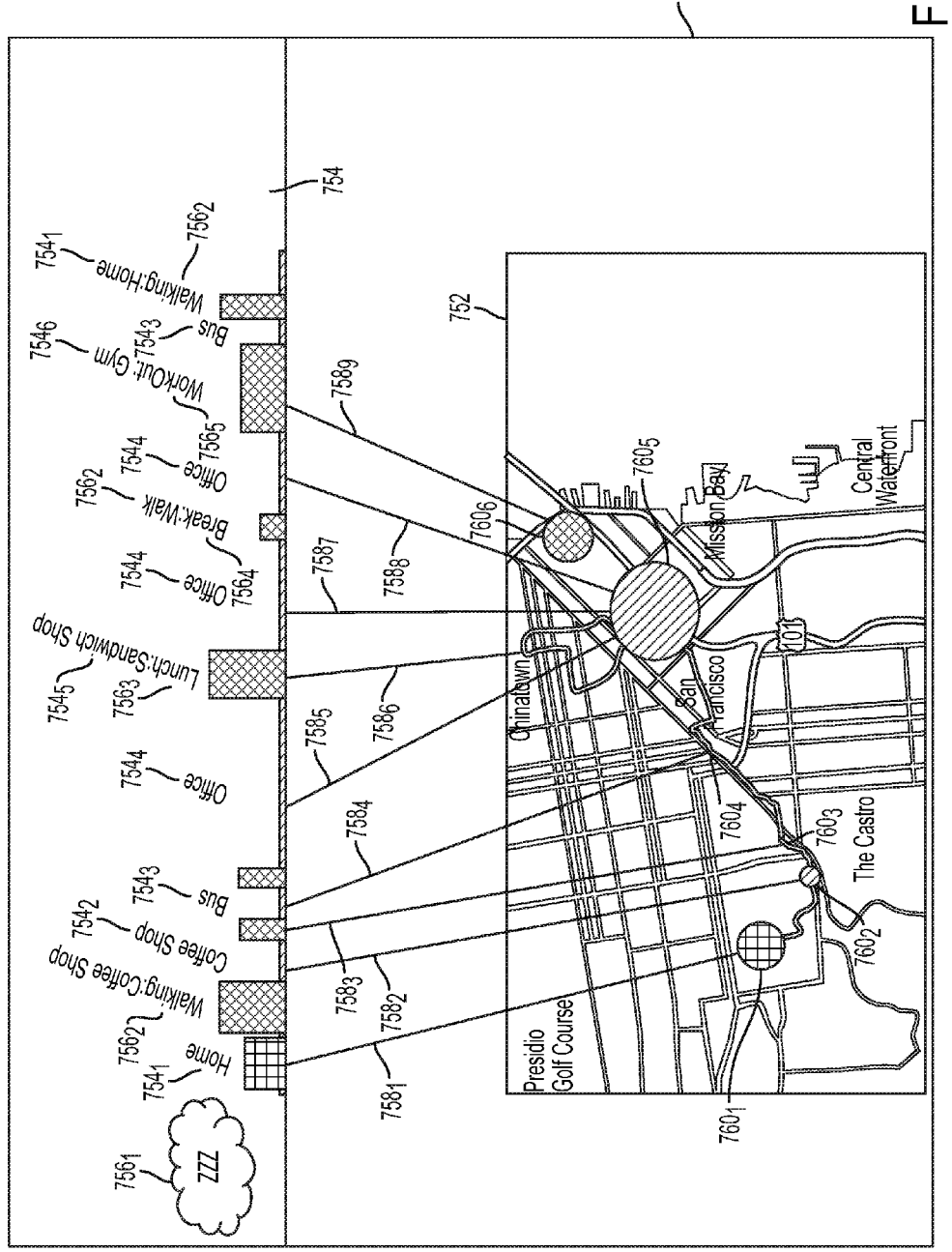
FIG. 7Q is a diagram of a GUI that includes a map below an event region, in accordance with one embodiment described in the present disclosure.

FIG. 7Q is a diagram of an embodiment of a GUI 750 that includes a map 752 below an event region 754. The GUI 750 is generated by the processor 226 or the processor 234. The event region 754 includes one or more location/activity identifiers $754_1$, $754_2$, $754_3$, $754_4$, $754_5$, and $754_6$ of locations visited by the user 112A during a period of time. Moreover, the event region 754 includes graphical elements and/or text that represent one or more activities $756_1$, $756_2$, $756_3$, $756_4$, and $756_5$ performed by the user 112A during the period of time.

The GUI 750 further includes links $758_1$, $758_2$, $758_3$, $758_4$, $758_5$, $758_6$, $758_7$, $758_8$, and $758_9$ between a set including one or more geo-locations $760_1$, one or more geo-locations $760_2$, one or more geo-locations $760_3$, one or more geo-locations $760_4$, one or more geo-locations $760_5$, and one or more geo-locations $760_6$ on the map 752 and a set including one or more of the location/activity identifiers $754_1$, $754_2$, $754_3$, $754_4$, $754_5$, and $754_6$ and/or one or more of the activities $756_1$, $756_2$, $756_3$, $756_4$, and $756_5$. For example, the link $758_1$ is established between the one or more geo-locations $760_1$ and the location $754_1$.

The GUI 750 is generated by executing the method 102 (FIG. 6A), 160 (FIG. 6B), 170 (FIG. 6C), or 210 (FIG. 6E) in combination with the method 221 (FIG. 6F).

In some embodiments, a geo-location is represented as a graphical element and/or as text by the processor 226 or by the processor 234.

In some embodiments, the map 752 is placed by the processor 236 or the processor 234 at any other place, e.g., above, to the left of, to the right of, etc., with respect to the event region 754.

Figure 7R:
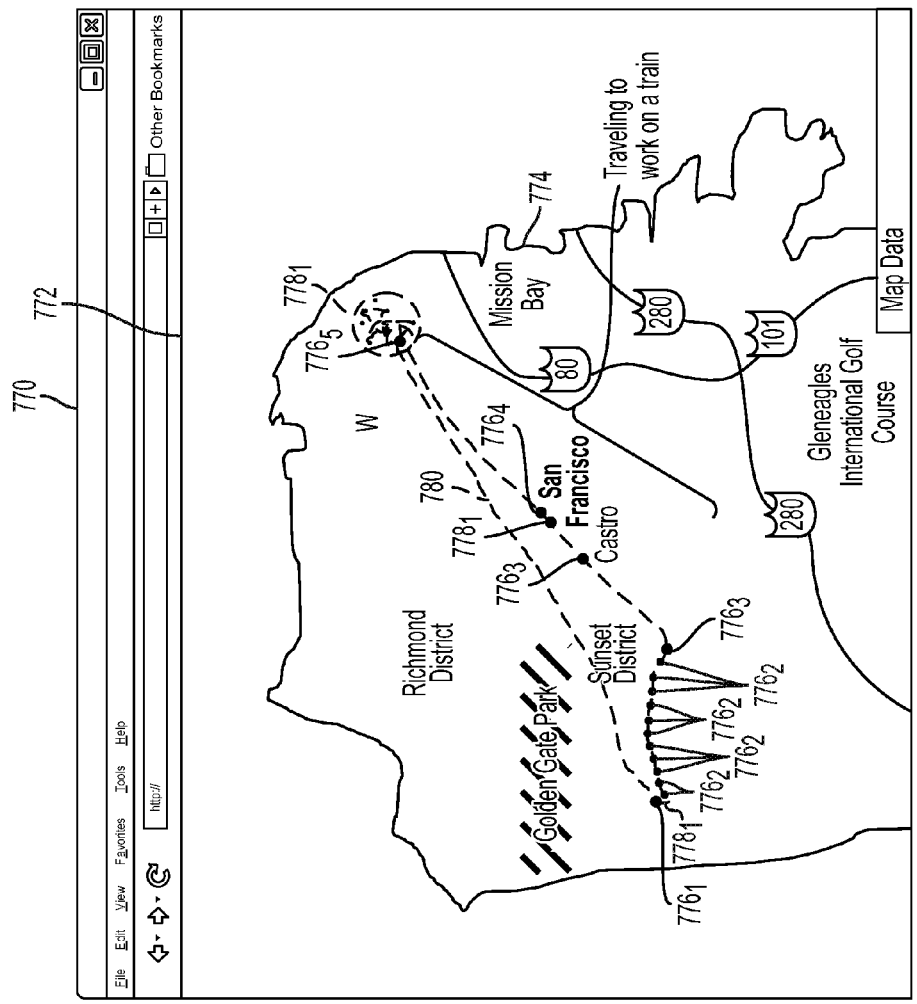
FIG. 7R is a diagram of a web page that is used to illustrate an overlay of event data on a map, in accordance with one embodiment described in the present disclosure.

FIG. 7R is a diagram of an embodiment of a web page 770 that is used to illustrate an overlay of event data on a map 774. A map is accessed by the processor 234 of the monitoring device 108A via the wireless communication device 278 (FIG. 3A) or a wired communication device of the monitoring device 108A and the network 176 (FIG. 3A) from the geo-location-location database of the server 228 (FIG. 3A) or another server without using the computing device 166 (FIG. 3A). In some embodiments, the map 774 is accessed by the processor 234 of the monitoring device 108A via the wireless communication device 278 (FIG. 3A) or a wired communication device of the monitoring device 108A, the computing device 166, and the network 176 (FIG. 3A) from the geo-location-location database of the server 228 (FIG. 3A) or another server. In a number of embodiments, the map 774 is accessed by the processor 226 of the computing device 166 via the NIC 356 (FIG. 5) of the computing device 166 and via the network 176 (FIG. 3A) from the geo-location-location database of the server 228 (FIG. 3A) or another server.

The web page 770 includes a GUI 772 that is displayed by the processor 226 or the processor 234. The GUI 772 is generated by the processor 226 or the processor 234. The GUI 772 is generated by executing the method 102 (FIG. 6A), 160 (FIG. 6B), 170 (FIG. 6C), or 210 (FIG. 6E) in combination with the method 221 (FIG. 6F).

The map 774 includes one or more geo-locations, names of landmarks accessed from the geo-location-location database, names of public places accessed from the geo-location-location database, names of streets accessed from the geo-location-location database, names of geo-locations accessed from the geo-location-location database, or a combination thereof, etc.

The event data is overlaid on the map 774 by the processor 226 or by the processor 234. The event data includes one or more of a location/activity identifier $776_1$, e.g., a home identifier, etc., a location/activity identifier $776_2$, e.g., an identifier of a bus, etc., a location/activity identifier $776_3$, e.g., an identifier of a railway station, etc., a location/activity identifier $776_4$, e.g., a vehicle identifier, etc., a location/activity identifier $776_5$, e.g., a work location/activity identifier, etc., of locations visited by the user 112A during a period of time and an activity identifier $778_1$ of an activity, e.g., walking, etc., performed by the user 112A during the period of time. The event data further includes a path 780 taken by the user 112A during the period of time in visiting the locations having the location/activity identifiers $776_1$, $776_2$, $776_3$, $776_4$, and $776_5$ and in performing an activity, e.g., walking, etc., represented by the activity identifier $778_1$.

In some embodiments, the event data includes activity data of any number of activities performed by the user 112A.

In several embodiments, the map 774 is overlaid on the event data.

Figure 7S:
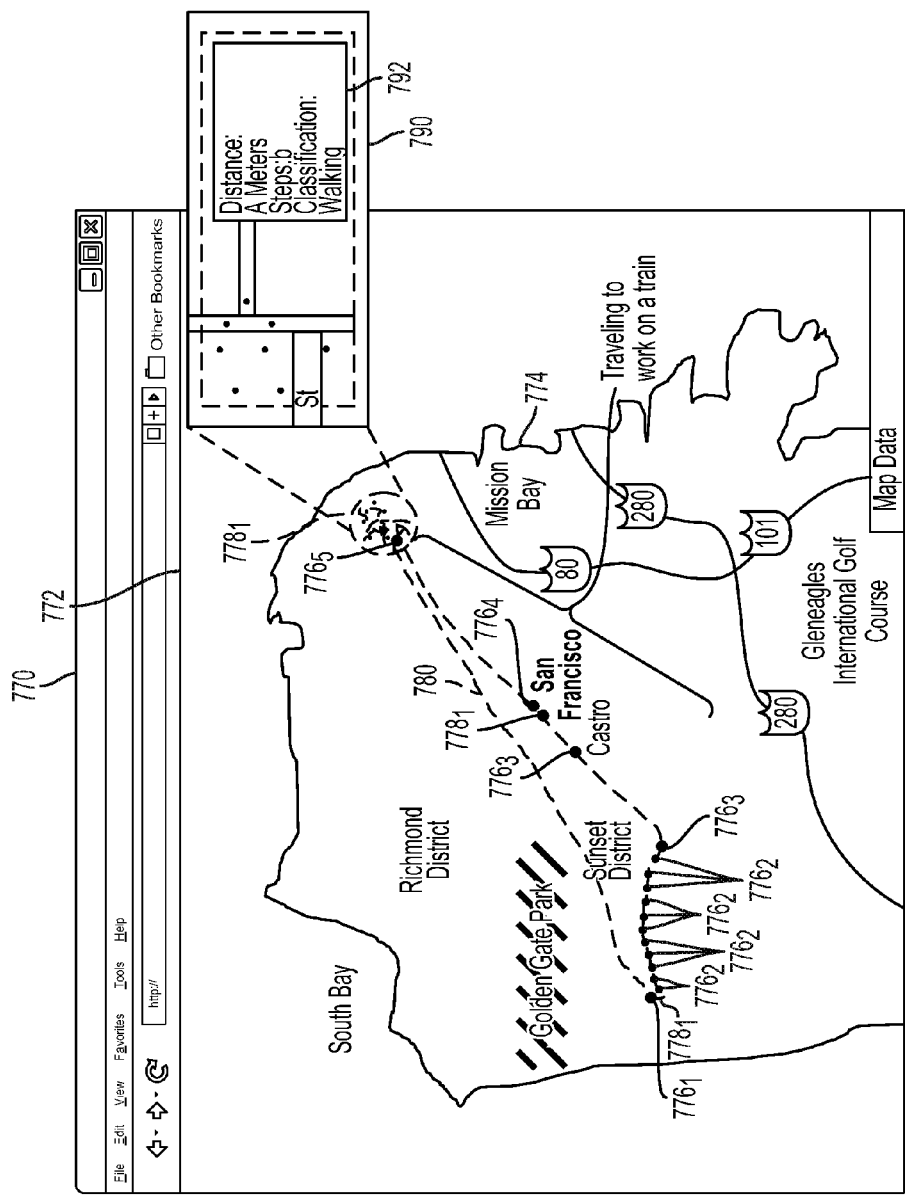
FIG. 7S is a diagram of a web page that is used to illustrate a zoom-in of a portion of the map of FIG. 7R and of activity data of an activity performed by a user while the user is at the portion, in accordance with one embodiment described in the present disclosure.

In various embodiments, the activity identifier $778_1$, the path 780, and/or the location/activity identifiers $776_1$, $776_2$, $776_3$, $776_4$, and $776_5$ are color-coded by the processor 226 or the processor 234. For example, the processor 226 or the processor 234 assigns a different color to the identifier $778_1$ than to one or more of the location/activity identifiers $776_1$, $776_2$, $776_3$, $776_4$, and $776_5$, and the path 780. As another example, the processor 226 or the processor 234 assigns a different color to the location/activity identifier $776_1$ than to one or more of the location/activity identifiers $776_2$, $776_3$, $776_4$, and $776_5$. As another example, the processor 226 or the processor 234 assigns a different color to the path 780 than to one or more of the location/activity identifiers $776_1$, $776_2$, $776_3$, $776_4$, and $776_5$ In some embodiments, the activity identifier $778_1$, the path 780, and/or the location/activity identifiers $776_1$, $776_2$, $776_3$, $776_4$, and $776_5$ are coded by the processor 226 or the processor 234 by using graphical properties. For example, the processor 226 or the processor 234 assigns a different graphical property to the activity identifier $778_1$ than to one or more of the location/activity identifiers $776_1$, $776_2$, $776_3$, $776_4$, and $776_5$, and the path 780. As another example, the processor 226 or the processor 234 assigns a different graphical property to the location/activity identifier $776_1$ than to one or more of the location/activity identifiers $776_2$, $776_3$, $776_4$, and $776_5$. As another example, the processor 226 or the processor 234 assigns a different graphical property to the path 780 than to one or more of the location/activity identifiers $776_1$, $776_2$, $776_3$, $776_4$, and $776_5$ FIG. 7S is a diagram of an embodiment of the web page 770 that is used to illustrate a zoom-in 790 of a portion of the map 774 and of event data of an event that occurs at the portion. When the user 112A uses the uses the user interface 274 (FIG. 3A) or the input device 340 (FIG. 5) to point the cursor 552 to the activity identifier $778_1$, the processor 226 or the processor 234 generates the zoom-in 790 to display the zoom-in 790. In some embodiments, a zoom-in is an example of a GUI.

The zoom-in 790 includes a detailed display 792 associated with the activity identifier 778$_1$ of an activity performed by the user 112A at one or more geo-locations close to, e.g., within a vicinity of, within a radius of, etc., a location having the location/activity identifier 776$_5$. The detailed display 792 includes a distance traveled by the user 112A close to a location having the location/activity identifier 776$_5$, a number of steps taken by the user 112A close to the location, and a textual description of an activity that is identified by the activity identifier 778$_1$ and that is close to, e.g., with a radius of, etc., the location.

In some embodiments, the zoom-in 790 includes any other activity data, e.g., a number of calories burned by the user 112A close to a location having the location/activity identifier 776$_5$, an amount of golf swings taken by the user 112A close to the location, etc.

Figure 7U:
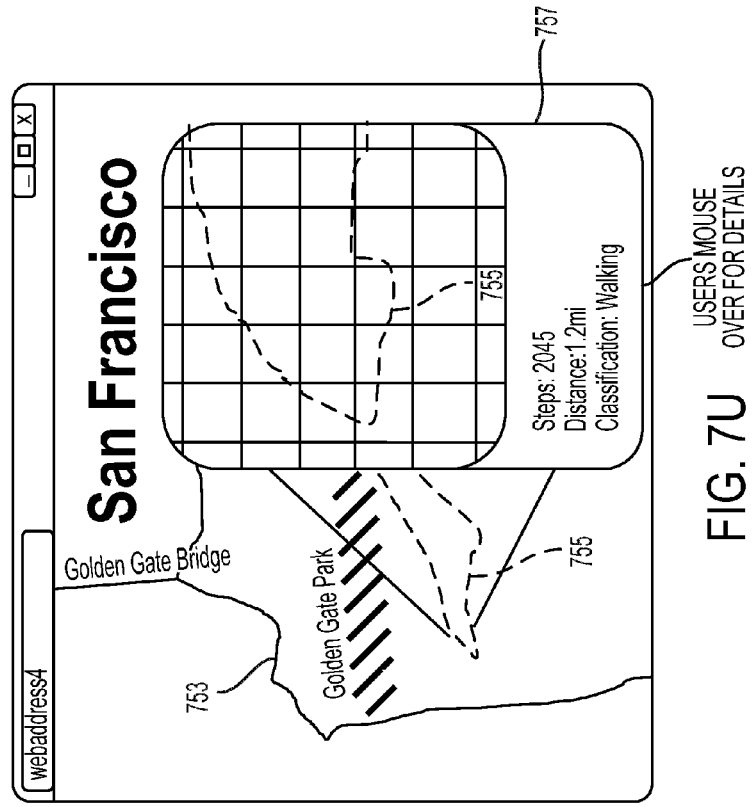
FIG. 7U is a diagram of an embodiment of the web page of FIG. 7T to illustrate a zoom-in of a portion of the map of FIG. 7T and to illustrate activity data associated with the zoom-in, in accordance with one embodiment described in the present disclosure.
Figure 7T:
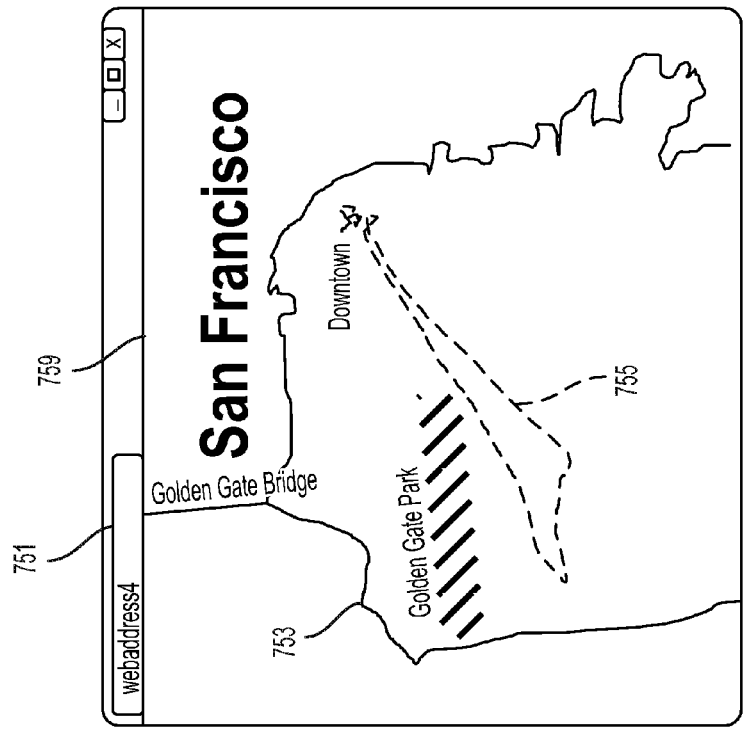
FIG. 7T is a diagram of an embodiment of a web page that includes a GUI that further includes an overlay of a map on a user's path, in accordance with one embodiment described in the present disclosure.

FIG. 7T is a diagram of an embodiment of a web page 751 that includes a GUI 759. The GUI 759 includes an overlay of a map 753 on a user's path 755. The user's path 755 is a path traveled by the user 112A during a period of time. The user's path 755 is coded to distinguish various locations and/or activities along the user's path 755. For example, a bus station is provided a different color by the processor 234 or by the processor 226 than that provided to a railway station. As another example, a walking activity of the user 112A along the user's path 755 is provided a different shade, text, and/or color by the processor 234 or by the processor 226 than that provided to a running activity of the user 112A along the user's path 755. The GUI 759 is generated by executing the method 102 (FIG. 6A), 160 (FIG. 6B), 170 (FIG. 6C), or 210 (FIG. 6E) in combination with the method 221 (FIG. 6F).

In some embodiments, the user's path 755 is overlaid on the map 753.

FIG. 7U is a diagram of an embodiment of a zoom-in 757 that includes a zoom-in of a portion of the user's path 755. The zoom-in 757 is generated when the user 112A points the cursor 552 (FIG. 7I) on a portion of the user's path 755 and selects the portion. The zoom-in 757 is of the portion of the user's path 755. The zoom-in 757 includes activity data, e.g., number of steps walked by the user 112A within the portion, a distance covered by the user 112A within the portion, and a type of activity, e.g., walking, running, etc., performed by the user 112A within the portion.

Figure 7V:
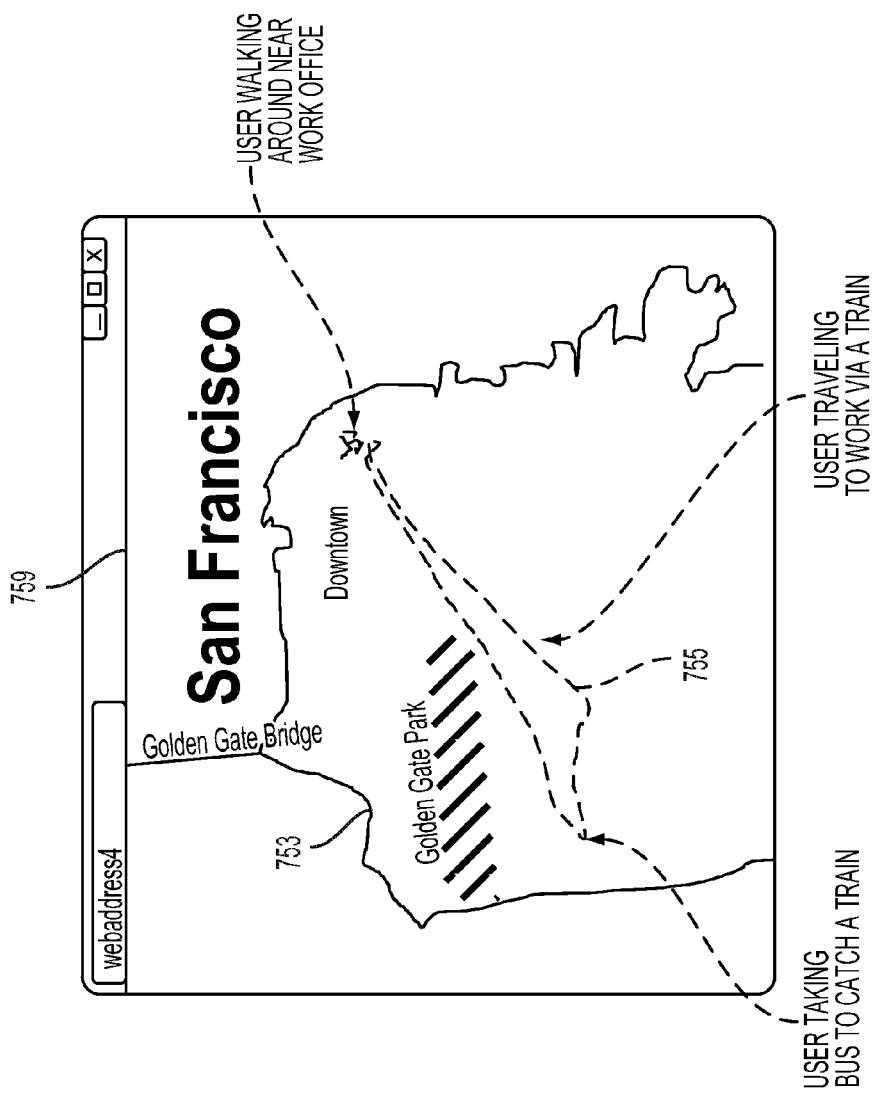
FIG. 7V is a diagram of an embodiment of a GUI that includes further details regarding the user's path of FIG. 7T, in accordance with one embodiment described in the present disclosure.

FIG. 7V is a diagram of an embodiment of the GUI 759 except that the GUI 759 indicates that a portion of the user's path 758 at which the user 112A takes bus to a train is coded differently than a portion of the user's path 758 at which the user 112A is traveling to work on a train and differently than a portion of the user's path 758 where the user 112A is walking around near his/her office.

Figure 8:
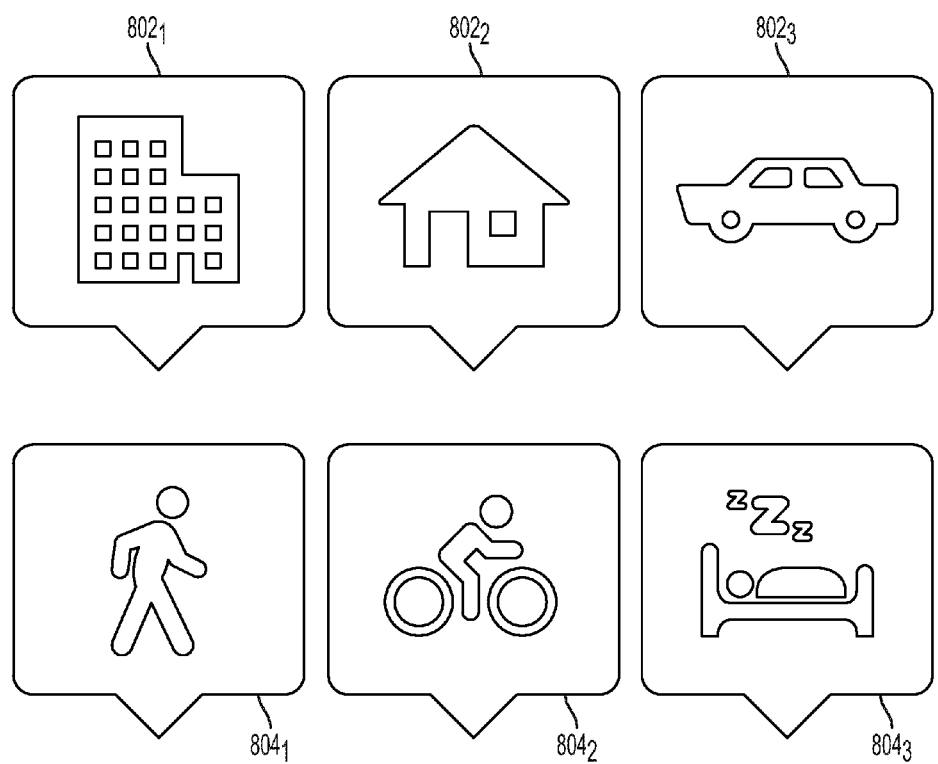
FIG. 8 is a diagram of one or more location identifiers and one or more activity identifiers, in accordance with one embodiment described in the present disclosure.

FIG. 8 is a diagram of an embodiment of one or more location/activity identifiers 802$_1$, 802$_2$, and 802$_3$, and one or more activity identifiers 804$_1$, 804$_2$, and 804$_3$. Each identifier 802$_1$, 802$_2$, 802$_3$, 804$_1$, 804$_2$, and 804$_3$ includes a pointer. For example, the identifier 802$_1$ includes a pointer 806. In some embodiments, each identifier excludes a pointer.

Figure 9A:
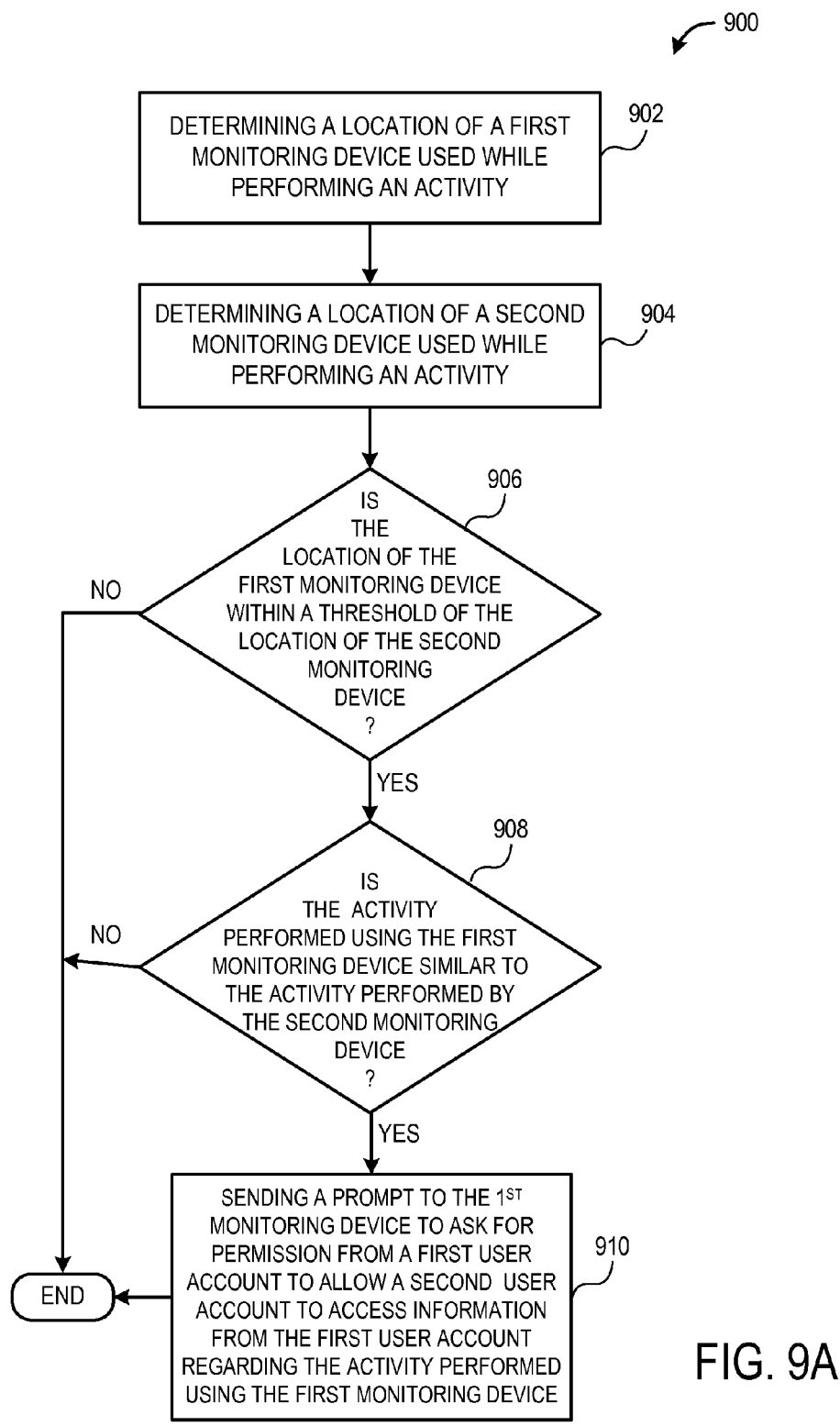
FIG. 9A is a diagram of a method for sharing information between various user accounts based on locations of users and activities performed by the users, in accordance with one embodiment described in the present disclosure.

FIG. 9A is a diagram of an embodiment of a method 900 for sharing information between various user accounts based on locations and activities performed by users. The method 900 is performed by the server 228, or by a virtual machine, or a combination thereof.

The method 900 includes an operation 902 of determining a location of a first monitoring device used by the user 112A while the user 112A is performing an activity. For example, it is determined whether the user 112A is in a gym or at a park or at his home or at work. In some embodiments, the determination 902 is made based on one or more geo-locations of the user 112A, an activity performed by the user 112A, or a combination thereof. The operation 902 is executed by a processor of the server 228.

The method 900 further includes an operation 904 of determining a location of a second monitoring device used by the user 112B while the user 112B is performing an activity. The operation 904 is executed by a processor of the server 228.

The method 900 further includes an operation 906 of determining whether the location of the first monitoring device is within a threshold distance of the location of the second monitoring device. For example, it is determined whether the user 112A and the user 112B are within the same gym. As another example, it is determined whether the user 112A and 112B are at a home of the user 112A. As yet another example, it is determined whether the user 112A and 112B are in the same park. As another example, it is determined whether a geo-location of the user 112A is within a threshold distance of a geo-location of the user 112B. As another example, it is determined whether the location of the first monitoring device is the same as the location of the second monitoring device. The operation 906 is performed by a processor of the server 228.

In some embodiments, a location of the first monitoring device is the same as the location of the second monitoring device when both the locations are located at the same address, or at the same cross streets, or include the same geo-locations, or a combination thereof.

Upon determining that the location of the first monitoring device is not within the threshold distance of the location of the second monitoring device, the method 900 ends. On the other hand, upon determining that the location of the first monitoring device is within the threshold distance of the location of the second monitoring device, an operation 908 of the method 900 is performed. The operation 908 is performed by a processor of the server 228.

In the operation 908, it is determined whether the activity performed by the user 112A using the first monitoring device is similar to the activity performed by the user 112B using the second monitoring device. For example, it is determined whether a combined activity level of the user 112A over a time period is within a pre-determined range of a combined activity level of the user 112B over the time period. To illustrate, it is determined whether a number of calories burnt by the user 112A within an hour is within a pre-determined range of a number of calories burnt by the user 112B within one hour. As another illustration, it is determined whether a number of steps taken by the user 112A within half an hour is within a pre-determined range of a number of steps taken by the user 112B within half an hour. As yet another illustration, it is determined whether a metric determined from an activity performed by the user 112A is within a pre-determined range of a metric determined from an activity performed by the user 112B.

In some embodiments, a combined activity level is generated by a processor of the server 228 by adding activity levels over a time period. In various embodiments, a combined activity level is generated by a processor of the server 228 by determining a maximum value of all activity levels within the time period. In several embodiments, a combined activity level is generated by a processor of the server 228 by determining an average of activity levels within the time period.

As another example of similarity between activities, it is determined whether both the users 112A and 112B are performing the same activity. To illustrate, it is determined whether both the users 112A and 112B are walking. As another illustration, it is determined whether both the users 112A and 112B are running or exercising. As yet another illustration, it is determined whether both the users 112A and 112B are swimming.

Upon determining that the activity performed by the user 112A while using the first monitoring device is not similar to the activity performed by the user 112B while using the second monitoring device, the method 900 ends. On the other hand, upon determining that the activity performed by the user 112A is similar to the activity performed by the user 112B, an operation 910 of the method 900 is performed. The operation 910 is performed by a processor of the server 228.

In the operation 910, a prompt is generated and provided to the first monitoring device to ask for permission from a first user account, e.g., the user account 174 of the user 112A, etc., to allow a second user account, e.g., the user account 912 (FIG. 2A) of the second user 112B, etc., to access information from the first user account regarding the activity of the user 112A. The activity is performed by the user 112A while the user 112A is wearing the first monitoring device. For example, a processor of the server 228 sends via a NIC of the server 228 and the network 176 (FIG. 2A) the prompt to the first monitoring device. In this example, the prompt requests that the user account 912 be provided access to activity levels of the user 112A. The activity levels are of the activity performed while the user 112A is at the location determined in the operation 902. As another example, a processor of the server 228 sends the prompt to the user account 174 displayed on the first monitoring device and the prompt requests permission from the user 112A to allow metrics of the activity performed by the user 112A to be displayed within the user account 912. The activity is performed by the user 112A at the location determined in the operation 902.

Figure 11:
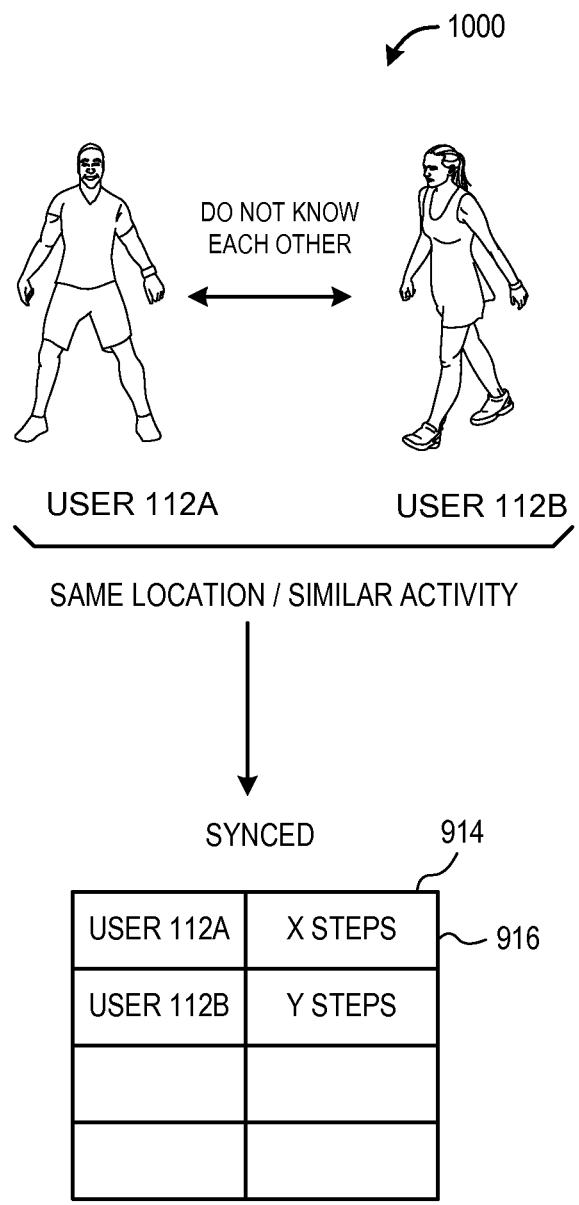
FIG. 11 is a diagram of an embodiment of a system in which users are performing activities at a location and information is shared between the users, in accordance with one embodiment described in the present disclosure.

Examples of information regarding the activity of the user 112A includes an activity level of the activity, a metric of the activity, an activity identifier that identifies the activity performed by the user 112A, a location identifier that identifies a location of the first user 112A while performing the activity, or a combination thereof. Another example of information regarding the activity of the user 112A is information 916, which is shown in FIG. 11. Information 916 includes a number of steps taken by the user 112A.

Continuing further with FIG. 9A, when permission is received by the server 228 from the user 112A via the first user account, the information from the first user account is sent to the second user account for display via the second user account on the second monitoring device. For example, a processor of the server 228 receives the permission via a communication of a monitoring device and the network 176 and a NIC of the server 228. In this example, a processor of the server 228 sends the information regarding the activity performed by the user 112A from the first user account via a NIC of the server, the network 176 and a communication device of the second monitoring device to be displayed within a representation of the second user account on a display device of the second monitoring device. An example of the representation of the user account 912 is a representation 914 shown in FIG. 11.

Continuing with FIG. 9A, in some embodiments, when the users 112A and 112B are social network friends, the operation 910 may not be performed. For example, a processor of the server 228 requests a server of a social network to indicate whether the user 112A is a social network friend of the user 112B. Upon receiving a response from the social network server indicating that the user 112A and the user 112B are social network friends, the information regarding the activity performed by the user 112A from the first user account is sent to the second user account for display via the second user account on the second monitoring device. The information is sent without request the permission from the first user account.

The method 900 ends after the operation 910.

Figure 9B:
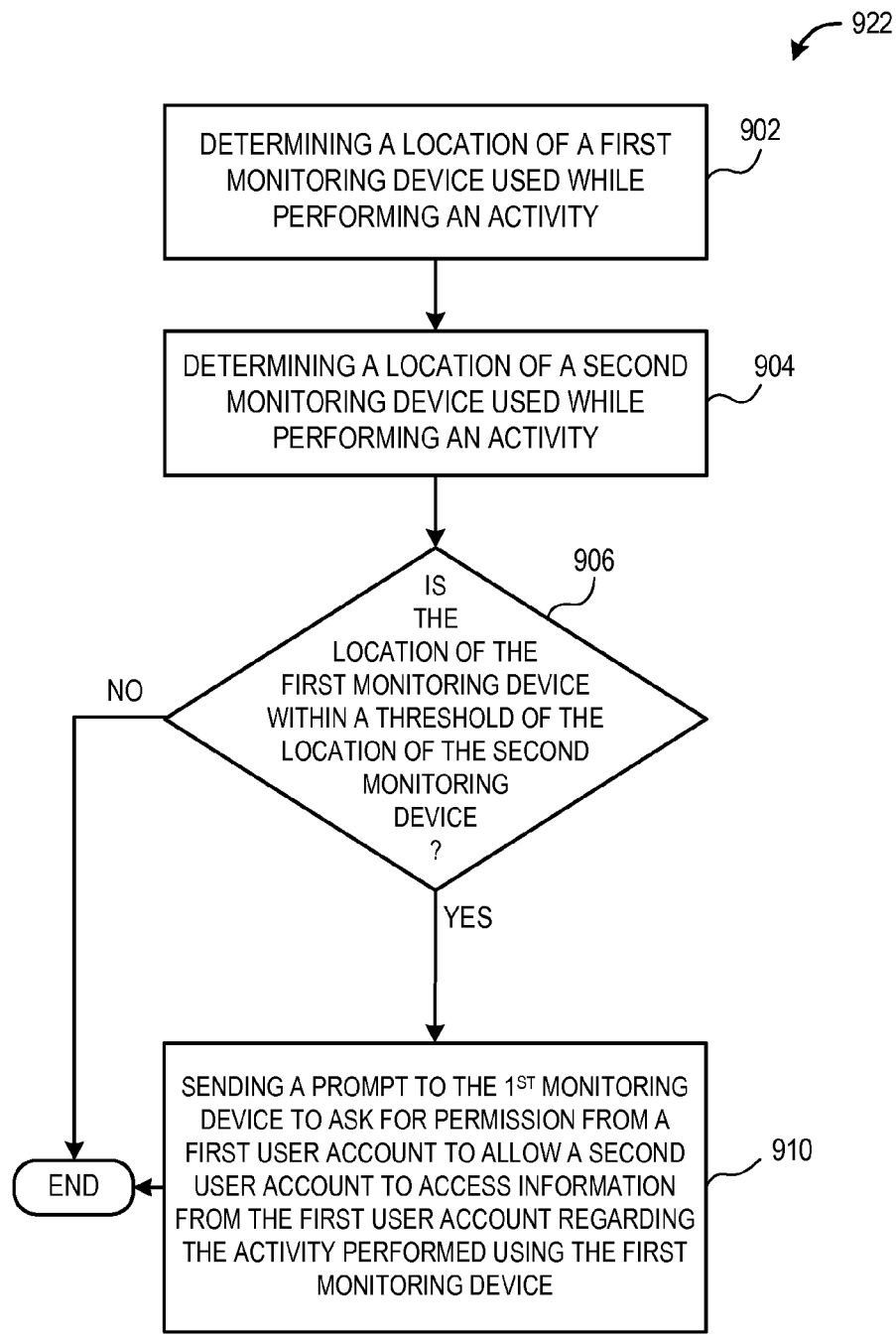
FIG. 9B is a diagram of a method for sharing information between various user accounts based on locations of users, in accordance with one embodiment described in the present disclosure.

FIG. 9B is a diagram of an embodiment of a method 922 for sharing information between various user accounts based on locations of users. The method 922 is performed by the server 228, or by a virtual machine, or a combination thereof.

In the method 922, the operations 902, 904 and 906 are performed.

Moreover, the operation 910 is performed upon determining that the location of the first monitoring device is not within the threshold distance of the location of the second monitoring device.

Figure 10:
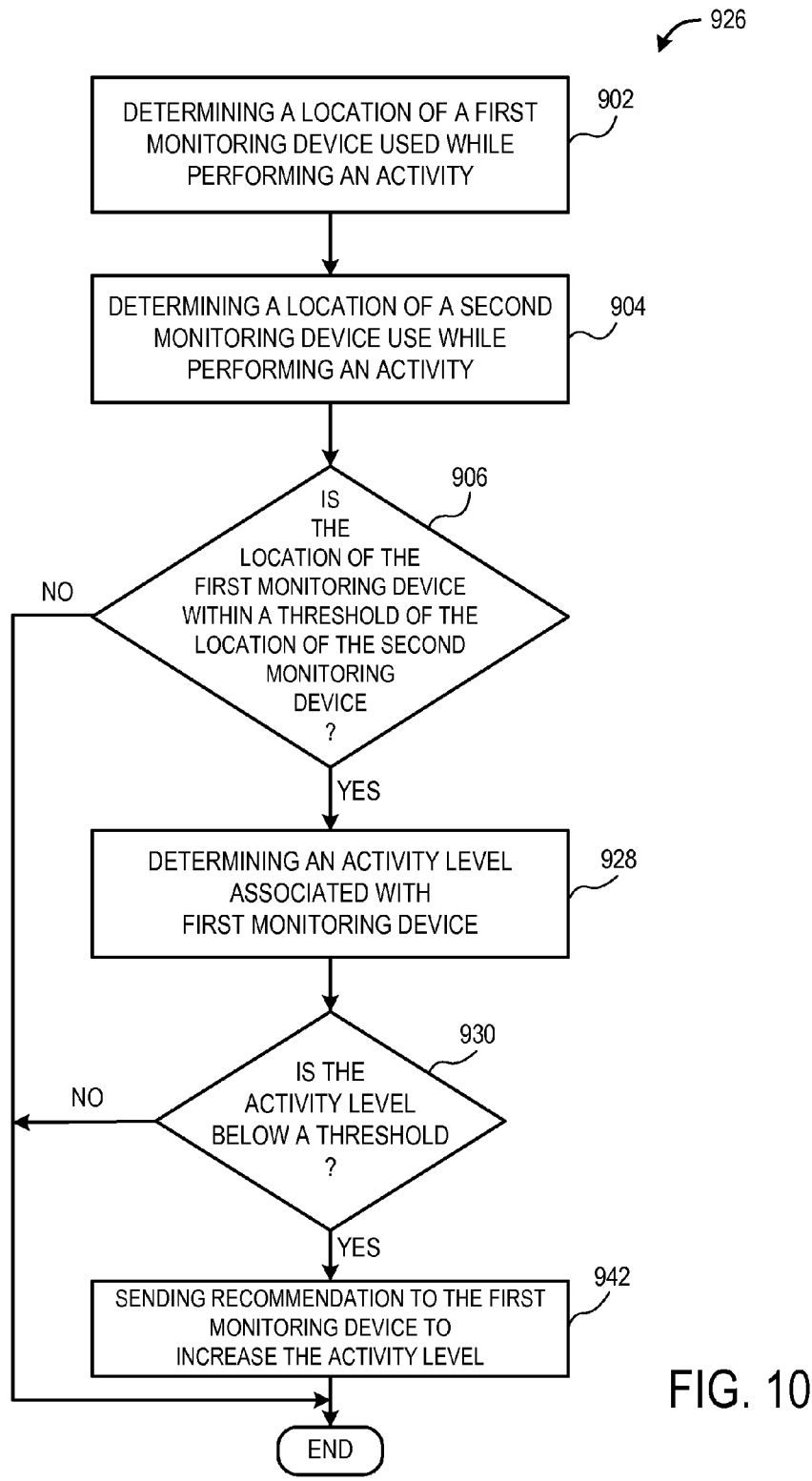
FIG. 10 is a flowchart of a method for recommending a change in activity performed by a user and/or a change in a location at which the activity is performed by the user based on an activity level of the user, in accordance with one embodiment described in the present disclosure.

FIG. 10 is a flowchart of an embodiment of a method 940 for recommending a change in activity performed by the user 112A and/or a change to a location at which the activity is performed by the user 112A based on an activity level of the user 112A. The method 940 is performed by the server 228, or a virtual machine, or a combination thereof.

In the method 940, the operations 902, 904, and 906 are performed. Moreover, an operation 928 is performed by a processor of the server 228 upon determining that the location of the first monitoring device within the threshold distance of the location of the second monitoring device. In some embodiments, a threshold distance includes a defined distance. In the operation 928, an activity level associated with the first monitoring device is determined. The activity level is of one or more activities performed by the user 112A while the user 112A is at the location determined in the operation 902 and is using the first monitoring device. For example, a number of steps of the user 112A who wears the first monitoring device at the location determined in the operation 902 is determined. As another example, a number of calories burned by the user 112A while wearing the first monitoring device is determined. As another example, a number of laps taken in a swimming pool by the user 112A while wearing a monitoring device is determined. An example of the activity level determined in the operation 928 is illustrated as an activity level 936 in FIG. 12.

Continuing further with FIG. 10, the activity level is determined in the operation 928 over a period of time. For example, a statistical value of activity levels of one or more activities performed by the user 112A over a period of time while the user 112A is at the location is determined. In this example, the location is determined in the operation 902. Examples of the statistical value of activity levels include an average of activity levels, or a maximum of activity levels, or a minimum of activity levels, or a median of activity levels, or a combination thereof.

In some embodiments, instead of determining an activity level, the activity level is received from a monitoring device by a processor of the server 228 via a communication device of the monitoring device, the network 176, and a NIC of the server 228.

In various embodiments, upon determining that the location of the first monitoring device is within the threshold distance of the second monitoring device, the operation 908 of determining whether the activity performed by the user 112A using the first monitoring device is similar to the activity performed by the user 112B using the second monitoring device is performed. Upon determining that the activities are not similar, the method 940 ends. On the other hand, upon determining that the activities are similar, the operation 928 is performed. In some embodiments, the operation 908 is performed before or simultaneous with performing the operation 906.

The method 940 includes performing an operation 930 of determining whether the activity level determined in the operation 928 is below an activity level threshold. An example of the activity level threshold is shown as a threshold 938 in FIG. 12. Referring back to FIG. 10, the operation 930 is performed by a processor of the server 228.

Upon determining that the activity level determined in the operation 928 is not below the activity level threshold, e.g., is equal to above the activity level threshold, etc., the method 940 ends. On the other hand, upon determining that the activity level of the operation 928 is below the activity level threshold, a recommendation is sent in an operation 942 of the method 940. The operation 942 is performed by a NIC of the server 228.

A processor of the server 228 generates the recommendation to increase the activity level determined in the operation 928. For example, it is recommended that the user 112A perform a different activity than that performed and used to determine the activity level of the operation 928. To illustrate, it is recommended that the user 112A run instead of walk. As another illustration, it is recommended that the user 112A train using weights instead of doing push-ups.

As another example of the recommendation for increasing the activity level, it is recommended that that the user 112A perform an activity at a different location than at the location determined in the operation 902. To illustrate, it is recommended that the user 112A run at a park instead of running in a gym. In this illustration, a distance between the park and the gym is determined based on geo-locations of the park and the gym and/or by accessing information from the geo-location-location database and/or from a maps service. The distance is determined by a processor of the server 228. Upon determining that the distance is less than a pre-determined distance, the park is recommended. As another illustration, it is recommended that the user 112A swim in different gym than a gym at which the user 112A swims.

As yet another example of the recommendation for increasing the activity level, it is recommended that the user 112A perform the different activity at the different location. To illustrate, it is recommended that the user 112A run at a park instead of walking at work. As another illustration, it is recommended that the user 112A swim in a gym instead of run at a park. In this illustration, a distance between the park and the gym is determined based on geo-locations of the park and the gym and/or by accessing information from the geo-location-location database. The distance is determined by a processor of the server 228. Upon determining that the distance is less than a pre-determined distance, the gym is recommended.

The method 940 ends after the operation 942.

It should be noted that FIGS. 9A, 9B, and 10 include operations performed by the server 228 with respect to monitoring devices. In some embodiments, the operations of FIGS. 9A, 9B, and 10 apply to computing devices instead of monitoring devices. For example, in these embodiments, the operations described above using FIGS. 9A, 9B, and 10 are performed by the server 228 with respect to computing devices. As another example, in the operation 902 a location of a first computing device that is carried by the user 112A is determined and in the operation 904, a location of a second computing device that is carried by the user 112B is determined.

In some embodiments, a monitoring device worn by the user 112B is the first monitoring device and a monitoring device worn by the user 112A is the second monitoring device. In these embodiments, the user account 912 of the user 112B is the first user account and the user account 174 of the user 112A is the second user account.

FIG. 11 is a diagram of an embodiment of a system 1000 in which users 112A and 112B are performing activities at a location and information is shared between the users 112A and 112B. The user 112A may or may not know the user 112B. For example, the user 112B is a friend, or a special interest, or a relative, or a family member, or a work mate, or an acquaintance, etc., of the user 112A. As another example, the user 112A meets the user 112B for a first time at a location.

When the users 112A and 112B are performing similar activities at locations, e.g., park, or gym, or club, or dance club, or pub, work or place, or home, or theater, or college, or university, or landmark, etc., that are within a range of each other, the representation 914 is generated within the user account 912 of the user 112B. The representation 914 includes the information 916 and a number of steps taken by the user 112B. The display of the information 916 and the number of steps taken by the user 112B helps determine how the user 112B is performing with respect to the user 112A. The users 112A and 112B may or may not be social network friends.

Figure 12:
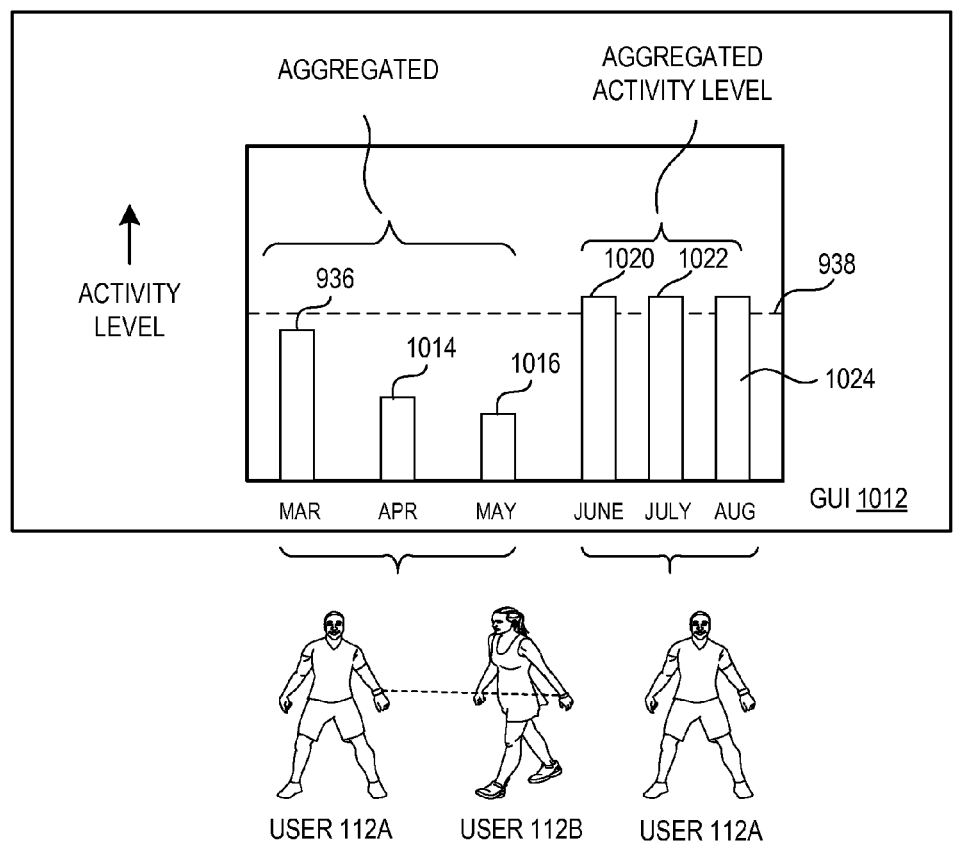
FIG. 12 is a diagram of a system for determining an activity level of a user based on activity and/or a location of the user, in accordance with one embodiment described in the present disclosure.

FIG. 12 is a diagram of an embodiment of a system 1010 for determining an activity level of the user 112A based on activity and/or a location of the user 112A. The system 1010 includes a GUI 1012 that is displayed within a representation of the user account 174 of the user 112A.

Within the GUI 1012, an activity level is plotted versus time. The GUI 1012 is displayed on a display device of a monitoring device that is worn by the user 112A or on a display device of the computing device 166 that is carried by the user 112A. As shown in the GUI 1012, the activity level 936 is below the threshold 938 when the user 112A is performing an activity at a location at which the user 112B is performing an activity. The activity performed by the user 112A may be the same or different from the activity performed by the user 112B.

Moreover, in some embodiments, an aggregated activity level, which is sum of activity levels 936, 1014, and 1016 of one or more activities performed by the user 112A within a time period 1018 is less than the threshold 938. The aggregation, e.g., sum, etc., of activity levels is performed by a processor of the server 228. The aggregated activity level is below the threshold 938 when the user 112A is performing an activity at a location that is within the threshold distance of a location at which the user 112B is performing an activity.

Comparatively, any of activity levels 1020, 1022, and 1024 of one or more activities performed by the user 112A while the user 112A is not at a location within the threshold distance of the location of the user 112B and/or is not performing a similar activity to that performed by the user 112B is greater than the threshold 938.

Moreover, in some embodiments, an aggegated activity level, which is sum of activity levels 1020, 1022, and 1024 of one or more activities performed by the user 112A within a time period 1026 is greater than or equal to the threshold 938. The aggregation, e.g., sum, etc., of activity levels is performed by a processor of the server 228. The aggregated activity level is at least equal to the threshold 938 when the user 112A is performing an activity at a different location that one at which the user 112B is performing an activity.

In various embodiments, a processor applies adaptive learning of locations. For example, a processor determines that a user is at a location and/or achieves an activity level of an activity at the location for a number of times greater than a pre-determined number. The processor further determines a range of times at which the user is at the location for the number of times and/or achieves the activity level at the location. When the user visits the location on a day after the processor determines the range of times, the processor determines whether a time at which the user visits the location falls within the range of times. Upon determining that the time at which the user visits the location at a time that falls within the range of times, the processor determines that the user is at the location and/or will achieve the activity level at the location.

In several embodiments, a processor applies refined learning of location and size. For example, a processor determines that the user 112A visits an inside the user's home and determines that one or more geo-locations within the inside of the home corresponds to the home. In this example, the processor determines that the one or more geo-locations within the inside of the home corresponds to the home based on the geo-location-location database or based on a selection received from the user indicating that the geo-locations correspond to the home. In this example, a processor determines that the user 112A visits a backyard of the user's home and determines that one or more geo-locations of the backyard of the home correspond to the home. In this example, the processor determines that one or more geo-locations of the backyard corresponds to the home based on the geo-location-location database or based on a selection received from the user indicating that the geo-locations correspond to the home. When the user visits a geo-location within the backyard or the inside of the home for a next time, the processor determines that the user is at his/her home. It should be noted that although home is used as an example, in some embodiments, other locations, e.g., a gym, a work place, a golf course, a race track, etc., may be used.

In several embodiments, a processor determines a favorite route of a user based on a number of times the user follows the route. For example, a processor determines that a user follows a route for greater than a pre-determined number of times. In this example, the processor determines that the route is a favorite route of the user. In this example, the processor determines data associate with the route, e.g., a statistical amount of time taken to complete the route, or a location close to the route, or a destination of the route, or a combination thereof, etc. In some embodiments, the processor determines the destination of the route from a maps service or from the geo-location-location database. Examples of the statistical amount of time taken to complete the route include an average amount of time to complete the route, a maximum amount of time to complete the route, a minimum amount of time taken to complete the route, etc. In this example, the processor labels, within a GUI, the route with the data associated with the route. To illustrate, the processor labels a route as "walk to a train" instead of "walk". As another illustration, the processor labels a route as "morning walk to work" instead of "walk". As another illustration, the processor labels a route as "3 mile run down Cedar street" instead of "run". As another illustration, the processor labels a route as "6 mile beach run" instead of "run". Examples of the route include a dog walking route, a commute to work route, a running route, a route to a bus station, a route to a train station, a route to work, a route to home, a route to a friend's home, etc.

In some embodiments, a processor quantifies an emotional response when a user is responsive to a piece of entertainment. The emotional response includes a combination of the HRV and/or the GSR. Based on the emotional response, the processor assigns a rating to the piece of entertainment. For example, when the HRV and/or the GSR indicate to the processor that the user is sleeping during a movie, the processor assigns a low rating to the movie. On the other hand, when the HRV and/or the GSR indicate to the processor that the user is excited during the movie, the processor assigns a high rating to the movie. Based on the HRV and/or the GSR, the processor determines a type of the piece of entertainment that the user likes. In some embodiments, the processor prompts a user to provide the rating. The piece of entertainment may be a movie, an opera, a ballet, a concert, a song, a multimedia presentation, a television show, news, etc. Examples of a type of the piece of entertainment include a horror piece, an action piece, a drama piece, a sad piece, a comedy piece, etc.

In various embodiments, a processor determines that a user is at a location at which the piece of entertainment is presented, e.g., publicly displayed, shown, etc., and displays within a GUI that includes event data information regarding the location. For example, a processor determines that a user is at a movie theater and populates a GUI with show times of movies at the theater. The show times of the movies are obtained from a website or a database that is used to present the show times. Other examples of information regarding the location include video games available at a theater, types of food available at a concert, etc.

In various embodiments, a processor determines motion and location features from users to build a network database. For example, the processor determines that a user performs an activity at a location for a number of times and performs a motion signature that identifies the activity for the number of times. The motion signature is a motion of a user that is substantially repeated over a time period. For example, a first swimming motion when the user is at a swimming pool in a gym is performed on day 1 and a second swimming motion when the user is at the swimming pool at the gym is performed on day 2. The first and second motions are within a standard deviation. When the user visits, e.g., enters, etc., the location at another time, e.g., day 3, etc., the processor determines that the user is going to perform the same activity that the user has performed for the number of times. For example, the processor determines based on the motion signature and the location visited for the number of times as soon as the user enters a gym that the user will swim at the gym. As another example, the processor determines that the user will do yoga at a yoga place based on the motion signature and the location visited for the number of times.

It should be noted that in some embodiments, any method or function or operation that is described herein as being performed by the processor 226 of the monitoring device 108A (FIG. 3A) or by the processor 234 of the computing device 166 (FIG. 5) may be performed by the processor 302 (FIG. 3B) of the monitoring device 108B or by the processor 190 (FIG. 2A) of the server 228.

In some embodiments, functions or methods or operations described herein as being performed by a processor of a device are performed by one or more processors of the device. For example, a function of displaying a GUI is performed by a GPU (not shown) of the monitoring device 108A instead of by the processor 234 (FIG. 3A).

In a number of embodiments, all GUIs, described herein, are accessed by the user 112A when the user 112A accesses the user account 174 (FIG. 2A).

It should be noted that several embodiments are described using a monitoring device. In some embodiments, embodiments that apply to the monitoring device also apply to the computing device 166. For example, instead of a geo-location of a monitoring device being obtained by the monitoring device, a geo-location of the computing device 166 is obtained by the computing device 166. As another example, instead of event data determined by a processor of a monitoring device, event data is determined by a processor of the computing device 166.

In several embodiments, an activity level of a user is a level of a physiological parameter of the user.

In various embodiments, a web page is a GUI.

Embodiments described in the present disclosure may be practiced with various computer system configurations including hand-held devices, microprocessor systems, microprocessor-based or programmable consumer electronics, minicomputers, mainframe computers and the like. Several embodiments described in the present disclosure can also be practiced in distributed computing environments where tasks are performed by remote processing devices that are linked through a wire-based or wireless network.

With the above embodiments in mind, it should be understood that a number of embodiments described in the present disclosure can employ various computer-implemented operations involving data stored in computer systems. These operations are those requiring physical manipulation of physical quantities. Any of the operations described herein that form part of various embodiments described in the present disclosure are useful machine operations. Several embodiments described in the present disclosure also relates to a device or an apparatus for performing these operations. The apparatus can be specially constructed for a purpose, or the apparatus can be a computer selectively activated or configured by a computer program stored in the computer. In particular, various machines can be used with computer programs written in accordance with the teachings herein, or it may be more convenient to construct a more specialized apparatus to perform the required operations.

Various embodiments described in the present disclosure can also be embodied as computer-readable code on a non-transitory computer-readable medium. The computer-readable medium is any data storage device that can store data, which can be thereafter be read by a computer system. Examples of the computer-readable medium include hard drives, network attached storage (NAS), ROM, RAM, compact disc-ROMs (CD-ROMs), CD-recordables (CD-Rs), CD-rewritables (RWs), magnetic tapes and other optical and non-optical data storage devices. The computer-readable medium can include computer-readable tangible medium distributed over a network-coupled computer system so that the computer-readable code is stored and executed in a distributed fashion.

Although the method operations were described in a specific order, it should be understood that other housekeeping operations may be performed in between operations, or operations may be performed in an order other than that shown, or operations may be adjusted so that they occur at slightly different times, or may be distributed in a system which allows the occurrence of the processing operations at various intervals associated with the processing, as long as the processing of the overlay operations are performed in the desired way. For example, the operations 104 and 118 in FIG. 6A are performed simultaneously or the operation 118 is performed before the operation 104. As another example, the operations 202 and 204 of FIG. 6D are performed simultaneously or the operation 204 is performed before performing the operation 202. As yet another example, the operation 223 of FIG. 6F may be performed before, or after, or simultaneous with the performance of the operation 229. As yet another example, the operation 908 of FIG. 9A is performed simultaneous with or before performing the operation 906.

Although the foregoing embodiments have been described in some detail for purposes of clarity of understanding, it will be apparent that certain changes and modifications can be practiced within the scope of the appended claims. Accordingly, the present embodiments are to be considered as illustrative and not restrictive, and the various embodiments described in the present disclosure is not to be limited to the details given herein, but may be modified within the scope and equivalents of the appended claims.

What is claimed is:

1. A method comprising:
   determining a location of a first monitoring device used while performing an activity, the first monitoring device configured to be worn by a first user;
   determining a location of a second monitoring device used while performing an activity, the second monitoring device configured to be worn by a second user;
   determining whether the location of the first monitoring device is within a threshold distance of the location of the second monitoring device;
   determining whether the activity performed using the first monitoring device is similar to the activity performed using the second monitoring device; and
   sending a notification to the first monitoring device upon determining that the activity performed using the first monitoring device is similar to the activity performed using the second monitoring device and that the locations of the first monitoring device is within the threshold distance of the second monitoring device, the notification includes a permission request from a first user account of the first user to allow a second user account of the second user to access information from the first user account regarding the activity performed using the first monitoring device.

2. The method of claim 1, further comprising sending for display within a representation of the second user account the information regarding the activity performed using the first monitoring device.

3. The method of claim 1, further comprising generating a prompt for sending to display the prompt on the second monitoring device upon determining that the activity performed using the first monitoring device is similar to the activity performed using the second monitoring device and that the locations of the first and second monitoring devices are the same, the prompt displayed via the second monitoring device asking for permission from the second user account to allow the first user account to access information from the second user account regarding the activity performed using the second monitoring device.

4. The method of claim 3, further comprising sending for display within a representation of the first user account the information accessed from the second user account regarding the activity performed using the second monitoring device.

5. The method of claim 1, wherein the location of the first monitoring device is generated based on one or more geo-locations of the first monitoring device, wherein the location of the second monitoring device is generated based on one or more geo-locations of the second monitoring device.

6. The method of claim 1, wherein the activity performed using the first monitoring device is similar to the activity performed using the second monitoring device when the activity performed using the first monitoring device has an activity level within a pre-determined range of an activity level of the activity performed using the second monitoring device.

7. The method of claim 1, wherein the activity performed using the first monitoring device is similar to the activity performed using the second monitoring device when the activity performed using the first monitoring device is the same as the activity performed using the second monitoring device.

8. The method of claim 1, wherein the information regarding the activity performed using the first monitoring device includes an activity level of the activity performed using the first monitoring device.

9. The method of claim 1, wherein the notification includes an invitation to meet at a location to perform one or more activities at the location.

10. The method of claim 1, wherein the notification includes a request for permission to post data that the second user is performing an activity at a location with the first user.

11. The method of claim 10, wherein the data is to be posted to a website, wherein the website includes a social network website or a website associated with maintaining event data.

12. A method comprising:
   determining a location of a first monitoring device used while performing an activity, the first monitoring device configured to be worn by a first user;
   determining a location of a second monitoring device used while performing an activity, the second monitoring device configured to be worn by a second user;
   determining whether the location of the first monitoring device is within a defined distance range of the location of the second monitoring device;
   determining an activity level of the activity performed using the first monitoring device when the location of the first monitoring device is within the defined distance range of the location of the second monitoring device;
   determining whether the activity level is below a threshold; and
   sending a recommendation to the first monitoring device upon determining that the activity level is below the threshold.

13. The method of claim 12, wherein the recommendation includes visiting another location than the location of the first monitoring device, or performing another activity than the activity performed using the first monitoring device.

14. The method of claim 12, wherein the first monitoring device is wearable as a watch, or a wrist band, or a clip, and the second monitoring device is wearable as a watch, or a wrist band, or a clip.

15. The method of claim 12, wherein the location of the first monitoring device is generated based on one or more geo-locations of the first monitoring device, wherein the location of the second monitoring device is generated based on one or more geo-locations of the second monitoring device.

16. A method comprising:
   determining a location of a first monitoring device used while performing an activity, the first monitoring device configured to be worn by a first user;
   determining a location of a second monitoring device used while performing an activity, the second monitoring device configured to be worn by a second user;
   determining whether the location of the first monitoring device is within a defined distance range of the location of the second monitoring device;
   sending a prompt to the first monitoring device upon determining that the location of the first device is within the defined distance range of the second monitoring device, the prompt asking for permission from a first user account of the first user to allow a second user account of the second user to access information from the first user account regarding the activity performed using the first monitoring device.

17. The method of claim 16, further comprising sending for display within a representation of the second user account the information regarding the activity performed using the first monitoring device.

18. The method of claim 16, further comprising generating a prompt for sending to display the prompt on the second monitoring device upon determining that the locations of the first and second monitoring devices are the same, the prompt provided via the second monitoring device asking for permission from the second user account to allow the first user account to access information from the second user account regarding the activity performed using the second monitoring device.

19. The method of claim 16, further comprising sending for display within a representation of the first user account the information accessed from the second user account regarding the activity performed using the second monitoring device.

20. The method of claim 16, wherein the location of the first monitoring device is generated based on one or more geo-locations of the first monitoring device, wherein the location of the second monitoring device is generated based on one or more geo-locations of the second monitoring device.

21. The method of claim 16, wherein the information regarding the activity performed using the first monitoring device includes an activity level of the activity performed using the first monitoring device.

22. The method of claim 16, wherein the first monitoring device is wearable as a watch, or a wrist band, or a clip, and the second monitoring device is wearable as a watch, or a wrist band, or a clip.

23. A system comprising:
   a first monitoring device for use by a first user;
   a second monitoring device for use by a second user;
   a processor for determining a location of the first monitoring device used while an activity is performed using the first monitoring device;
   the processor for determining a location of the second monitoring device used while an activity is performed using the second monitoring device;
   the processor for determining whether the location of the first monitoring device is within a threshold distance of the location of the second monitoring device,
   the processor for determining whether the activity performed using the first monitoring device is similar to the activity performed using the second monitoring device, and
   a network interface controller for sending a notification to the first monitoring device upon receiving a determination from the processor that the activity performed using the first monitoring device is similar to the activity performed using the second monitoring device and that the locations of the first monitoring device is within the threshold distance of the second monitoring device, the notification includes a permission request from a first user account of the first user to allow a second user account of the second user to access information from the first user account regarding the activity performed using the first monitoring device.

24. The system of claim 23, wherein the network interface controller for sending for display within a representation of the second user account the information regarding the activity performed using the first monitoring device.

25. The system of claim 23, wherein the network interface is configured to send a prompt to display the prompt on the second monitoring device upon determining that the activity performed using the first monitoring device is similar to the activity performed using the second monitoring device and that the locations of the first and second monitoring devices are the same, the second monitoring device configured to display the prompt to ask for permission from the second user account to allow the first user account to access information from the second user account regarding the activity performed using the second monitoring device.

26. The system of claim 23, wherein the network interface controller is configured to send for display within a representation of the first user account the information accessed from the second user account regarding the activity performed using the second monitoring device.

27. The system of claim 23, wherein the location of the first monitoring device is generated based on one or more geo-locations of the first monitoring device, wherein the location of the second monitoring device is generated based on one or more geo-locations of the second monitoring device.

28. The system of claim 23, wherein the activity performed using the first monitoring device is similar to the activity performed using the second monitoring device when the activity performed using the first monitoring device has an activity level within a pre-determined range of an activity level of the activity performed using the second monitoring device.

29. The system of claim 23, wherein the activity performed using the first monitoring device is similar to the activity performed using the second monitoring device when the activity performed using the first monitoring device is the same as the activity performed using the second monitoring device.

30. The system of claim 23, wherein the information regarding the activity performed using the first monitoring device includes an activity level of the activity performed using the first monitoring device.

\* \* \* \* \*